United States Patent
Cravatt et al.

(10) Patent No.: US 9,249,128 B2
(45) Date of Patent: Feb. 2, 2016

(54) ANTI-CANCER SERINE HYDROLASE INHIBITORY CARBAMATES

(75) Inventors: Benjamin Cravatt, La Jolla, CA (US); Daniel Nomura, San Diego, CA (US); Jae W. Chang, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 13/881,884

(22) PCT Filed: Oct. 21, 2011

(86) PCT No.: PCT/US2011/057321
§ 371 (c)(1),
(2), (4) Date: Jul. 3, 2013

(87) PCT Pub. No.: WO2012/058115
PCT Pub. Date: May 3, 2012

(65) Prior Publication Data
US 2013/0281453 A1    Oct. 24, 2013

Related U.S. Application Data

(60) Provisional application No. 61/479,472, filed on Apr. 27, 2011, provisional application No. 61/407,732, filed on Oct. 28, 2010.

(51) Int. Cl.
| | |
|---|---|
| *C07C 69/017* | (2006.01) |
| *C07D 409/12* | (2006.01) |
| *C07C 271/44* | (2006.01) |
| *C07C 271/46* | (2006.01) |
| *C07C 271/48* | (2006.01) |
| *C07D 207/327* | (2006.01) |
| *C07D 307/86* | (2006.01) |
| *C07D 317/16* | (2006.01) |
| *C07D 403/12* | (2006.01) |
| *C07D 405/12* | (2006.01) |
| *C07D 207/337* | (2006.01) |
| *C07D 307/87* | (2006.01) |
| *C07D 333/24* | (2006.01) |

(52) U.S. Cl.
CPC ............ *C07D 409/12* (2013.01); *C07C 69/017* (2013.01); *C07C 271/44* (2013.01); *C07C 271/46* (2013.01); *C07C 271/48* (2013.01); *C07D 207/327* (2013.01); *C07D 207/337* (2013.01); *C07D 307/86* (2013.01); *C07D 307/87* (2013.01); *C07D 317/16* (2013.01); *C07D 333/24* (2013.01); *C07D 403/12* (2013.01); *C07D 405/12* (2013.01)

(58) Field of Classification Search
CPC .................................................. C07C 69/017
USPC .......................................................... 560/27
See application file for complete search history.

(56) References Cited

U.S. PATENT DOCUMENTS

| | | |
|---|---|---|
| 5,155,132 A | 10/1992 | Venuti et al. |
| 7,696,374 B2 | 4/2010 | Abouabdellah et al. |
| 2007/0155707 A1 | 7/2007 | Dasse et al. |
| 2009/0068107 A1 | 3/2009 | Cravatt et al. |

FOREIGN PATENT DOCUMENTS

| | | |
|---|---|---|
| EP | 0428385 A1 | 5/1991 |
| FR | 2860514 A1 | 4/2005 |
| WO | WO-03/065989 A2 | 8/2003 |
| WO | WO-2007/079180 A2 | 7/2007 |
| WO | WO-2010/057101 A2 | 5/2010 |
| WO | WO-2012/058115 A2 | 5/2012 |

OTHER PUBLICATIONS

Goldfarb. Document No. 151:92837, retrieved from STN; Jul. 16, 2009.*
Abouabdellah, et al. Document No. 142:373569, retrieved from STN; Apr. 8, 2005.*
Tanigawa, et al. Document No. 127:34242, retrieved from STN; Jun. 7, 1997.*
Hagen, et al. Document No. 112:197814, retrieved from STN; May 26, 1990.*
Johnson, et al. Document No. 83:188903, retrieved from STN; May 12, 1984.*
"Database Registry [Online] Chemical Abstracts Service, Columbus, Ohio, retrieved from STN Database accession No. 1002100-87-9", (Feb. 8, 2008), 1 pg.
"Database Registry [Online] Chemical Abstracts Service, Columbus, Ohio, retrieved from STN Database accession No. 947669-76-3", (Sep. 21, 2007), 1 pg.
"Database Registry [Online] Chemical Abstracts Service, Columbus, Ohio, retrieved from STN Database accession No. 947669-71-8", (Sep. 21, 2007), 1 pg.
"Database Registry [Online] Chemical Abstracts Service, Columbus, Ohio, retrieved from STN Database accession No. 947669-67-2", (Sep. 21, 2007), 1 pg.
"Database Registry [Online] Chemical Abstracts Service, Columbus, Ohio, retrieved from STN Database accession No. 947669-57-0", (Sep. 21, 2007), 1 pg.

(Continued)

*Primary Examiner* — Shawquia Jackson
(74) *Attorney, Agent, or Firm* — Schwegman Lundberg & Woessner, P.A.

(57) ABSTRACT

Serine hydrolases are implicated in malconditions such as cancer, central nervous system disorders, cardiovascular disorders, obesity, and metabolic disorders. Many serine hydrolases expressed in proteomic libraries are of unknown function in vivo. Compounds identified through library versus library screening can be used for treatment of malconditions associated with the specific serine hydrolase KIAA1363 (also known as AADACL1). A library of inhibitors of KIAA1363 was prepared and candidate compounds were identified as a potent inhibitors having submicromolar $IC_{50}$ values. An exemplary compound of the invention was shown to be an effective inhibitor of prostate cancer pathogenesis. Other inhibitory compounds of the invention comprising fluorophore groups are shown to be effective in spatial and temporal localization of the serine hydrolase in cells and tissues.

8 Claims, 28 Drawing Sheets

(56) References Cited

OTHER PUBLICATIONS

"Database Registry [Online] Chemical Abstracts Service, Columbus, Ohio, retrieved from STN Database accession No. 947669-35-4", (Sep. 21, 2007), 1 pg.

"Database Registry [Online] Chemical Abstracts Service, Columbus, Ohio, retrieved from STN Database accession No. 947669-34-3", (Sep. 21, 2007), 1 pg.

"Database Registry [Online] Chemical Abstracts Service, Columbus, Ohio, retrieved from STN Database accession No. 857829-80-2", (Aug. 1, 2005), 1 pg.

"Database Registry [Online] Chemical Abstracts Service, Columbus, Ohio, retrieved from STN Database accession No. 855830-81-8", (Jul. 19, 2005), 1 pg.

"Database Registry [Online] Chemical Abstracts Service, Columbus, Ohio, retrieved from STN Database accession No. 855688-62-9", (Jul. 18, 2005), 1 pg.

"Database Registry [Online] Chemical Abstracts Service, Columbus, Ohio, retrieved from STN Database accession No. 745003-71-8", (Sep. 15, 2004), 1 pg.

"Database Registry [Online] Chemical Abstracts Service, Columbus, Ohio, retrieved from STN Database accession No. 581071-84-3", (Sep. 8, 2003), 1 pg.

"Database Registry [Online] Chemical Abstracts Service, Columbus, Ohio, retrieved from STN Database accession No. 581071-68-3", (Sep. 8, 2003), 1 pg.

"Database Registry [Online] Chemical Abstracts Service, Columbus, Ohio, retrieved from STN Database accession No. 491873-73-5", (Feb. 19, 2003), 1 pg.

"Database Registry [Online] Chemical Abstracts Service, Columbus, Ohio, retrieved from STN Database accession No. 491873-71-3", (Feb. 19, 2003), 1 pg.

"Database Registry [Online] Chemical Abstracts Service, Columbus, Ohio, retrieved from STN Database accession No. 332375-27-6", (Apr. 25, 2001), 1 pg.

"Database Registry [Online] Chemical Abstracts Service, Columbus, Ohio, retrieved from STN Database accession No. 64051-16-7", (Nov. 16, 1984), 1 pg.

"Database Registry [Online] Chemical Abstracts Service, Columbus, Ohio, retrieved from STN Database accession No. 64051-15-6", (Nov. 16, 1984), 1 pg.

"Database Registry [Online] Chemical Abstracts Service, Columbus, Ohio, retrieved from STN Database accession No. 64051-08-7", (Nov. 16, 1984), 1 pg.

"Database Registry [Online] Chemical Abstracts Service, Columbus, Ohio, retrieved from STN Database accession No. 63884-81-1", (Nov. 16, 1984), 1 pg.

"European Application Serial No. 11836898.4, Extended European Search Report mailed Apr. 8, 2014", 13 pgs.

Bachovchin, D. A., et al., "Superfamily-wide portrait of serine hydrolase inhibition achieved by library-versus-library screening", *Proc. Natl. Acad. Sci. USA,* 107(49), 20941-20946), 2010.

Rogers, S. A, et al., "Synthesis and bacterial biofilm inhibition studies of ethyl N-(2-phenethyl) carbamate derivatives", *Org Biomol Chem.,* 8(17), (Sep. 7, 2010), 3857-3859.

"International Application Serial No. PCT/US2011/057321, International Preliminary Report on Patentability mailed May 10, 2013", 8 pgs.

"International Application Serial No. PCT/US2011/057321, International Search Report mailed May 22, 2012", 5 pgs.

"International Application Serial No. PCT/US2011/057321, Written Opinion mailed May 22, 2012", 6 pgs.

Chang, Jae Won, et al., "A Potent and Selective Inhibitor of KIAA1363/AADACL1 that Impairs Prostate Cancer Pathogenesis", Chemistry & Biology, 18, (Apr. 22, 2011), 476-484.

Li, W., et al., "A functional proteomic strategy to discover inhibitors for uncharacterized hydrolases.", J Am Chem Soc.. 129(31), (Aug. 8, 2007), 9594-5.

Long, J. Z, et al., "Selective blockade of 2-arachidonoylglycerol hydrolysis produces cannabinoid behavioral effects.", Nat Chem Biol., 5(1), (Jan. 2009), 37-44.

Mor, Macro, et al., "Synthesis and quantitative structure-activity relationship of fatty acid amide hydrolase inhibitors: modulation at the N-portion of biphenyl-3-yl alkylcarbamates", J Med Chem., 51(12), (Jun. 26, 2008), 3487-98.

\* cited by examiner

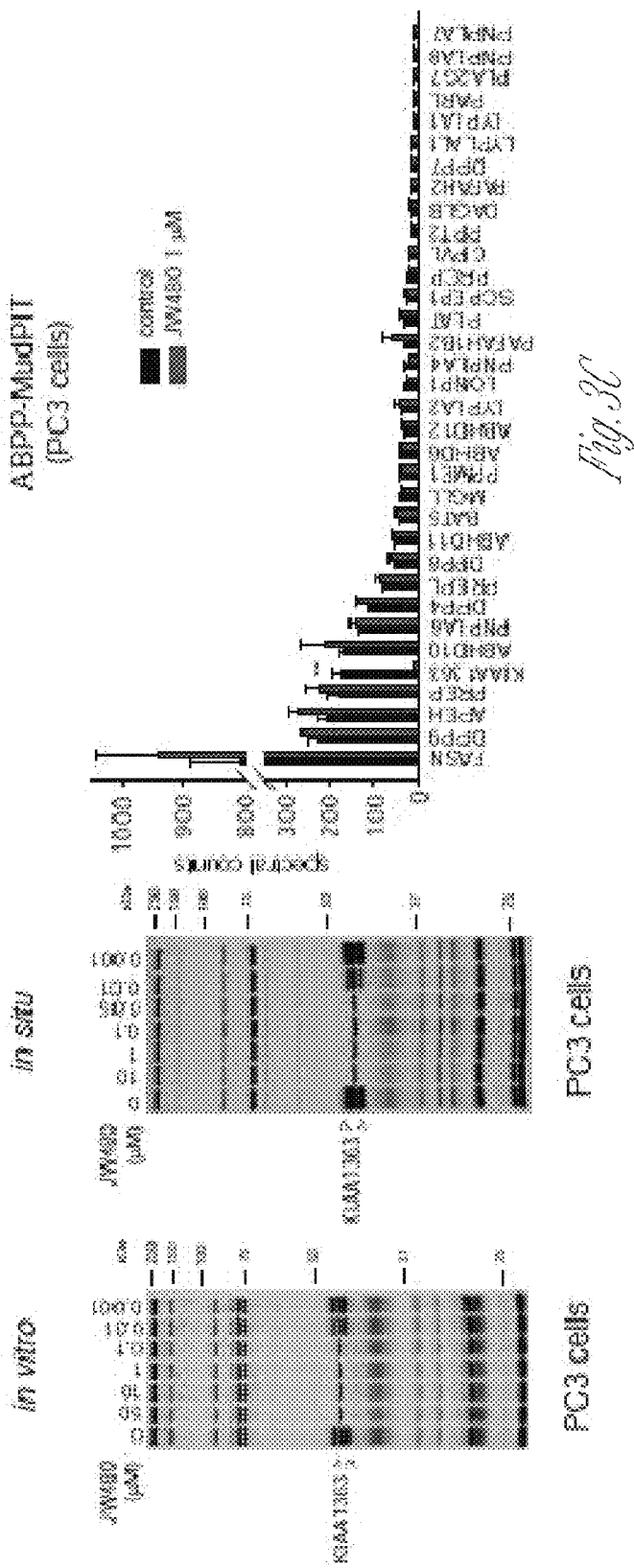

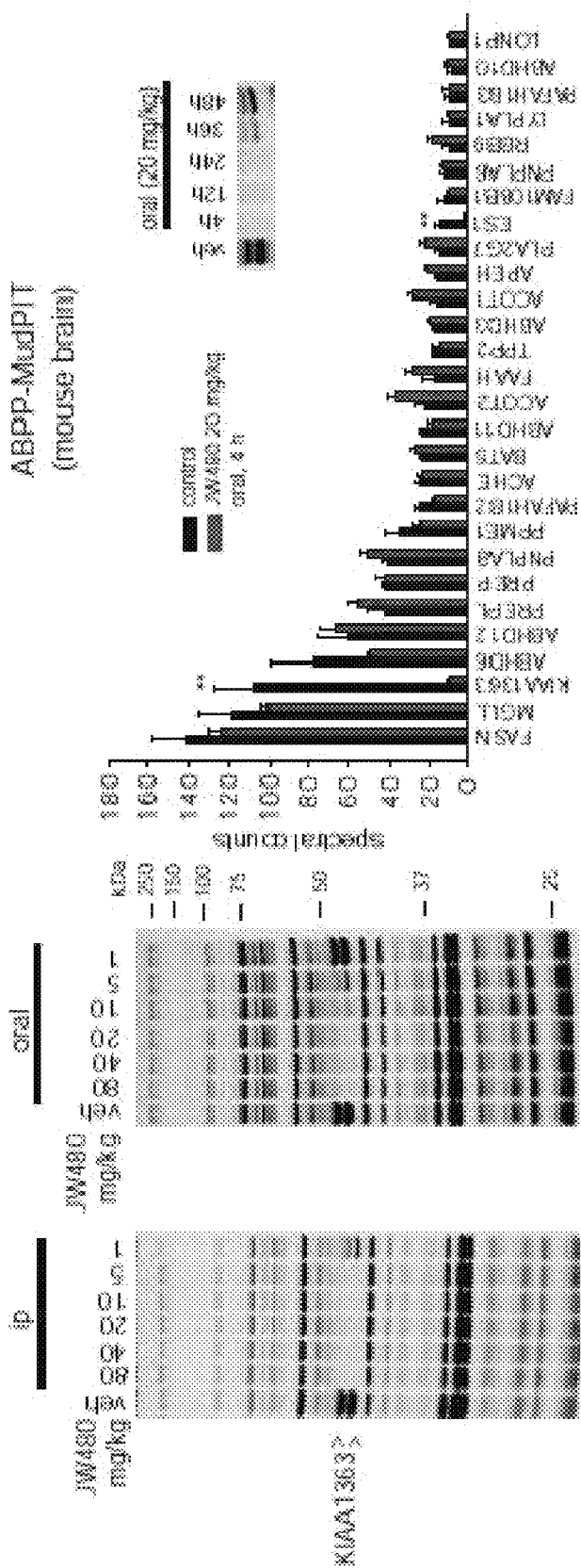

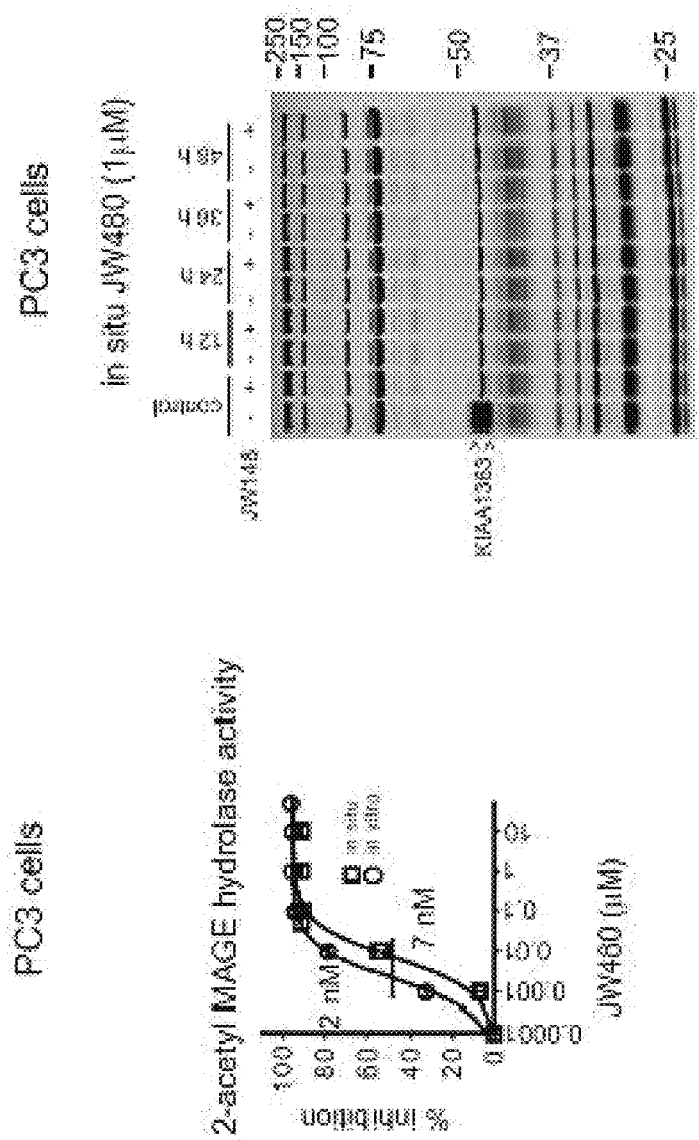

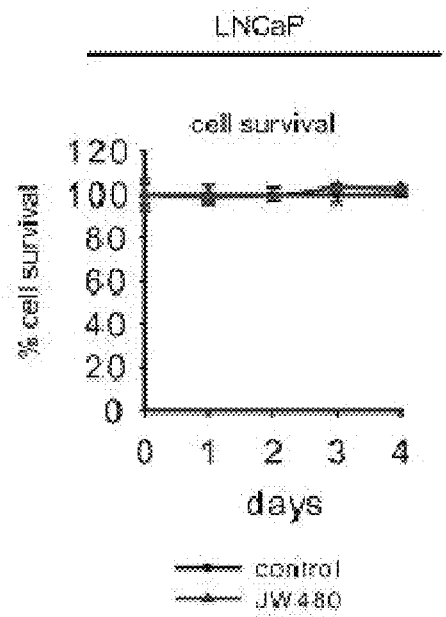
*Fig.12E*
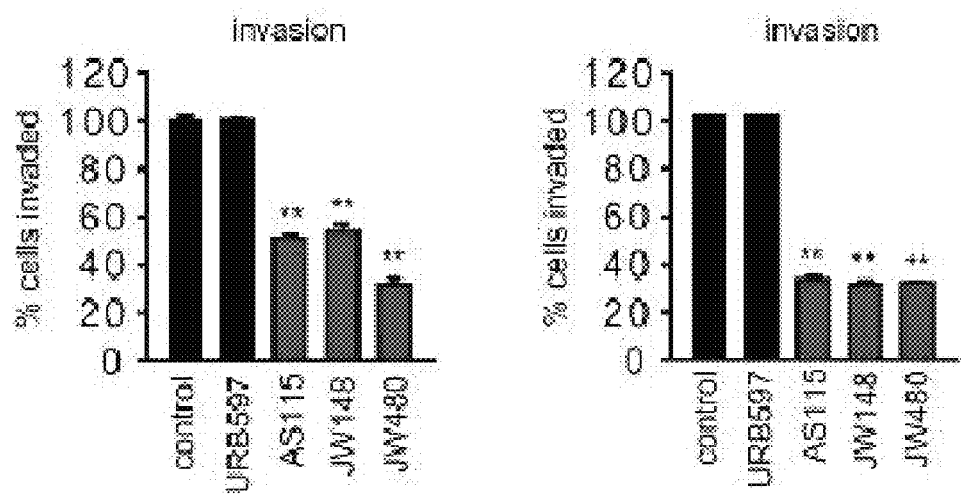
*Fig.12F*  *Fig.12G*

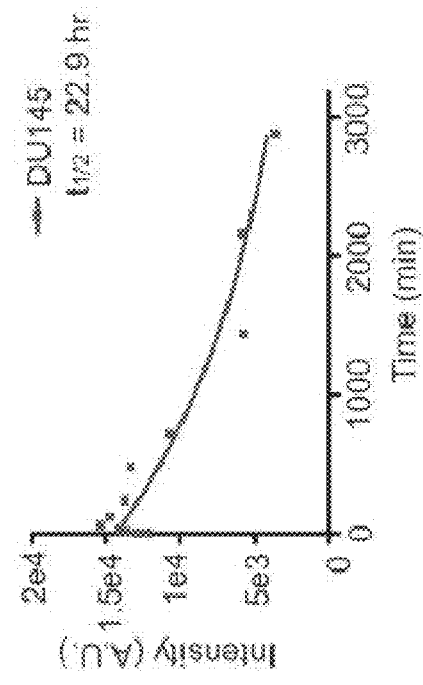
Fig. 15A
Fig. 15B
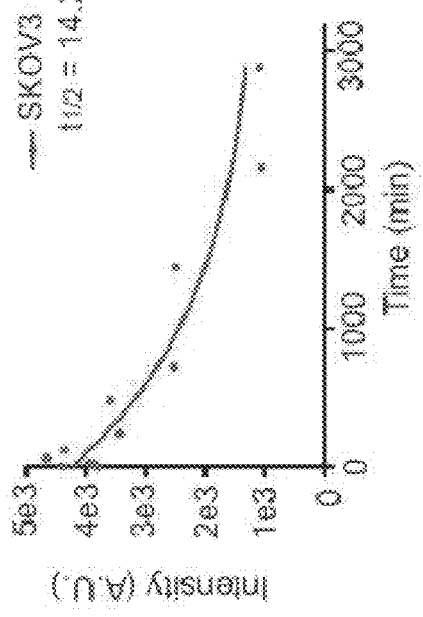
Fig. 15C
Fig. 15D

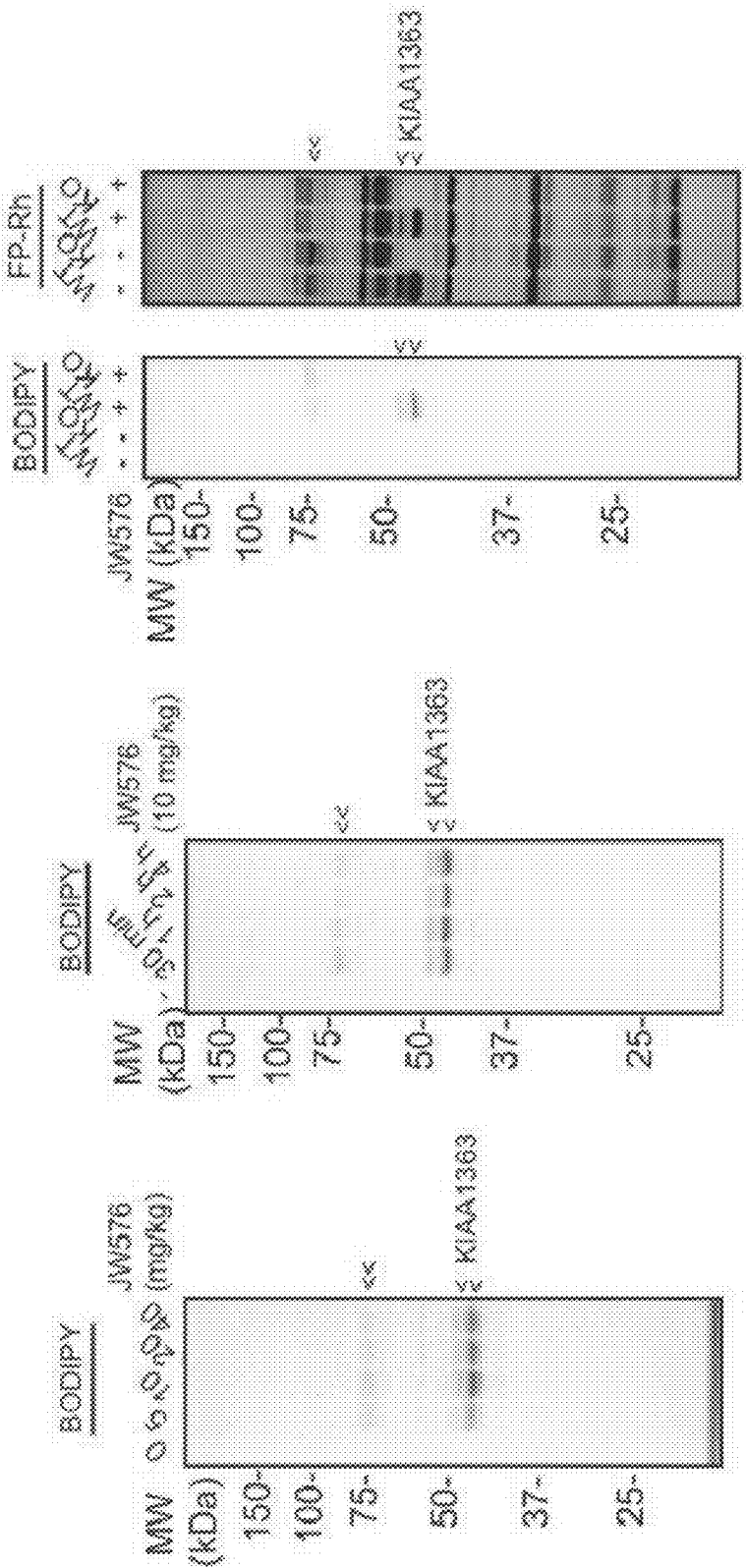

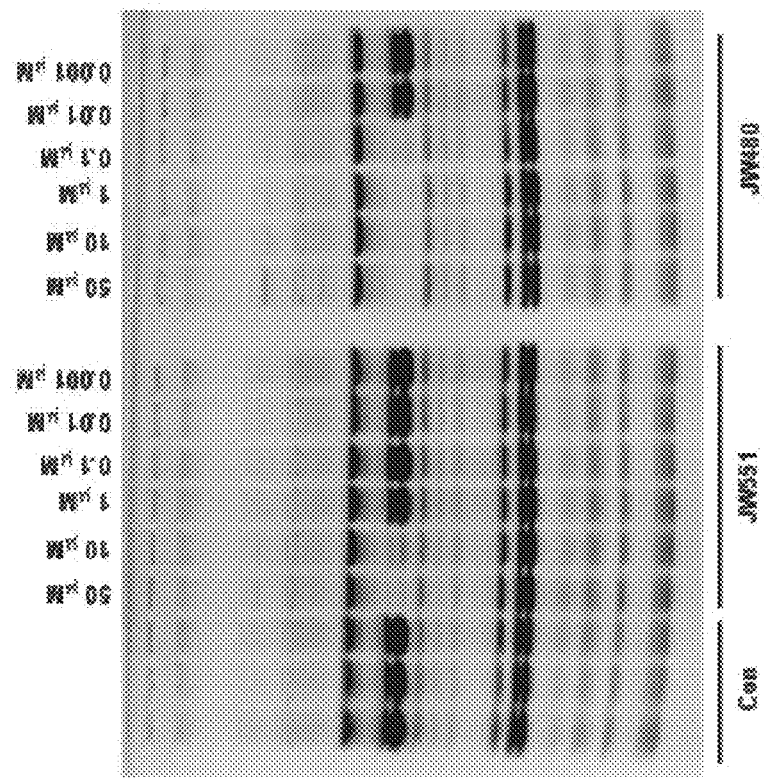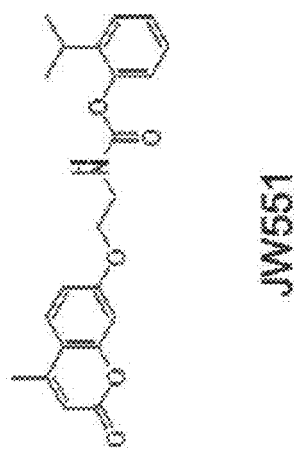
Fig. 17

ANTI-CANCER SERINE HYDROLASE INHIBITORY CARBAMATES

CROSS-REFERENCE TO RELATED APPLICATIONS

This application is a national stage application under 35 U.S.C. §371 of PCT/US2011/057321, filed Oct. 21, 2011, and published as WO 2012/058115 A2 on May 3, 2012, which claims the priority of U.S. Ser. No. 61/407,732, filed Oct. 28, 2010, and of U.S. Ser. No. 61/479,472, filed Apr. 27, 2011, which applications and publication are incorporated by reference as if reproduced herein and made a part hereof in their entirety, and the benefit of priority of each of which is claimed herein.

STATEMENT OF GOVERNMENT SUPPORT

This invention was made with government support under Grant Nos. CA087660, CA132630, DA025285, DA030908 and GM090294 awarded by the National Institutes of Health. The Government has certain rights in this invention.

BACKGROUND

A major challenge facing biological researchers in the 21$^{st}$ century is the functional characterization of the large number of unannotated gene products identified by genome sequencing efforts. Many proteins partly or completely uncharacterized with respect to their biochemical activities belong to expansive, sequence-related families. Although such membership can inform on the general mechanistic class to which a protein belongs (e.g., enzyme, receptor, channel), it is insufficient to predict specific biochemical and physiological functions, which requires knowledge of substrates, ligands, and interacting biomolecules. On the contrary, membership within a large protein family can even present a barrier to achieving these goals by frustrating the implementation of standard genetic and pharmacological methods to probe protein function. For example, targeted gene disruption of one member of a protein superfamily may result in cellular compensation from other family members.

Problems are also encountered when attempting to develop specific inhibitors and/or ligands for uncharacterized members of large protein families, where at least two major experimental issues must be addressed. First, there is an intrinsic difficulty facing ligand discovery for uncharacterized proteins, which often lack the functional information required to develop high quality assays for compound screening. Second, even with a general screening assay in hand, achieving ligand selectivity for one member of a large protein family presents a major challenge.

Serine hydrolases (SHs) are one of the largest and most diverse enzyme classes in mammals. They play fundamental roles in virtually all physiological processes and are targeted by drugs to treat diseases such as diabetes, obesity, and neurodegenerative disorders. Despite this, we lack biological understanding for most of the 110+ predicted mammalian metabolic SHs, due in large part to a dearth of assays to assess their biochemical activities and a lack of selective inhibitors to probe their function in living systems.

As disclosed in U.S. Provisional Application Ser. No. 61/407,732, filed Oct. 28, 2010, which is incorporated herein by reference in its entirety, certain of the inventors herein have developed library versus library screening techniques based on activity-based probes that allow identification of candidate inhibitors of serine hydrolases for which detailed functions can be largely unknown. As described therein, libraries of carbamates were evaluated versus libraries of serine hydrolases, and specific inhibitors of certain of the serine hydrolases were identified. Investigation of promising inhibitors of physiologically significant serine hydrolases has continued.

For more than 40 years, it has been known that tumor cells show dramatic elevations in their neutral ether lipid (NEL) content. Snyder and colleagues in the 1960s first reported that rodent and human tumors possess significantly higher levels of NELs relative to normal tissue (Snyder and Wood, 1969; Wood and Snyder, 1967). This finding has been confirmed for a wide range of cancer cells and primary tumors from several tissues of origin (Albert and Anderson, 1977; Lin et al., 1978; Roos and Choppin, 1984). Evidence has also emerged to suggest a pro-tumorigenic function for NELs, including a study where the levels of these lipids were found to correlate closely with tumorigenicity across a panel of mouse fibroblast cell lines (Roos and Choppin, 1984). However, the enzymes responsible for regulating NEL metabolism in cancer cells are, for the most part, poorly understood.

We have recently determined that the previously uncharacterized transmembrane enzyme KIAA1363 (also called AADACL1) controls the production of the monoalkylglycerol ether (MAGE) class of NELs in cancer cells (Chiang et al., 2006). Serine hydrolase KIAA1363 acts as a 2-acetyl MAGE hydrolase (Chiang et al., 2006) and is likely the principal source for this activity in tumor cells, which was originally detected by Snyder's group in the early 1990s (Blank et al., 1990). MAGEs can be further converted by cancer cells into the bioactive lysophospholipids alkyl-lysophosphatidyl choline (alkyl-LPC) and alkyl-lysophosphatidic acid (alkyl-LPA) (Chiang et al., 2006). Stable knockdown of KIAA1363 expression impaired tumor cell migration and tumor growth in vivo, suggesting a potentially key role for this enzyme in promoting cancer pathogenesis. It has also been found that KIAA1363 is highly elevated in aggressive breast, melanoma, ovarian (Chiang et al., 2006; Jessani et al., 2002), and pancreatic (Iacobuzio-Donahue et al., 2002) cancer cells, as well as primary breast (Ferguson et al., 2005; Jessani et al., 2005) and ovarian (Haverty et al., 2009) tumors.

SUMMARY

The present invention is directed in various embodiments to serine hydrolase inhibitory carbamates, to methods of preparing such carbamates, and to methods of using such carbamates, such as for treatment of malconditions for which inhibition of one or more serine hydrolase enzymes is medically indicated. Carbamates of the invention were identified using activity-based protein profiling [ABPP (Berger et al., 2004; Cravatt et al., 2008; Liu et al., 1999)] guided medicinal chemistry study aimed at optimizing inhibitors for the serine hydrolase enzyme KIAA1363 (AADACL1). For example, it is disclosed herein that certain carbamate inhibitors of KIAA1363 thus identified are effective in blocking prostate cancer pathogenesis.

In various embodiments, the invention provides a carbamate compound identified from a library of serine hydrolase inhibitory carbamates selected by library versus library screening of a set of ABPP-identified serine hydrolase enzymes versus a set of candidate carbamates, wherein the library of serine hydrolase enzymes comprises serine hydrolase KIAA1363, and the carbamate compound inhibits KIAA1363.

For example, in various embodiments, the serine hydrolase inhibitory compound can be a carbamate compound of formula (I)

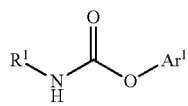

(I)

wherein

—NH—C(=O)O— is a carbamate group for reaction with an active serine residue of the serine hydrolase enzyme;

$Ar^1$ is aryl or heteroaryl, wherein any aryl or heteroaryl can be mono- or independently multi-substituted with J;

$R^1$ is arylalkyl, heterocyclylalkyl, or heteroarylalkyl, wherein any arylalkyl, heterocyclylalkyl, or heteroarylalkyl can be mono- or independently multi-substituted with J; and, J is alkyl, alkenyl, cycloalkyl, heterocyclyl, aryl, heteroaryl, halo, haloalkyl, alkoxy, alkylenedioxy, or haloalkoxy, wherein any J group other than a halo group can be further substituted with one or more independently selected J groups.

In various embodiments, the compound of formula (I) can comprise subgeneric and specific $R^1$ and $Ar^1$ groups as disclosed and claimed herein.

In various embodiments, the invention provides a pharmaceutical composition comprising a compound of the invention and a pharmaceutically acceptable excipient.

In various embodiments, the invention provides a method of inhibiting a serine hydrolase, comprising contacting the hydrolase with an effective amount or concentration of a compound of the invention. A method of inhibiting the serine hydrolase KIAA1363, comprising contacting the hydrolase with an effective amount or concentration of a compound of the invention, for example, compound JW480, is provided.

In various embodiments, the invention provides a method of treating a malcondition in a patent for which inhibition of one or more serine hydrolase enzymes is medically indicated, comprising administering to the patient an effective amount of a compound selected from either of the sets defined above at a frequency and for a duration to provide a beneficial effect to the patient. For example, the malcondition can be cancer, such as prostate cancer.

In various embodiments, the invention provides a method of imaging, in vivo or in vitro, a spatial or temporal distribution, or both, of a serine hydrolase KIAA1363 within a cell or tissue, comprising contacting the cell or tissue with an effective amount or concentration of a carbamate compound of the invention wherein group $R^1$ of formula (I) comprises a fluorophore group, then, examining the cell or tissue under illumination comprising light of an excitation frequency of the fluorophore, such that light of the fluorophore emission spectrum is emitted from a spatial region, or over a period of time, or both, where the serine hydrolase is associated with the fluorophore group. For example, the cell or tissue can be studied using fluorescence microscopy to identify regions where the fluorophore is bound to the serine hydrolase, such as by irreversible acylation of the active serine residue of the hydrolase by the carbamate inhibitor.

BRIEF DESCRIPTION OF THE FIGURES

FIG. 3 shows evidence that JW480 selectively inhibits KIAA1363 in human prostate cancer cells. (A and B) Gel-based competitive ABPP profiles of proteomes from PC3 cells treated with a range of concentrations of JW480 in vitro (A) or in situ (B). The following $IC_{50}$ values, also shown in the figure, were measured for KIAA1363: in vitro: 0.012 μM (95% confidence limits, 0.009-0.014 μM); in situ: 0.006 μM (0.005-0.007 μM). Note that other serine hydrolase activities detected by gel-based ABPP were not affected by JW480. Gels are representative images from n=3. (C) Competitive ABPP-MudPIT results for PC3 cells treated with JW480 (1 μM, 48 hr). Among the ~30 serine hydrolase activities measured by ABPP-MudPIT in whole PC3 cell proteomes, only KIAA1363 was inhibited by JW480. Only serine hydrolases that showed an average spectral count value ≥8 were subjected to quantitative analysis. **p<0.01 for JW480-versus DMSO-treated control groups. Data are presented as means±standard error of the mean (SEM); n=4/group.

FIG. 4 shows evidence that JW480 selectively inhibits KIAA1363 in vivo. (A and B) Gel-based competitive ABPP profiles of brain membrane proteomes from mice treated with a range of doses of JW480 by intraperitoneal (i.p.) (A) or oral (B) administration (4 hr treatment). Note that among the serine hydrolase activities detected by gel-based ABPP, only KIAA1363 was inhibited by JW480. Representative other brain serine hydrolases are marked for comparison. (C) Competitive ABPP-MudPIT results for brain membrane proteomes from mice treated with JW480 (20 mg/kg, oral gavage, 4 hr). Among the ~30 serine hydrolase activities measured by ABPP-MudPIT, only KIAA1363 and the carboxylesterase ES1 were inhibited by JW480. Only serine hydrolases that showed an average spectral count value ≥8 were subjected to quantitative analysis. Inset shows the time course for KIAA1363 inhibition by a single administration of JW480 (20 mg/kg, oral). Gels are representative images from n=3. **p<0.01 for JW480-versus vehicle-treated control groups. Data in (C) are presented as means±standard error of the mean (SEM); n=4/group.

FIG. 15 shows temporal tracking of KIAA1363 turnover with JW576. (A & B) KIAA1363 protein half-life determination in SKOV3 cancer cells was determined by pulsed treatment with JW576 (5 μM, 10 min) Quantification of gel-resolved, labeled KIAA1363 (B) was performed with ImageJ software and fluorescence intensity values were fit to single-phase exponential decay models (A). (C & D) KIAA1363 protein half-life determination in DU145 cells as above in (A & B). Exponential decay curves were generated in Prism 5 software. Data shown are representative of three separate experiments.

FIG. 16 shows evidence that JW576 labels KIAA1363 in vivo. (A) C57BI/6J mice were treated with the indicated doses of JW576 via intraperitoneal injection for 4 hrs, after which animals were sacrificed and heart tissue removed and analyzed for JW576-labeled proteins by in gel-fluorescence scanning. (B) Time-course analysis of heart tissues from C57BI/6J mice treated with JW576 (10 mg/kg) and processed as in (A). (C) Competitive ABPP of heart proteomes from KIAA1363-wild type (WT) and knockout (KO) mice treated with JW576 (10 mg/kg, 1 hr). Scanning on BODIPY (left) and FP-Rh (right) channels confirmed selective labeling of KIAA1363 by JW576 in vivo. Single and double arrows in (A-C) mark JW576-labeled KIAA1363 and an off-target serine hydrolase (likely ES1), respectively.

FIG. 17 shows evidence that the coumain-based fluorescent carbamate inhibitor JW551 inhibits FP-rhodamine labeling of KIAA1363 selectively over other serine hydrolase enzymes with a low micromolar $IC_{50}$.

DETAILED DESCRIPTION

Definitions

Figure 1A:
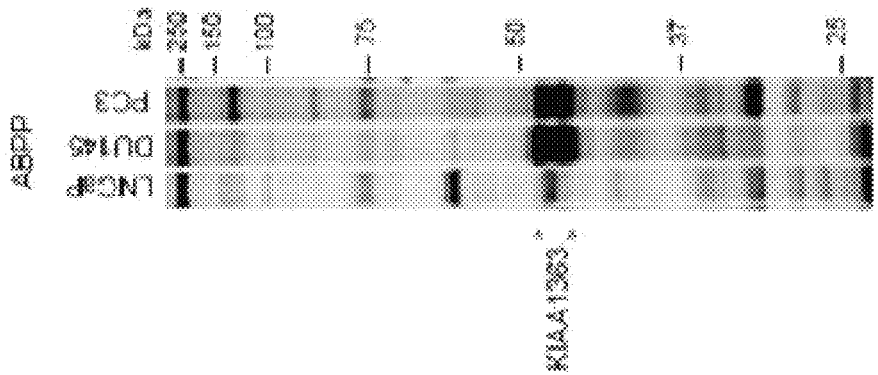
FIG. 1 shows evidence that KIAA1363 is elevated in androgen-independent human prostate cancer cell lines: (A) ABPP of serine hydrolase activities in the androgen-dependent LNCaP and androgen-independent PC3 and DU145 cells line. Serine hydrolase activities were labeled in whole cell proteomes with the activity-based probe FP-rhodamine (1 μM, 30 min) (Jessani et al., 2002; Patricelli et al., 2001) and detected by SDS-PAGE and in-gel fluorescence scanning (fluorescent gel shown in grayscale). KIAA1363 activity is much higher in PC3 and DU145 cells compared to LNCaP cells. Note that KIAA1363 migrates as two distinct glycoforms in cancer cells, as described previously (Chiang et al., 2006; Jessani et al., 2002). (B) PC3 and DU145 cells also show much higher 2-acetyl MAGE hydrolytic activity catalytic compared to LNCaP cells. Note that virtually all 2-acetyl MAGE hydrolase activity in prostate cancer cells is eliminated by the KIAA1363 inhibitor AS115 (10 μM, 4 h treatment, in situ). (C and D) PC3 and DU145 cells show elevated migratory (C) and invasive (D) activity compared to LNCaP cells. (E) PC3 and DU145 cells have much higher levels of MAGEs (C16:0, 1-O-palmityl MAGE; C18:0, 1-O-stearyl MAGE; C18:1 1-O-oleyl MAGE) compared to LNCaP cells. **$p<0.01$ for comparisons between PC3 and DU145 cells versus LNCaP cells. Data are presented as means±standard error of the mean (SEM); n=4-5/group.

As used in the specification and the appended claims, the singular forms "a," "an" and "the" include plural referents unless the context clearly dictates otherwise.

The term "about" as used herein, when referring to a numerical value or range, allows for a degree of variability in the value or range, for example, within 10%, or within 5% of a stated value or of a stated limit of a range.

All percent compositions are given as weight-percentages, unless otherwise stated.

All average molecular weights of polymers are weight-average molecular weights, unless otherwise specified.

As used herein, "individual" (as in the subject of the treatment) means both mammals and non-mammals. Mammals include, for example, humans; non-human primates, e.g. apes and monkeys; and non-primates, e.g. dogs, cats, cattle, horses, sheep, and goats. Non-mammals include, for example, fish and birds.

The term "disease" or "disorder" or "malcondition" are used interchangeably, and are used to refer to diseases or conditions wherein a serine hydrolase plays a role in the biochemical mechanisms involved in the disease or malcondition such that a therapeutically beneficial effect can be achieved by acting on a serine hydrolase. "Acting on" a serine hydrolase can include binding to a serine hydrolase and/or inhibiting the bioactivity of a serine hydrolase.

The expression "effective amount", when used to describe therapy to an individual suffering from a disorder, refers to the amount of a compound of the invention that is effective to inhibit or otherwise act on a serine hydrolase in the individual's tissues wherein a serine hydrolase involved in the disorder is active, wherein such inhibition or other action occurs to an extent sufficient to produce a beneficial therapeutic effect.

A "serine hydrolase" as the term is used herein refers to an enzyme that catalyzes a hydrolytic reaction of an ester or an amide bond, or a similar carbonyl-containing bond such as a thioester, a carbamate or a urea bond, wherein the active site of the enzyme comprises a serine residue. In many if not all cases, the hydroxyl group of the serine residue acts as an enzymic nucleophile that can form a covalent adduct, or a transient complex, with the carbonyl group of the ester or amide during the course of the hydrolytic cleavage reaction catalyzed by the enzyme.

"Substantially" as the term is used herein means completely or almost completely; for example, a composition that is "substantially free" of a component either has none of the component or contains such a trace amount that any relevant functional property of the composition is unaffected by the presence of the trace amount, or a compound is "substantially pure" is there are only negligible traces of impurities present.

"Treating" or "treatment" within the meaning herein refers to an alleviation of symptoms associated with a disorder or disease, or inhibition of further progression or worsening of those symptoms, or prevention or prophylaxis of the disease or disorder, or curing the disease or disorder. Similarly, as used herein, an "effective amount" or a "therapeutically effective amount" of a compound of the invention refers to an amount of the compound that alleviates, in whole or in part, symptoms associated with the disorder or condition, or halts or slows further progression or worsening of those symptoms, or prevents or provides prophylaxis for the disorder or condition. In particular, a "therapeutically effective amount" refers to an amount effective, at dosages and for periods of time necessary, to achieve the desired therapeutic result. A therapeutically effective amount is also one in which any toxic or detrimental effects of compounds of the invention are outweighed by the therapeutically beneficial effects.

By "chemically feasible" is meant a bonding arrangement or a compound where the generally understood rules of organic structure are not violated; for example a structure within a definition of a claim that would contain in certain situations a pentavalent carbon atom that would not exist in nature would be understood to not be within the claim. The structures disclosed herein, in all of their embodiments are intended to include only "chemically feasible" structures, and any recited structures that are not chemically feasible, for example in a structure shown with variable atoms or groups, are not intended to be disclosed or claimed herein.

When a substituent is specified to be an atom or atoms of specified identity, "or a bond", a configuration is referred to when the substituent is "a bond" that the groups that are immediately adjacent to the specified substituent are directly connected to each other in a chemically feasible bonding configuration.

All chiral, diastereomeric, racemic forms of a structure are intended, unless a particular stereochemistry or isomeric form is specifically indicated. Compounds used in the present invention can include enriched or resolved optical isomers at any or all asymmetric atoms as are apparent from the depictions, at any degree of enrichment. Both racemic and diastereomeric mixtures, as well as the individual optical isomers can be isolated or synthesized so as to be substantially free of their enantiomeric or diastereomeric partners, and these are all within the scope of the invention.

The inclusion of an isotopic form of one or more atoms in a molecule that is different from the naturally occurring isotopic distribution of the atom in nature is referred to as an "isotopically labeled form" of the molecule. All isotopic forms of atoms are included as options in the composition of any molecule, unless a specific isotopic form of an atom is indicated. For example, any hydrogen atom or set thereof in a molecule can be any of the isotopic forms of hydrogen, i.e., protium ($^1H$), deuterium ($^2H$), or tritium ($^3H$) in any combination. Similarly, any carbon atom or set thereof in a molecule can be any of the isotopic form of carbons, such as $^{11}C$, $^{12}C$, $^{13}C$, or $^{14}C$, or any nitrogen atom or set thereof in a molecule can be any of the isotopic forms of nitrogen, such as $^{13}N$, $^{14}N$, or $^{15}N$. A molecule can include any combination of isotopic forms in the component atoms making up the molecule, the isotopic form of every atom forming the molecule being independently selected. In a multi-molecular sample of a compound, not every individual molecule necessarily has the same isotopic composition. For example, a sample of a compound can include molecules containing various different isotopic compositions, such as in a tritium or $^{14}C$ radiolabeled sample where only some fraction of the set of molecules making up the macroscopic sample contains a radioactive atom. It is also understood that many elements that are not artificially isotopically enriched themselves are mixtures of naturally occurring isotopic forms, such as $^{14}N$ and $^{15}N$, $^{32}S$ and $^{34}S$, and so forth. A molecule as recited herein is defined as including isotopic forms of all its constituent elements at each position in the molecule. As is well known in the art, isotopically labeled compounds can be prepared by the usual methods of chemical synthesis, except substituting an isotopically labeled precursor molecule. The isotopes, radiolabeled or stable, can be obtained by any method known in the art, such as generation by neutron absorption of a precursor nuclide in a nuclear reactor, by cyclotron reactions, or by isotopic separation such as by mass spectrometry. The isotopic forms are incorporated into precursors as required for use in any particular synthetic route. For example, $^{14}C$ and $^3H$ can be prepared using neutrons generated in a nuclear reactor. Following nuclear transformation, $^{14}C$ and $^3H$ are incorporated into precursor molecules, followed by further elaboration as needed.

The term "amino protecting group" or "N-protected" as used herein refers to those groups intended to protect an amino group against undesirable reactions during synthetic procedures and which can later be removed to reveal the amine. Commonly used amino protecting groups are disclosed in Protective Groups in Organic Synthesis, Greene, T. W.; Wuts, P. G. M., John Wiley & Sons, New York, N.Y., (3rd Edition, 1999). Amino protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; alkoxy- or aryloxy-carbonyl groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. Amine protecting groups also include cyclic amino protecting groups such as phthaloyl and dithiosuccinimidyl, which incorporate the amino nitrogen into a heterocycle. Typically, amino protecting groups include formyl, acetyl, benzoyl, pivaloyl, t-butylacetyl, phenylsulfonyl, Alloc, Teoc, benzyl, Fmoc, Boc and Cbz. It is well within the skill of the ordinary artisan to select and use the appropriate amino protecting group for the synthetic task at hand.

The term "hydroxyl protecting group" or "O-protected" as used herein refers to those groups intended to protect an OH group against undesirable reactions during synthetic procedures and which can later be removed to reveal the amine. Commonly used hydroxyl protecting groups are disclosed in Protective Groups in Organic Synthesis, Greene, T. W.; Wuts, P. G. M., John Wiley & Sons, New York, N.Y., (3rd Edition, 1999). Hydroxyl protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; acyloxy groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. It is well within the skill of the ordinary artisan to select and use the appropriate hydroxyl protecting group for the synthetic task at hand.

In general, "substituted" refers to an organic group as defined herein in which one or more bonds to a hydrogen atom contained therein are replaced by one or more bonds to a non-hydrogen atom such as, but not limited to, a halogen (i.e., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR', OC(O)N(R')$_2$, CN, NO, NO$_2$, ONO$_2$, azido, CF$_3$, OCF$_3$, R', O (oxo), S (thiono), C(O), S(O), methylenedioxy, ethylenedioxy, N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, $(CH_2)_{0-2}N(R')C(O)R'$, $(CH_2)_{0-2}N(R')N(R')_2$, $N(R')N(R')C(O)R'$, $N(R')N(R')C(O)OR'$, $N(R')N(R')CON(R')_2$, $N(R')SO_2R'$, $N(R')SO_2N(R')_2$, $N(R')C(O)OR'$, $N(R')C(O)R'$, $N(R')C(S)R'$, $N(R')C(O)N(R')_2$, $N(R')C(S)N(R')_2$, $N(COR')COR'$, $N(OR')R'$, $C(=NH)N(R')_2$, $C(O)N(OR')R'$, or $C(=NOR')R'$ wherein R' can be hydrogen or a carbon-based moiety, and wherein the carbon-based moiety can itself be further substituted.

When a substituent is monovalent, such as, for example, F or Cl, it is bonded to the atom it is substituting by a single bond. When a substituent is more than monovalent, such as O, which is divalent, it can be bonded to the atom it is substituting by more than one bond, i.e., a divalent substituent is bonded by a double bond; for example, a C substituted with O forms a carbonyl group, C=O, which can also be written as "CO", "C(O)", or "C(=O)", wherein the C and the O are double bonded. When a carbon atom is substituted with a double-bonded oxygen (=O) group, the oxygen substituent is termed an "oxo" group. When a divalent substituent such as NR is double-bonded to a carbon atom, the resulting C(=NR) group is termed an "imino" group. When a divalent substituent such as S is double-bonded to a carbon atom, the results C(=S) group is termed a "thiocarbonyl" group.

Alternatively, a divalent substituent such as O, S, C(O), S(O), or S(O)$_2$ can be connected by two single bonds to two different carbon atoms. For example, O, a divalent substituent, can be bonded to each of two adjacent carbon atoms to provide an epoxide group, or the O can form a bridging ether group, termed an "oxy" group, between adjacent or non-adjacent carbon atoms, for example bridging the 1,4-carbons of a cyclohexyl group to form a [2.2.1]-oxabicyclo system. Further, any substituent can be bonded to a carbon or other atom by a linker, such as $(CH_2)_n$ or $(CR'_2)_n$ wherein n is 1, 2, 3, or more, and each R' is independently selected.

C(O) and S(O)$_2$ groups can be bound to one or two heteroatoms, such as nitrogen, rather than to a carbon atom. For example, when a C(O) group is bound to one carbon and one nitrogen atom, the resulting group is called an "amide" or "carboxamide." When a C(O) group is bound to two nitrogen atoms, the functional group is termed a urea. When a S(O)$_2$ group is bound to one carbon and one nitrogen atom, the resulting unit is termed a "sulfonamide." When a S(O)$_2$ group is bound to two nitrogen atoms, the resulting unit is termed a "sulfamate."

Substituted alkyl, alkenyl, alkynyl, cycloalkyl, and cycloalkenyl groups as well as other substituted groups also include groups in which one or more bonds to a hydrogen atom are replaced by one or more bonds, including double or triple bonds, to a carbon atom, or to a heteroatom such as, but not limited to, oxygen in carbonyl (oxo), carboxyl, ester, amide, imide, urethane, and urea groups; and nitrogen in imines, hydroxyimines, oximes, hydrazones, amidines, guanidines, and nitriles.

Substituted ring groups such as substituted cycloalkyl, aryl, heterocyclyl and heteroaryl groups also include rings and fused ring systems in which a bond to a hydrogen atom is replaced with a bond to a carbon atom. Therefore, substituted cycloalkyl, aryl, heterocyclyl and heteroaryl groups can also be substituted with alkyl, alkenyl, and alkynyl groups as defined herein.

By a "ring system" as the term is used herein is meant a moiety comprising one, two, three or more rings, which can be substituted with non-ring groups or with other ring systems, or both, which can be fully saturated, partially unsaturated, fully unsaturated, or aromatic, and when the ring system includes more than a single ring, the rings can be fused, bridging, or spirocyclic. By "spirocyclic" is meant the class of structures wherein two rings are fused at a single tetrahedral carbon atom, as is well known in the art.

As to any of the groups described herein, which contain one or more substituents, it is understood, of course, that such groups do not contain any substitution or substitution patterns which are sterically impractical and/or synthetically non-feasible. In addition, the compounds of this disclosed subject matter include all stereochemical isomers arising from the substitution of these compounds.

Selected substituents within the compounds described herein are present to a recursive degree. In this context, "recursive substituent" means that a substituent may recite another instance of itself or of another substituent that itself recites the first substituent. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by of example and not limitation, physical properties such as molecular weight, solubility or log P, application properties such as activity against the intended target, and practical properties such as ease of synthesis.

Recursive substituents are an intended aspect of the disclosed subject matter. One of ordinary skill in the art of medicinal and organic chemistry understands the versatility of such substituents. To the degree that recursive substituents are present in a claim of the disclosed subject matter, the total number should be determined as set forth above.

Alkyl groups include straight chain and branched alkyl groups and cycloalkyl groups having from 1 to about 20 carbon atoms, and typically from 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed above, for example, amino, hydroxy, cyano, carboxy, nitro, thio, alkoxy, and halogen groups.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups can be mono-substituted or substituted more than once, such as, but not limited to, 2,2-, 2,3-, 2,4- 2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

The terms "carbocyclic," "carbocyclyl," and "carbocycle" denote a ring structure wherein the atoms of the ring are carbon, such as a cycloalkyl group or an aryl group. In some embodiments, the carbocycle has 3 to 8 ring members, whereas in other embodiments the number of ring carbon atoms is 4, 5, 6, or 7. Unless specifically indicated to the contrary, the carbocyclic ring can be substituted with as many as N−1 substituents wherein N is the size of the carbocyclic ring with, for example, alkyl, alkenyl, alkynyl, amino, aryl, hydroxy, cyano, carboxy, heteroaryl, heterocyclyl, nitro, thio, alkoxy, and halogen groups, or other groups as are listed above. A carbocyclyl ring can be a cycloalkyl ring, a cycloalkenyl ring, or an aryl ring. A carbocyclyl can be monocyclic or polycyclic, and if polycyclic each ring can be independently be a cycloalkyl ring, a cycloalkenyl ring, or an aryl ring.

(Cycloalkyl)alkyl groups, also denoted cycloalkylalkyl, are alkyl groups as defined above in which a hydrogen or carbon bond of the alkyl group is replaced with a bond to a cycloalkyl group as defined above.

Alkenyl groups include straight and branched chain and cyclic alkyl groups as defined above, except that at least one double bond exists between two carbon atoms. Thus, alkenyl groups have from 2 to about 20 carbon atoms, and typically from 2 to 12 carbons or, in some embodiments, from 2 to 8 carbon atoms. Examples include, but are not limited to vinyl, —CH=CH($CH_3$), —CH=C($CH_3$)$_2$, —C($CH_3$)=$CH_2$, —C($CH_3$)=CH($CH_3$), —C($CH_2CH_3$)=$CH_2$, cyclohexenyl, cyclopentenyl, cyclohexadienyl, butadienyl, pentadienyl, and hexadienyl among others.

Cycloalkenyl groups include cycloalkyl groups having at least one double bond between 2 carbons. Thus for example, cycloalkenyl groups include but are not limited to cyclohexenyl, cyclopentenyl, and cyclohexadienyl groups. Cycloalkenyl groups can have from 3 to about 8-12 ring members, whereas in other embodiments the number of ring carbon atoms range from 3 to 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like, provided they include at least one double bond within a ring. Cycloalkenyl groups also include rings that are substituted with straight or branched chain alkyl groups as defined above.

(Cycloalkenyl)alkyl groups are alkyl groups as defined above in which a hydrogen or carbon bond of the alkyl group is replaced with a bond to a cycloalkenyl group as defined above.

Alkynyl groups include straight and branched chain alkyl groups, except that at least one triple bond exists between two carbon atoms. Thus, alkynyl groups have from 2 to about 20 carbon atoms, and typically from 2 to 12 carbons or, in some embodiments, from 2 to 8 carbon atoms. Examples include, but are not limited to —C≡CH, —C≡C($CH_3$), —C≡C($CH_2CH_3$), —$CH_2$C≡CH, —$CH_2$C≡C($CH_3$), and —$CH_2$C≡C($CH_2CH_3$) among others.

The term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—$CH_2$—$CH_2$—$CH_3$, —$CH_2$—$CH_2CH_2$—OH, —$CH_2$—$CH_2$—NH—$CH_3$, —$CH_2$—S—$CH_2$—$CH_3$, —$CH_2CH_2$—S(=O)—$CH_3$, and —$CH_2CH_2$—O—$CH_2CH_2$—O—$CH_3$. Up to two heteroatoms may be consecutive, such as, for example, —$CH_2$—NH—$OCH_3$, or —$CH_2$—$CH_2$—S—S—$CH_3$.

A "cycloheteroalkyl" ring is a cycloalkyl ring containing at least one heteroatom. A cycloheteroalkyl ring can also be termed a "heterocyclyl," described below.

The term "heteroalkenyl" by itself or in combination with another term means, unless otherwise stated, a stable straight or branched chain monounsaturated or di-unsaturated hydrocarbon group consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH=CH—O—$CH_3$, —CH=CH—$CH_2$—OH, —$CH_2$—CH=N—$OCH_3$, —CH=CH—N($CH_3$)—$CH_3$, —$CH_2$—CH=CH—$CH_2$—SH, and —CH=CH—O—$CH_2CH_2$—O—$CH_3$.

Aryl groups are cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined above. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed above.

Aralkyl groups are alkyl groups as defined above in which a hydrogen or carbon bond of an alkyl group is replaced with a bond to an aryl group as defined above. Representative aralkyl groups include benzyl and phenylethyl groups and fused (cycloalkylaryl)alkyl groups such as 4-ethyl-indanyl. Aralkenyl group are alkenyl groups as defined above in which a hydrogen or carbon bond of an alkyl group is replaced with a bond to an aryl group as defined above.

Heterocyclyl groups or the term "heterocyclyl" includes aromatic and non-aromatic ring compounds containing 3 or more ring members, of which, one or more is a heteroatom such as, but not limited to, N, O, and S. Thus a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms sums up to equal the total number of ring atoms. A heterocyclyl ring can also include one or more double bonds. A heteroaryl ring is an embodiment of a heterocyclyl group. The phrase "heterocyclyl group" includes fused ring species including those comprising fused aromatic and non-aromatic groups. For example, a dioxolanyl ring and a benzdioxolanyl ring system (methylenedioxyphenyl ring system) are both heterocyclyl groups within the meaning herein. The phrase also includes polycyclic ring systems containing a heteroatom such as, but not limited to, quinuclidyl. Heterocyclyl groups can be unsubstituted, or can be substituted as discussed above. Heterocyclyl groups include, but are not limited to, pyrrolidinyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Representative substituted heterocyclyl groups can be mono-substituted or substituted more than once, such as, but not limited to, piperidinyl or quinolinyl groups, which are 2-, 3-, 4-, 5-, or 6-substituted, or disubstituted with groups such as those listed above.

Heteroaryl groups are aromatic ring compounds containing 5 or more ring members, of which, one or more is a heteroatom such as, but not limited to, N, O, and S; for instance, heteroaryl rings can have 5 to about 8-12 ring members. A heteroaryl group is a variety of a heterocyclyl group that possesses an aromatic electronic structure. A heteroaryl group designated as a $C_2$-heteroaryl can be a 5-ring with two carbon atoms and three heteroatoms, a 6-ring with two carbon atoms and four heteroatoms and so forth. Likewise a $C_4$-heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heteroaryl groups can be unsubstituted, or can be substituted with groups as is discussed above. Representative substituted heteroaryl groups can be substituted one or more times with groups such as those listed above.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), and the like.

Heterocyclylalkyl groups are alkyl groups as defined above in which a hydrogen or carbon bond of an alkyl group as defined above is replaced with a bond to a heterocyclyl group as defined above. Representative heterocyclyl alkyl groups include, but are not limited to, furan-2-yl methyl, furan-3-yl methyl, pyridine-3-yl methyl, tetrahydrofuran-2-yl ethyl, and indol-2-yl propyl.

Heteroarylalkyl groups are alkyl groups as defined above in which a hydrogen or carbon bond of an alkyl group is replaced with a bond to a heteroaryl group as defined above.

The term "alkoxy" refers to an oxygen atom connected to an alkyl group, including a cycloalkyl group, as are defined above. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structures are substituted therewith.

The terms "halo" or "halogen" or "halide" by themselves or as part of another substituent mean, unless otherwise stated, a fluorine, chlorine, bromine, or iodine atom, preferably, fluorine, chlorine, or bromine.

A "haloalkyl" group includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

A "haloalkoxy" group includes mono-halo alkoxy groups, poly-halo alkoxy groups wherein all halo atoms can be the same or different, and per-halo alkoxy groups, wherein all hydrogen atoms are replaced by halogen atoms, such as fluoro. Examples of haloalkoxy include trifluoromethoxy, 1,1-dichloroethoxy, 1,2-dichloroethoxy, 1,3-dibromo-3,3-difluoropropoxy, perfluorobutoxy, and the like.

The term "($C_x$-$C_y$)perfluoroalkyl," wherein x<y, means an alkyl group with a minimum of x carbon atoms and a maximum of y carbon atoms, wherein all hydrogen atoms are replaced by fluorine atoms. Preferred is —($C_1$-$C_6$)perfluoroalkyl, more preferred is —($C_1$-$C_3$)perfluoroalkyl, most preferred is —$CF_3$.

The term "($C_x$-$C_y$)perfluoroalkylene," wherein x<y, means an alkyl group with a minimum of x carbon atoms and a maximum of y carbon atoms, wherein all hydrogen atoms are replaced by fluorine atoms. Preferred is —($C_1$-$C_6$)perfluoroalkylene, more preferred is —($C_1$-$C_3$)perfluoroalkylene, most preferred is —$CF_2$—.

The terms "aryloxy" and "arylalkoxy" refer to, respectively, an aryl group bonded to an oxygen atom and an aralkyl group bonded to the oxygen atom at the alkyl moiety. Examples include but are not limited to phenoxy, naphthyloxy, and benzyloxy.

An "acyl" group as the term is used herein refers to a group containing a carbonyl moiety wherein the group is bonded via the carbonyl carbon atom. The carbonyl carbon atom is also bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-20 additional carbon atoms bonded to the carbonyl group. An acyl group can include double or triple bonds within the meaning herein. An acryloyl group is an example of an acyl group. An acyl group can also include heteroatoms within the meaning here. A nicotinoyl group (pyridyl-3-carbonyl) group is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "amine" includes primary, secondary, and tertiary amines having, e.g., the formula N(group)$_3$ wherein each group can independently be H or non-H, such as alkyl, aryl, and the like. Amines include but are not limited to R—$NH_2$, for example, alkylamines, arylamines, alkylarylamines; $R_2$NH wherein each R is independently selected, such as dialkylamines, diarylamines, aralkylamines, heterocyclylamines and the like; and $R_3$N wherein each R is independently selected, such as trialkylamines, dialkylarylamines, alkyldiarylamines, triarylamines, and the like. The term "amine" also includes ammonium ions as used herein.

An "amino" group is a substituent of the form —$NH_2$, —NHR, —$NR_2$, —$NR_3^+$, wherein each R is independently selected, and protonated forms of each, except for —$NR_3^+$, which cannot be protonated. Accordingly, any compound substituted with an amino group can be viewed as an amine. An "amino group" within the meaning herein can be a primary, secondary, tertiary or quaternary amino group. An "alkylamino" group includes a monoalkylamino, dialkylamino, and trialkylamino group.

An "ammonium" ion includes the unsubstituted ammonium ion $NH_4^+$, but unless otherwise specified, it also includes any protonated or quaternarized forms of amines. Thus, trimethylammonium hydrochloride and tetramethylammonium chloride are both ammonium ions, and amines, within the meaning herein.

The term "amide" (or "amido") includes C- and N-amide groups, i.e., —C(O)$NR_2$, and —NRC(O)R groups, respectively. Amide groups therefore include but are not limited to primary carboxamide groups (—C(O)$NH_2$) and formamide groups (—NHC(O)H). A "carboxamido" group is a group of the formula C(O)$NR_2$, wherein R can be H, alkyl, aryl, etc.

The term "azido" refers to an $N_3$ group. An "azide" can be an organic azide or can be a salt of the azide ($N_3^-$) anion. The term "nitro" refers to an $NO_2$ group bonded to an organic moiety. The term "nitroso" refers to an NO group bonded to an organic moiety. The term nitrate refers to an $ONO_2$ group bonded to an organic moiety or to a salt of the nitrate ($NO_3^-$) anion.

The term "urethane" ("carbamoyl" or "carbamyl") includes N- and O-urethane groups, i.e., —NRC(O)OR and —OC(O)$NR_2$ groups, respectively.

The term "sulfonamide" (or "sulfonamido") includes S- and N-sulfonamide groups, i.e., —$SO_2NR_2$ and —NRSO$_2$R groups, respectively. Sulfonamide groups therefore include but are not limited to sulfamoyl groups (—$SO_2NH_2$). An organosulfur structure represented by the formula —S(O)(NR)— is understood to refer to a sulfoximine, wherein both the oxygen and the nitrogen atoms are bonded to the sulfur atom, which is also bonded to two carbon atoms.

The term "amidine" or "amidino" includes groups of the formula —C(NR)$NR_2$. Typically, an amidino group is —C(NH)$NH_2$.

The term "guanidine" or "guanidino" includes groups of the formula —NRC(NR)$NR_2$. Typically, a guanidino group is —NHC(NH)$NH_2$.

A "salt" as is well known in the art includes an organic compound such as a carboxylic acid, a sulfonic acid, or an amine, in ionic form, in combination with a counterion. For example, acids in their anionic form can form salts with cations such as metal cations, for example sodium, potassium, and the like, with ammonium salts such as $NH_4^+$ or the cations of various amines, including tetraalkyl ammonium salts such as tetramethylammonium, or other cations such as trimethylsulfonium, and the like. A "pharmaceutically acceptable" or "pharmacologically acceptable" salt is a salt formed from an ion that has been approved for human consumption and is generally non-toxic, such as a chloride salt or a sodium salt. A "zwitterion" is an internal salt such as can be formed in a molecule that has at least two ionizable groups, one forming an anion and the other a cation, which serve to balance each other. For example, amino acids such as glycine can exist in a zwitterionic form. A "zwitterion" is a salt within the meaning herein. The compounds of the present invention may take the form of salts. The term "salts" embraces addition salts of free acids or free bases which are compounds of the invention. Salts can be "pharmaceutically-acceptable salts." The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, aralipathic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Examples of pharmaceutically unacceptable acid addition salts include, for example, perchlorates and tetrafluoroborates.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. Although pharmaceutically unacceptable salts are not generally useful as medicaments, such salts may be useful, for example as intermediates in the synthesis of Formula (I) compounds, for example in their purification by recrystallization. All of these salts may be prepared by conventional means from the corresponding compound according to Formula (I) by reacting, for example, the appropriate acid or base with the compound according to Formula (I). The term "pharmaceutically acceptable salts" refers to nontoxic inorganic or organic acid and/or base addition salts, see, for example, Lit et al., Salt Selection for Basic Drugs (1986), *Int J. Pharm.*, 33, 201-217, incorporated by reference herein.

A "hydrate" is a compound that exists in a composition with water molecules. The composition can include water in stoichiometic quantities, such as a monohydrate or a dihydrate, or can include water in random amounts. As the term is used herein a "hydrate" refers to a solid form, i.e., a compound in water solution, while it may be hydrated, is not a hydrate as the term is used herein.

A "solvate" is a similar composition except that a solvent other that water replaces the water. For example, methanol or ethanol can form an "alcoholate", which can again be stoichiometric or non-stoichiometric. As the term is used herein a "solvate" refers to a solid form, i.e., a compound in solution in a solvent, while it may be solvated, is not a solvate as the term is used herein.

A "prodrug" as is well known in the art is a substance that can be administered to a patient where the substance is converted in vivo by the action of biochemicals within the patients body, such as enzymes, to the active pharmaceutical ingredient. Examples of prodrugs include esters of carboxylic acid groups, which can be hydrolyzed by endogenous esterases as are found in the bloodstream of humans and other mammals. Conventional procedures for the selection and preparation of suitable prodrug derivatives are described, for example, in "Design of Prodrugs", ed. H. Bundgaard, Elsevier, 1985.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

If a value of a variable that is necessarily an integer, e.g., the number of carbon atoms in an alkyl group or the number of substituents on a ring, is described as a range, e.g., 0-4, what is meant is that the value can be any integer between 0 and 4 inclusive, i.e., 0, 1, 2, 3, or 4.

In various embodiments, the compound or set of compounds, such as are used in the inventive methods, can be any one of any of the combinations and/or sub-combinations of the above-listed embodiments.

In various embodiments, a compound as shown in any of the Examples, or among the exemplary compounds, is provided. Provisos may apply to any of the disclosed categories or embodiments wherein any one or more of the other above disclosed embodiments or species may be excluded from such categories or embodiments.

The present invention further embraces isolated compounds of the invention. The expression "isolated compound" refers to a preparation of a compound of the invention, or a mixture of compounds the invention, wherein the isolated compound has been separated from the reagents used, and/or byproducts formed, in the synthesis of the compound or compounds. "Isolated" does not mean that the preparation is technically pure (homogeneous), but it is sufficiently pure to compound in a form in which it can be used therapeutically. Preferably an "isolated compound" refers to a preparation of a compound of the invention or a mixture of compounds of the invention, which contains the named compound or mixture of compounds of the invention in an amount of at least 10 percent by weight of the total weight. Preferably the preparation contains the named compound or mixture of compounds in an amount of at least 50 percent by weight of the total weight; more preferably at least 80 percent by weight of the total weight; and most preferably at least 90 percent, at least 95 percent or at least 98 percent by weight of the total weight of the preparation.

The compounds of the invention and intermediates may be isolated from their reaction mixtures and purified by standard techniques such as filtration, liquid-liquid extraction, solid phase extraction, distillation, recrystallization or chromatography, including flash column chromatography, or HPLC.

Isomerism and Tautomerism in Compounds of the Invention

Tautomerism

Within the present invention it is to be understood that a compound of the formula (I) or a salt thereof may exhibit the phenomenon of tautomerism whereby two chemical compounds that are capable of facile interconversion by exchanging a hydrogen atom between two atoms, to either of which it forms a covalent bond. Since the tautomeric compounds exist in mobile equilibrium with each other they may be regarded as different isomeric forms of the same compound. It is to be understood that the formulae drawings within this specification can represent only one of the possible tautomeric forms. However, it is also to be understood that the invention encompasses any tautomeric form, and is not to be limited merely to any one tautomeric form utilized within the formulae drawings. The formulae drawings within this specification can represent only one of the possible tautomeric forms and it is to be understood that the specification encompasses all possible tautomeric forms of the compounds drawn not just those forms which it has been convenient to show graphically herein. For example, tautomerism may be exhibited by a pyrazolyl group bonded as indicated by the wavy line. While both substituents would be termed a 4-pyrazolyl group, it is evident that a different nitrogen atom bears the hydrogen atom in each structure.

Such tautomerism can also occur with substituted pyrazoles such as 3-methyl, 5-methyl, or 3,5-dimethylpyrazoles, and the like. Another example of tautomerism is amido-imido (lactam-lactim when cyclic) tautomerism, such as is seen in heterocyclic compounds bearing a ring oxygen atom adjacent to a ring nitrogen atom. For example, the equilibrium:

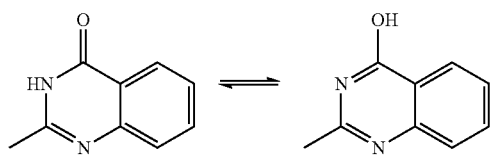

is an example of tautomerism. Accordingly, a structure depicted herein as one tautomer is intended to also include the other tautomer.

Optical Isomerism

It will be understood that when compounds of the present invention contain one or more chiral centers, the compounds may exist in, and may be isolated as pure enantiomeric or diastereomeric forms or as racemic mixtures. The present invention therefore includes any possible enantiomers, diastereomers, racemates or mixtures thereof of the compounds of the invention.

The isomers resulting from the presence of a chiral center comprise a pair of non-superimposable isomers that are called "enantiomers." Single enantiomers of a pure compound are optically active, i.e., they are capable of rotating the plane of plane polarized light. Single enantiomers are designated according to the Cahn-Ingold-Prelog system. The priority of substituents is ranked based on atomic weights, a higher atomic weight, as determined by the systematic procedure, having a higher priority ranking. Once the priority ranking of the four groups is determined, the molecule is oriented so that the lowest ranking group is pointed away from the viewer. Then, if the descending rank order of the other groups proceeds clockwise, the molecule is designated (R) and if the descending rank of the other groups proceeds counterclockwise, the molecule is designated (S). In the example in Scheme 14, the Cahn-Ingold-Prelog ranking is A>B>C>D. The lowest ranking atom, D is oriented away from the viewer.

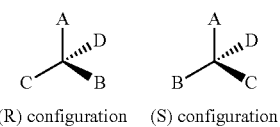

(R) configuration (S) configuration

The present invention is meant to encompass diastereomers as well as their racemic and resolved, diastereomerically and enantiomerically pure forms and salts thereof. Diastereomeric pairs may be resolved by known separation techniques including normal and reverse phase chromatography, and crystallization.

"Isolated optical isomer" means a compound which has been substantially purified from the corresponding optical isomer(s) of the same formula. Preferably, the isolated isomer is at least about 80%, more preferably at least 90% pure, even more preferably at least 98% pure, most preferably at least about 99% pure, by weight.

Isolated optical isomers may be purified from racemic mixtures by well-known chiral separation techniques. According to one such method, a racemic mixture of a compound of the invention, or a chiral intermediate thereof, is separated into 99% wt. % pure optical isomers by HPLC using a suitable chiral column, such as a member of the series of DAICEL® CHIRALPAK® family of columns (Daicel Chemical Industries, Ltd., Tokyo, Japan). The column is operated according to the manufacturer's instructions.

Rotational Isomerism

It is understood that due to chemical properties (i.e., resonance lending some double bond character to the C—N bond) of restricted rotation about the amide bond linkage (as illustrated below) it is possible to observe separate rotamer species and even, under some circumstances, to isolate such species (see below). It is further understood that certain structural elements, including steric bulk or substituents on the amide nitrogen, may enhance the stability of a rotamer to the extent that a compound may be isolated as, and exist indefinitely, as a single stable rotamer. The present invention therefore includes any possible stable rotamers of formula (I) which are biologically active in the treatment of cancer or other proliferative disease states.

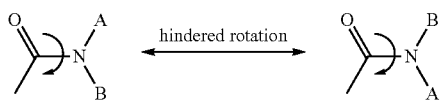

Regioisomerism

The preferred compounds of the present invention have a particular spatial arrangement of substituents on the aromatic rings, which is related to the structure activity relationship demonstrated by the compound class. Often such substitution arrangement is denoted by a numbering system; however, numbering systems are often not consistent between different ring systems. In six-membered aromatic systems, the spatial arrangements are specified by the common nomenclature "para" for 1,4-substitution, "meta" for 1,3-substitution and "ortho" for 1,2-substitution as shown below.

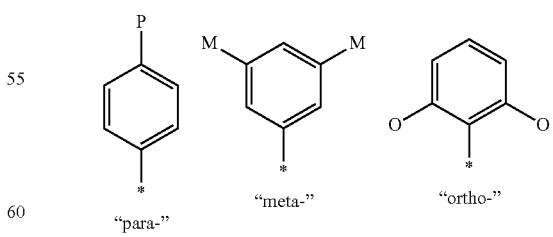

"para-" "meta-" "ortho-"

In various embodiments, the compound or set of compounds, such as are among the inventive compounds or are used in the inventive methods, can be any one of any of the combinations and/or sub-combinations of the above-listed embodiments.

DETAILED DESCRIPTION

The present invention is directed in various embodiments to serine hydrolase inhibitory carbamates, such as KIAA1363-inhibitory carbamates; to methods of preparing such carbamates; and to methods of using such carbamates, such as for treatment of malconditions for which inhibition of one or more serine hydrolase enzymes is medically indicated. An example is the treatment of cancer, such as prostate cancer, through inhibition of the serine hydrolase KIAA1363 with a compound of the invention, or any salt, hydrate, solvate, metabolite, or prodrug thereof.

In various embodiments, the invention provides a carbamate compound identified from a library of serine hydrolase inhibitory carbamates selected by library versus library screening of a set of ABPP-identified serine hydrolase enzymes versus a set of candidate carbamates, wherein the library of serine hydrolase enzymes comprises serine hydrolase KIAA1363, and the carbamate compound inhibits KIAA1363.

The serine hydrolase inhibitory compound can comprise a carbamate compound of formula (I)

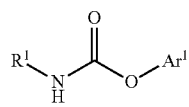

(I)

wherein

—NH—C(=O)O— is a carbamate group for reaction with an active serine residue of the serine hydrolase enzyme;

$Ar^1$ is aryl or heteroaryl, wherein any aryl or heteroaryl can be mono- or independently multi-substituted with J;

$R^1$ is arylalkyl, heterocyclylalkyl, or heteroarylalkyl, wherein any arylalkyl, heterocyclylalkyl, or heteroarylalkyl can be mono- or independently multi-substituted with J; and, J is alkyl, alkenyl, cycloalkyl, heterocyclyl, aryl, heteroaryl, halo, haloalkyl, alkoxy, alkylenedioxy, or haloalkoxy, wherein any J group other than a halo group can be further substituted with one or more independently selected J groups.

In various embodiments, a carbamate of formula (I) of the invention does not include a compound of formula

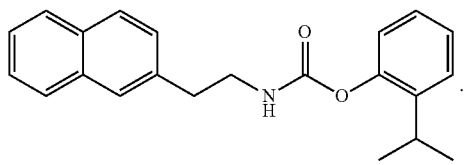 [SMILES: CC(C)c1ccccc1OC(=O)NCCc1ccc2ccccc2c1]

In various embodiments of the carbamate compound of formula (I), the $Ar^1$ can be a group of formula (II)

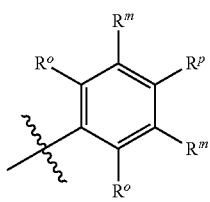

(II)

wherein a wavy line indicates a point of bonding of $Ar^1$ to the carbamate group:

each independently selected $R^o$ is H, alkyl, alkenyl, or alkoxy, each independently selected $R^m$ is H, alkyl, alkoxy, or $NR_2$, $R^p$ is H, alkyl, cycloalkyl, aryl, or heteroaryl; or, an $R^o$ and an adjacent $R^m$ together with the atoms to which they are bonded form a fused heterocyclyl, heteroaryl, cycloalkyl, or aryl ring, any of which is substituted with 0-3 J group; or, an $R^m$ and $R^p$ together with the atoms to which they are bonded form a fused heterocyclyl, heteroaryl, cycloalkyl, or aryl, any of which is substituted with 0-3 J groups; and, R is H or alkyl substituted with 0-3 J groups.

More specifically, the $Ar^1$ group can be a group of any of the following structures

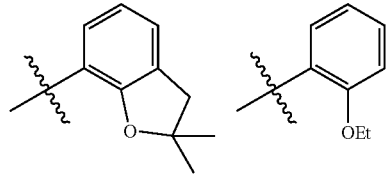

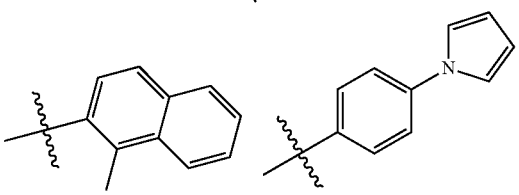

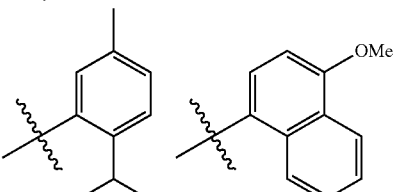

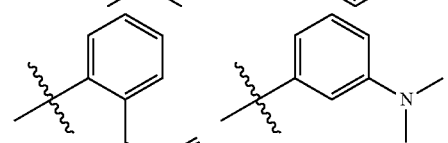

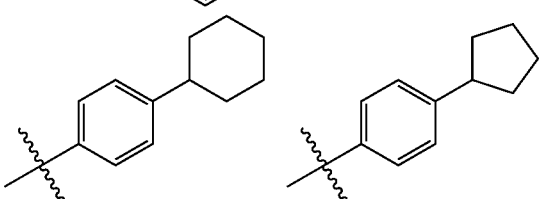

wherein a wavy line indicates a point of attachment.

In various embodiments, a compound of formula (I) of the invention can include an $R^1$ group of formula (IIIA)

(IIIA)

wherein
each independently selected $R^{o1}$ is H or halo;
each independently selected $R^{m1}$ is H, halo, or alkoxy;
$R^{p1}$ is H, halo, alkyl, alkoxy, haloalkyl, haloalkoxy, or aryl; or,
an $R^{o1}$ and an adjacent $R^{m1}$ together with the atoms to which they are bonded form a fused heterocyclyl, heteroaryl, or aryl group, any of which is substituted with 0-3 J group; or,
an $R^{m1}$ and $R^{p1}$ together with the atoms to which they are bonded form a fused heterocyclyl, heteroaryl, or aryl group, any of which is substituted with 0-3 J groups;
or, $R^1$ is a group of formula (IIIB)

(IIIB)

wherein
HA is a monocyclic, bicyclic, or tricyclic heteroaryl or heterocyclyl group substituted with 0-3J;
and,
n is 0, 1, 2, 3, 4, or 5;
each independently selected $R^2$ is H, alkyl, or aryl;

More specifically, $R^1$ can be a substituted or unsubstituted benzyl, phenethyl, phenylpropyl, benzhydrylalkyl, naphthylalkyl, thienylalkyl, indolylalkyl, or morpholinylalkyl group.

In various embodiments, a serine hydrolase carbamate of the invention can be any compound selected from the set consisting of:

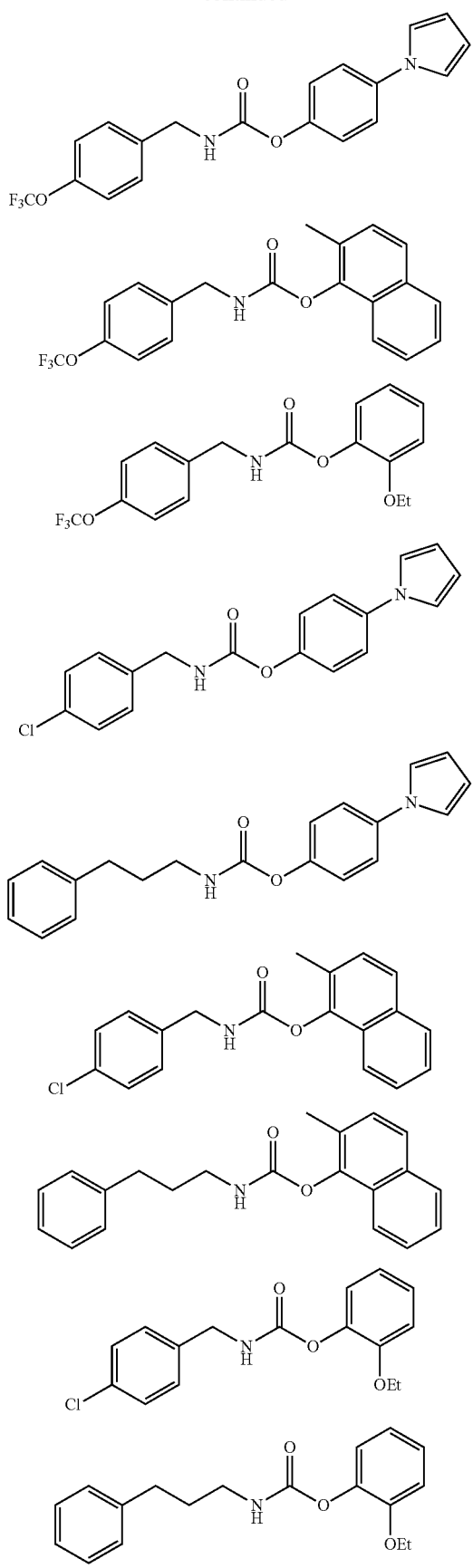
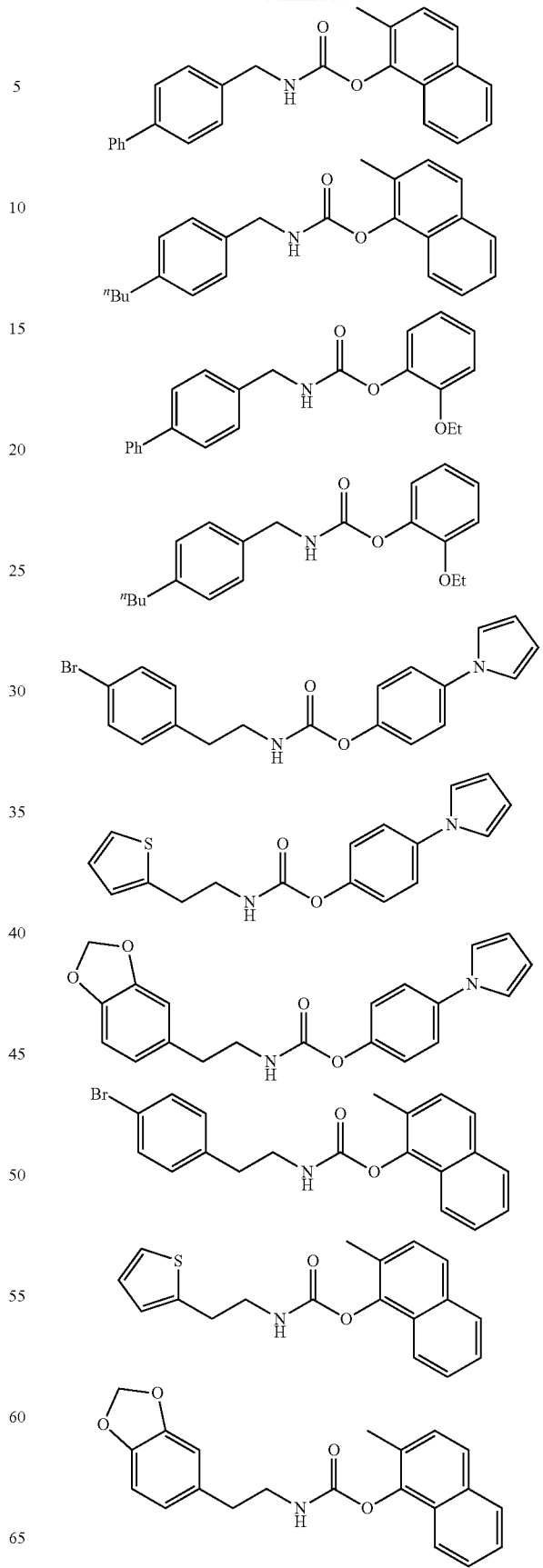

-continued
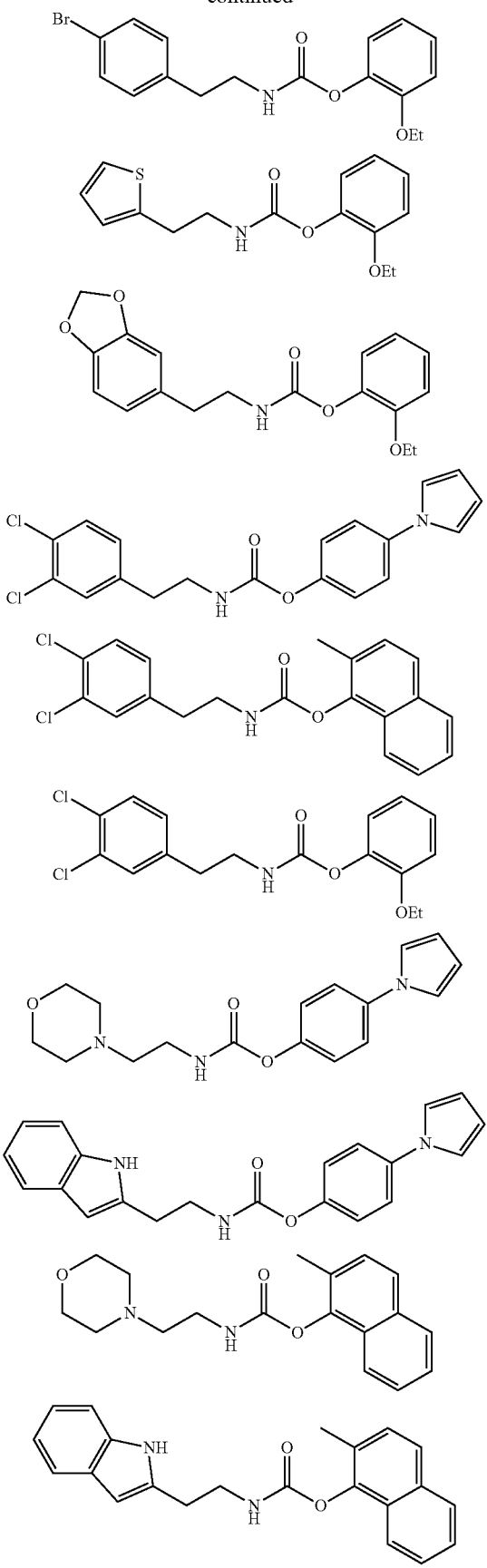
-continued
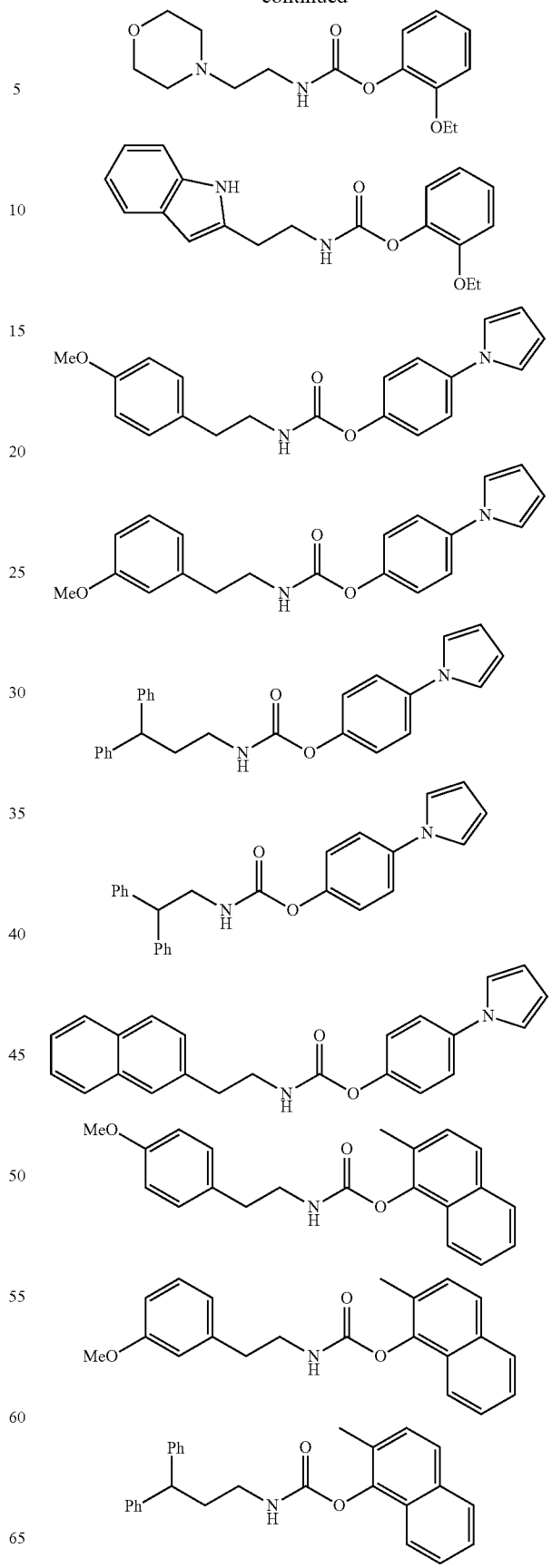

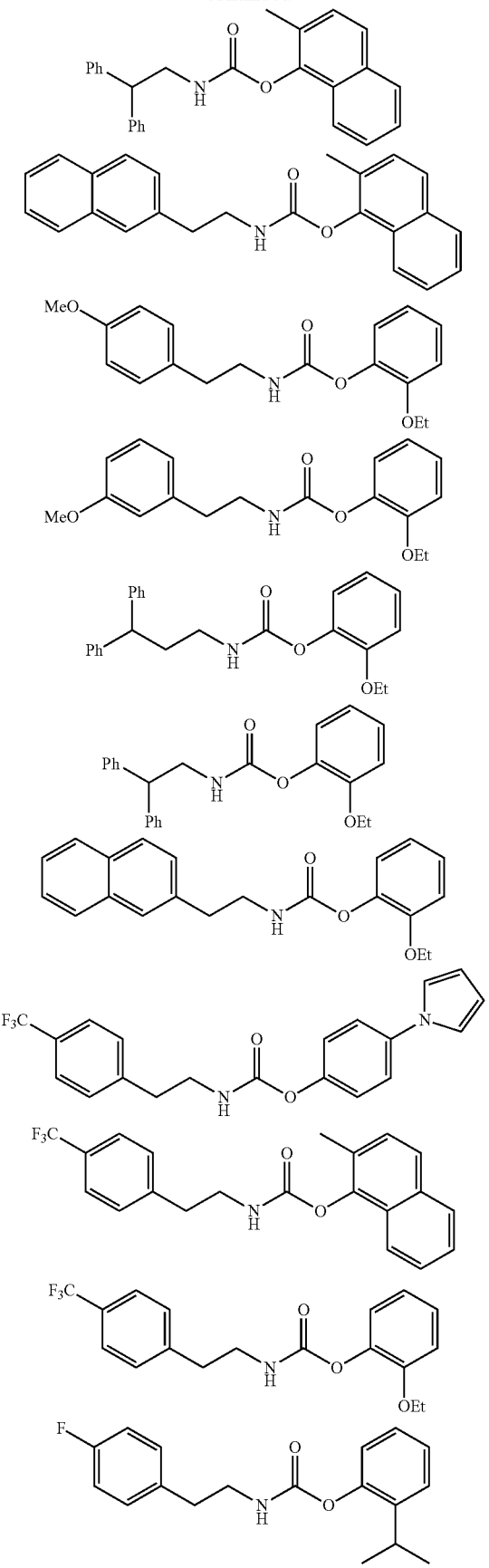
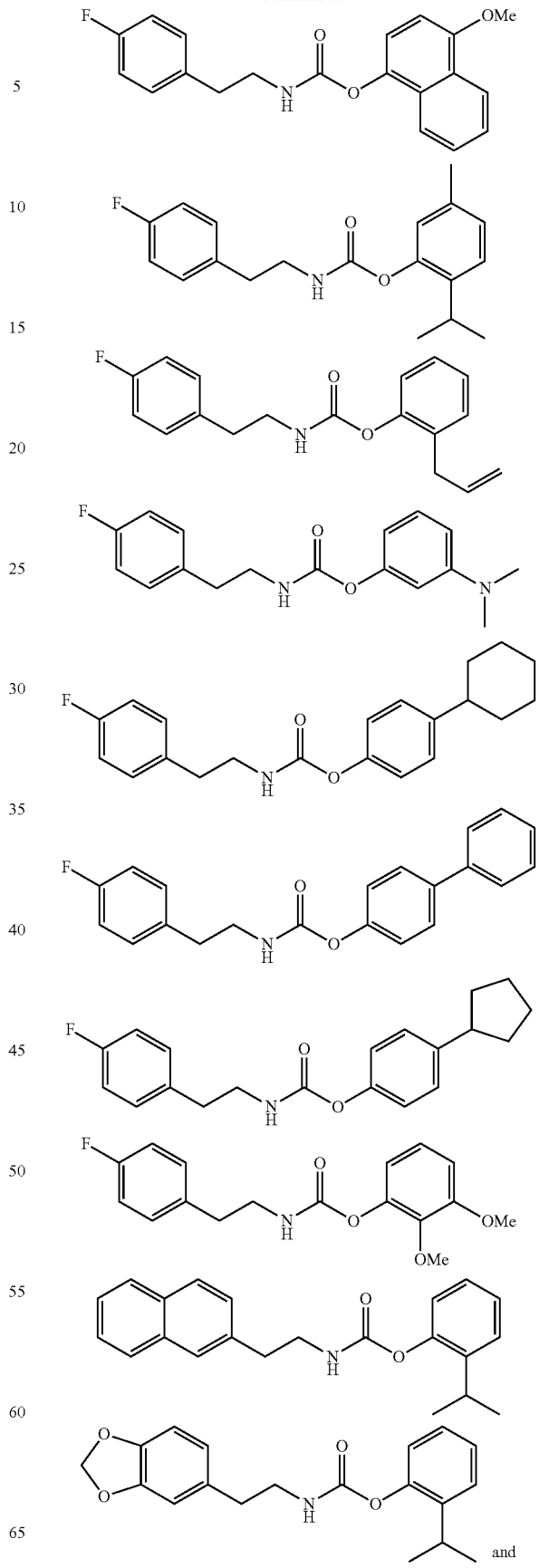

-continued

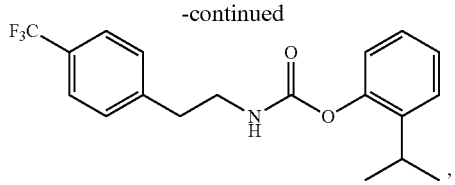

, or a pharmaceutically acceptable salt thereof.

In various embodiments, the invention provides a method of inhibiting a serine hydrolase, comprising contacting the hydrolase with a compound of formula (I), e.g., a compound selected from set of compounds shown in Table 1, below. Table 1 shows the structures of various KIAA1363 inhibitors and their activities. $IC_{50}$ values were derived from ABPP analysis of KIAA1363 activity in mouse brain membrane proteome and are averages of three replicates. Inhibitors were added to the proteome for 30 min before addition of FP-rhodamine (1 µM, 30 min).

Compounds depicted in Table 1, being exemplary of compounds of formula (I) as described above, screened against KIAA1363, revealed that a significant proportion of the compounds had $IC_{50}$ values at micromolar and sub-micromolar concentrations, whereas certain of the compounds were inactive. Among the compounds tested, compounds JW464, JW468. JW480, JW481, and JW482 were found to be the most potent, each having $IC_{50}$ values of around 10 nanomolar. Additionally, compounds JW147, JW148, JW383, JW384, JW389, JW392, JW398, JW413, JW417, JW418, JW422, JW423, JW437, JW440, JW445, JW448, JW466, JW472, and JW473 were all found to have $IC_{50}$ values of less than 1 micromolar.

TABLE 1

KIAA 1363-Inhibitory Carbamates with $IC_{50}$ Values

| | Structure | $IC_{50}$ (µM) |
|---|---|---|
| JW147 | 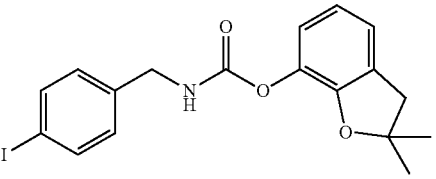 [SMILES: CC1(C)Cc2cccc(OC(=O)NCc3ccc(I)cc3)c2O1] | 0.148 |
| JW148 | 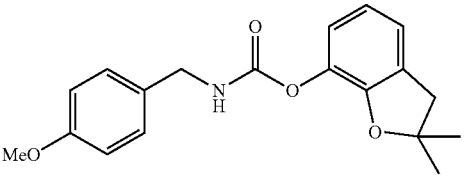 [SMILES: COc1ccc(CNC(=O)Oc2cccc3c2OC(C)(C)C3)cc1] | 0.1171 |
| JW382 | 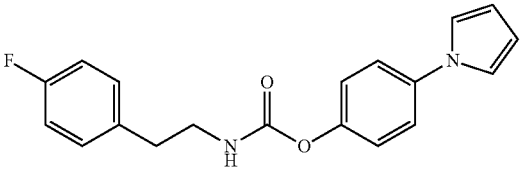 [SMILES: O=C(NCCc1ccc(F)cc1)Oc1ccc(-n2cccc2)cc1] | 1.199 |
| JW383 | 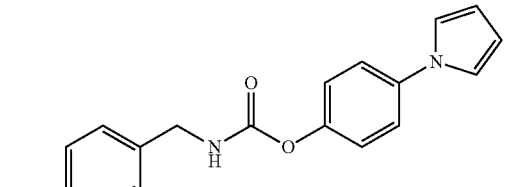 | 0.9972 |
| JW384 | 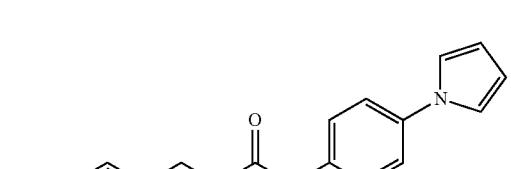 | 0.6678 |

TABLE 1-continued

KIAA 1363-Inhibitory Carbamates with IC$_{50}$ Values

| | Structure | IC$_{50}$ (μM) |
|---|---|---|
| JW385 | 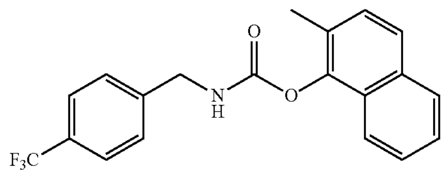 [SMILES: Cc1ccc2ccccc2c1OC(=O)NCc1ccc(C(F)(F)F)cc1] | >50 |
| JW386 | 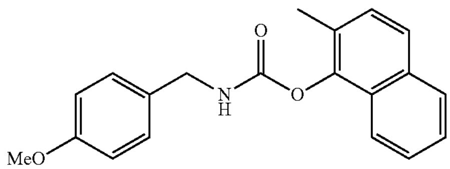 [SMILES: COc1ccc(CNC(=O)Oc2c(C)ccc3ccccc23)cc1] | >10 |
| JW387 | 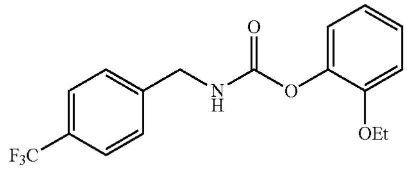 [SMILES: CCOc1ccccc1OC(=O)NCc1ccc(C(F)(F)F)cc1] | 2.821 |
| JW388 | 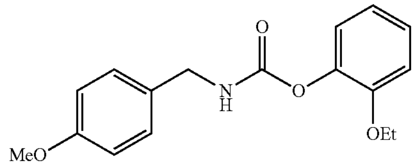 [SMILES: CCOc1ccccc1OC(=O)NCc1ccc(OC)cc1] | 1.606 |
| JW389 | 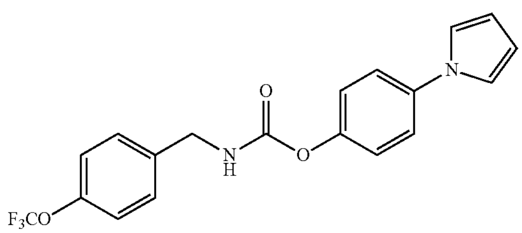 [SMILES: O=C(NCc1ccc(OC(F)(F)F)cc1)Oc1ccc(-n2cccc2)cc1] | 0.2634 |
| JW390 | 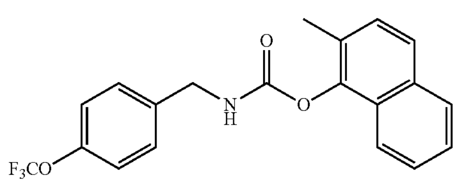 [SMILES: Cc1ccc2ccccc2c1OC(=O)NCc1ccc(OC(F)(F)F)cc1] | >10 |
| JW391 | 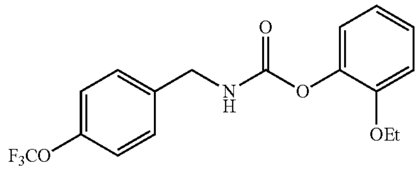 [SMILES: CCOc1ccccc1OC(=O)NCc1ccc(OC(F)(F)F)cc1] | 1.055 |
| JW392 | 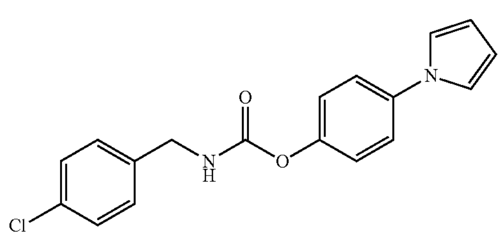 [SMILES: O=C(NCc1ccc(Cl)cc1)Oc1ccc(-n2cccc2)cc1] | 0.3849 |

TABLE 1-continued

KIAA 1363-Inhibitory Carbamates with IC$_{50}$ Values

| | Structure | IC$_{50}$ (μM) |
|---|---|---|
| JW393 | 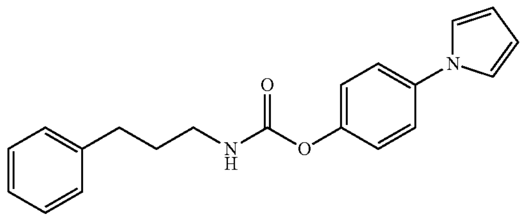 [SMILES: O=C(NCCCc1ccccc1)Oc1ccc(-n2cccc2)cc1] | >50 |
| JW395 | 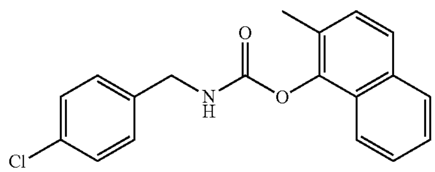 [SMILES: Cc1ccc2ccccc2c1OC(=O)NCc1ccc(Cl)cc1] | >50 |
| JW396 | 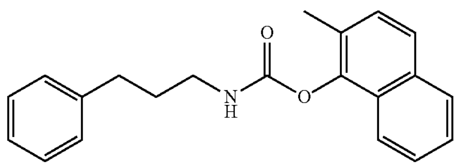 [SMILES: Cc1ccc2ccccc2c1OC(=O)NCCCc1ccccc1] | >10 |
| JW398 | 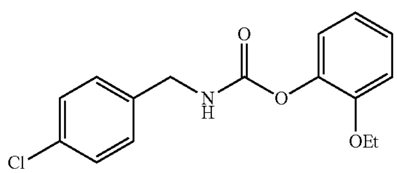 [SMILES: CCOc1ccccc1OC(=O)NCc1ccc(Cl)cc1] | 0.9768 |
| JW399 | 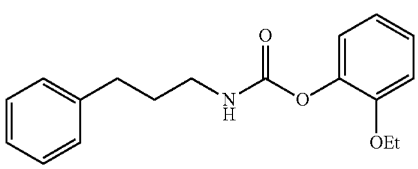 [SMILES: CCOc1ccccc1OC(=O)NCCCc1ccccc1] | 1.793 |
| JW405 | 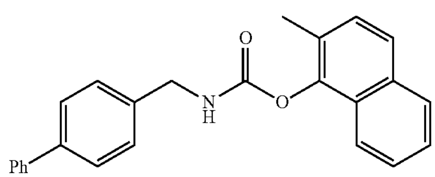 [SMILES: Cc1ccc2ccccc2c1OC(=O)NCc1ccc(-c2ccccc2)cc1] | >50 |
| JW406 | 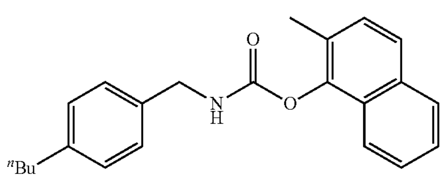 | >50 |
| JW408 | 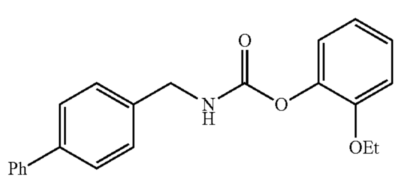 | >50 |

TABLE 1-continued
KIAA 1363-Inhibitory Carbamates with IC$_{50}$ Values
| | Structure | IC$_{50}$ (μM) |
|---|---|---|
| JW409 | 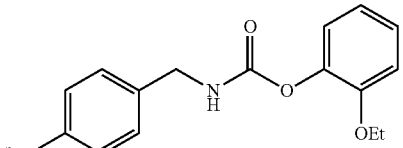 | >50 |
| JW412 | 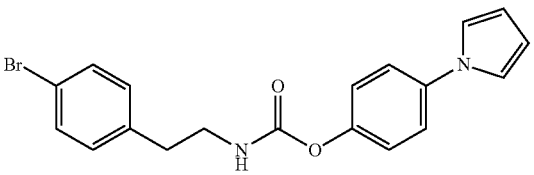 [SMILES: O=C(NCCc1ccc(Br)cc1)Oc1ccc(-n2cccc2)cc1] | 1.656 |
| JW413 | 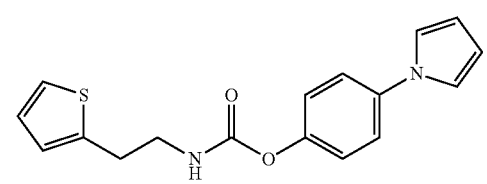 [SMILES: O=C(NCCc1cccs1)Oc1ccc(-n2cccc2)cc1] | 0.6183 |
| JW414 | 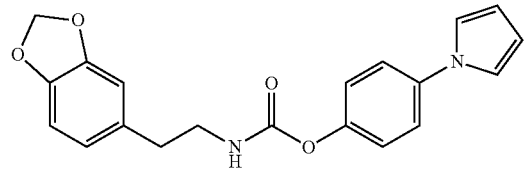 [SMILES: O=C(NCCc1ccc2c(c1)OCO2)Oc1ccc(-n2cccc2)cc1] | >10 |
| JW415 | 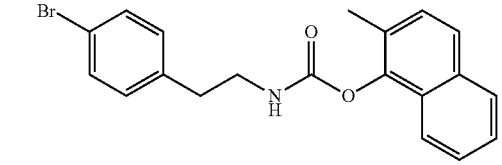 [SMILES: Cc1ccc2ccccc2c1OC(=O)NCCc1ccc(Br)cc1] | 1.077 |
| JW416 | 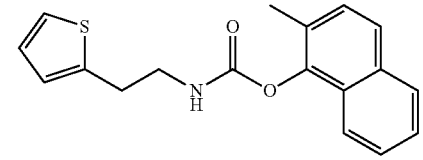 [SMILES: Cc1ccc2ccccc2c1OC(=O)NCCc1cccs1] | 3.3142 |
| JW417 | 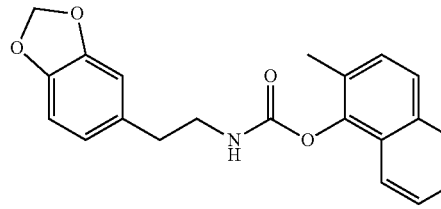 | 0.1416 |
| JW418 | 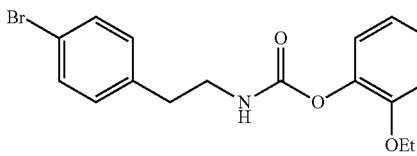 | 0.3294 |

TABLE 1-continued
KIAA1363-Inhibitory Carbamates with IC$_{50}$ Values
| | Structure | IC$_{50}$ (μM) |
|---|---|---|
| JW419 | 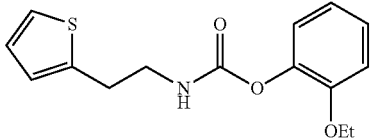 [SMILES: CCOc1ccccc1OC(=O)NCCc1cccs1] | >10 |
| JW420 | 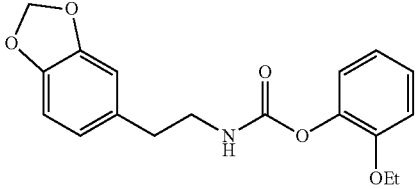 [SMILES: CCOc1ccccc1OC(=O)NCCc1ccc2c(c1)OCO2] | 1.343 |
| JW421 | 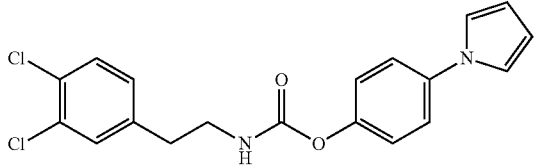 [SMILES: O=C(NCCc1ccc(Cl)c(Cl)c1)Oc1ccc(-n2cccc2)cc1] | >10 |
| JW422 | 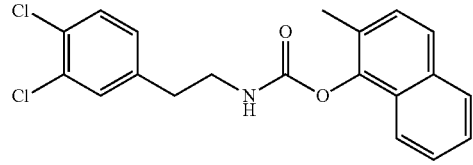 [SMILES: Cc1ccc2ccccc2c1OC(=O)NCCc1ccc(Cl)c(Cl)c1] | 0.6651 |
| JW423 | 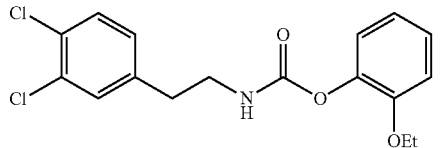 [SMILES: CCOc1ccccc1OC(=O)NCCc1ccc(Cl)c(Cl)c1] | 0.4978 |
| JW425 | 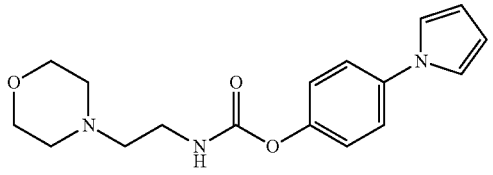 [SMILES: O=C(NCCN1CCOCC1)Oc1ccc(-n2cccc2)cc1] | >50 |
| JW426 | 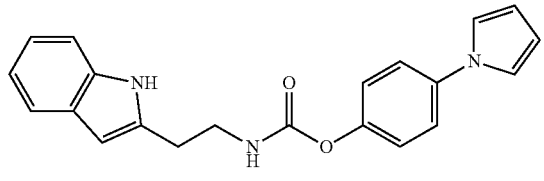 [SMILES: O=C(NCCc1cc2ccccc2[nH]1)Oc1ccc(-n2cccc2)cc1] | >50 |
| JW427 | 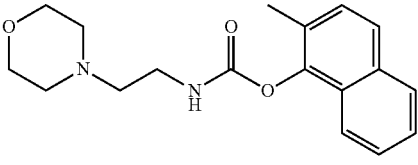 [SMILES: Cc1ccc2ccccc2c1OC(=O)NCCN1CCOCC1] | >50 |

TABLE 1-continued

KIAA 1363-Inhibitory Carbamates with IC$_{50}$ Values

| | Structure | IC$_{50}$ (μM) |
|---|---|---|
| JW428 | 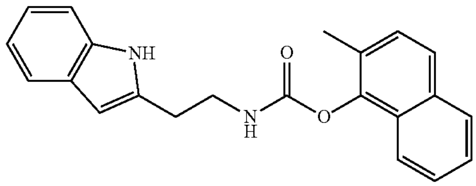 [SMILES: Cc1ccc2ccccc2c1OC(=O)NCCc1cc2ccccc2[nH]1] | 3.942 |
| JW429 | 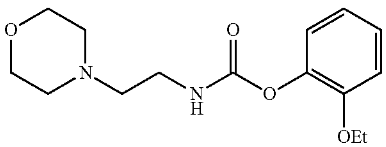 [SMILES: CCOc1ccccc1OC(=O)NCCN1CCOCC1] | >50 |
| JW430 | 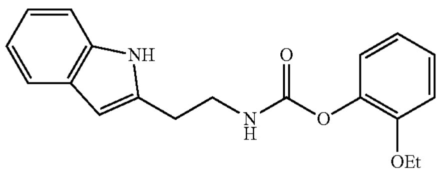 [SMILES: CCOc1ccccc1OC(=O)NCCc1cc2ccccc2[nH]1] | >50 |
| JW431 | 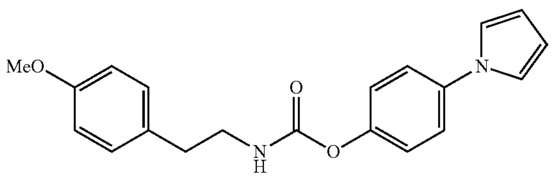 [SMILES: COc1ccc(CCNC(=O)Oc2ccc(-n3cccc3)cc2)cc1] | 1.288 |
| JW432 | 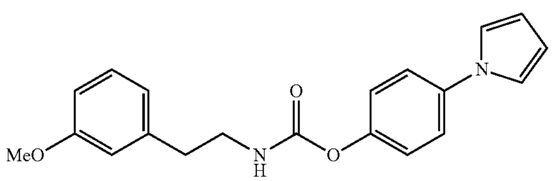 [SMILES: COc1cccc(CCNC(=O)Oc2ccc(-n3cccc3)cc2)c1] | >10 |
| JW433 | 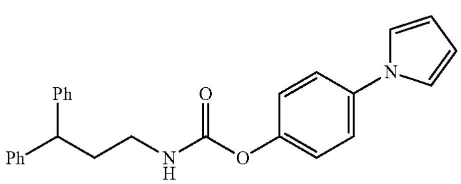 [SMILES: O=C(NCCC(c1ccccc1)c1ccccc1)Oc1ccc(-n2cccc2)cc1] | >50 |
| JW434 | 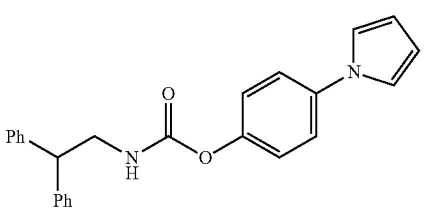 [SMILES: O=C(NCC(c1ccccc1)c1ccccc1)Oc1ccc(-n2cccc2)cc1] | >50 |
| JW435 | 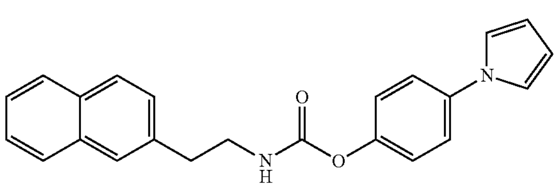 [SMILES: O=C(NCCc1ccc2ccccc2c1)Oc1ccc(-n2cccc2)cc1] | >50 |

TABLE 1-continued

KIAA 1363-Inhibitory Carbamates with IC$_{50}$ Values

| | Structure | IC$_{50}$ (µM) |
|---|---|---|
| JW436 | 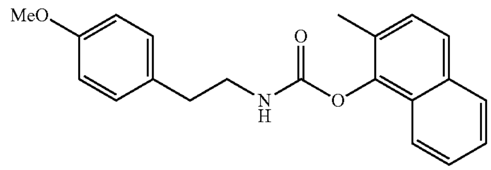 [SMILES: COc1ccc(CCNC(=O)Oc2c(C)ccc3ccccc23)cc1] | 3.001 |
| JW437 | 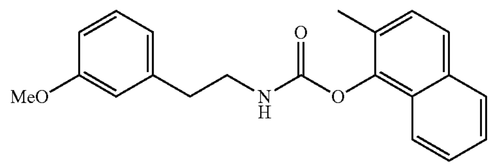 [SMILES: COc1cccc(CCNC(=O)Oc2c(C)ccc3ccccc23)c1] | 0.2093 |
| JW438 | 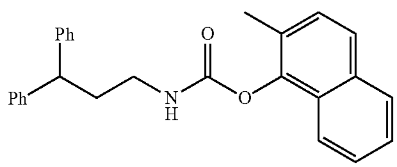 [SMILES: Cc1ccc2ccccc2c1OC(=O)NCCC(c1ccccc1)c1ccccc1] | >50 |
| JW439 | 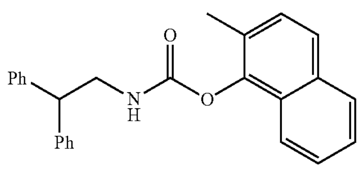 [SMILES: Cc1ccc2ccccc2c1OC(=O)NCC(c1ccccc1)c1ccccc1] | >50 |
| JW440 | 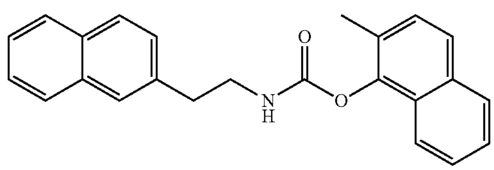 [SMILES: Cc1ccc2ccccc2c1OC(=O)NCCc1ccc2ccccc2c1] | 0.4374 |
| JW441 | 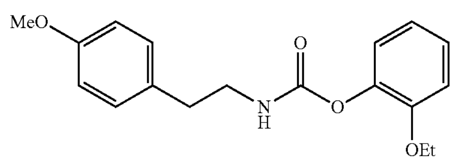 [SMILES: CCOc1ccccc1OC(=O)NCCc1ccc(OC)cc1] | >10 |
| JW442 | 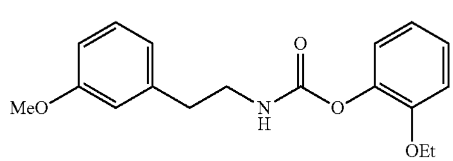 [SMILES: CCOc1ccccc1OC(=O)NCCc1cccc(OC)c1] | 1.011 |
| JW443 | 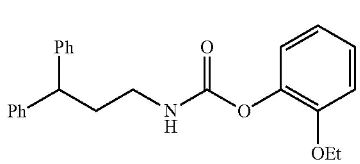 [SMILES: CCOc1ccccc1OC(=O)NCCC(c1ccccc1)c1ccccc1] | 1.827 |
| JW444 | 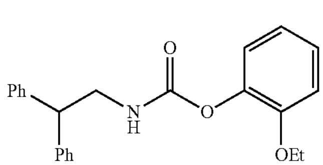 [SMILES: CCOc1ccccc1OC(=O)NCC(c1ccccc1)c1ccccc1] | 1.05 |

TABLE 1-continued
KIAA 1363-Inhibitory Carbamates with IC$_{50}$ Values
| | Structure | IC$_{50}$ (μM) |
|---|---|---|
| JW445 | 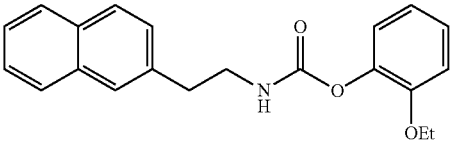 [SMILES: CCOc1ccccc1OC(=O)NCCc1ccc2ccccc2c1] | 0.8898 |
| JW446 | 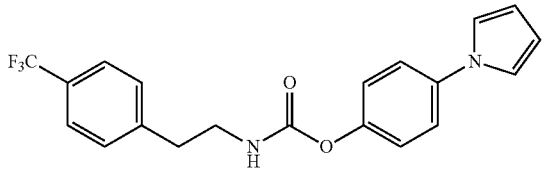 [SMILES: O=C(NCCc1ccc(C(F)(F)F)cc1)Oc1ccc(-n2cccc2)cc1] | >50 |
| JW447 | 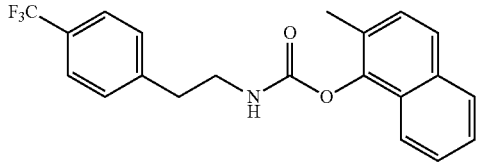 [SMILES: Cc1ccc2ccccc2c1OC(=O)NCCc1ccc(C(F)(F)F)cc1] | 0.8575 |
| JW448 | 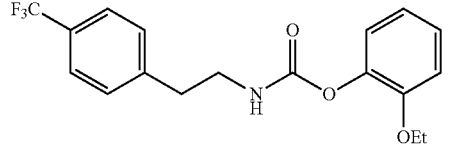 [SMILES: CCOc1ccccc1OC(=O)NCCc1ccc(C(F)(F)F)cc1] | 0.2926 |
| JW464 | 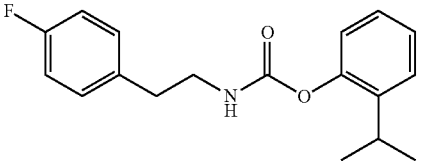 [SMILES: CC(C)c1ccccc1OC(=O)NCCc1ccc(F)cc1] | 0.0113 |
| JW465 | 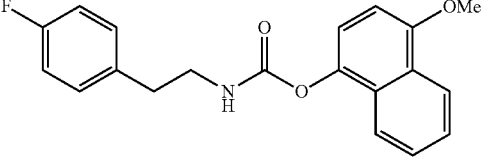 [SMILES: COc1ccc(OC(=O)NCCc2ccc(F)cc2)c2ccccc12] | >50 |
| JW466 | 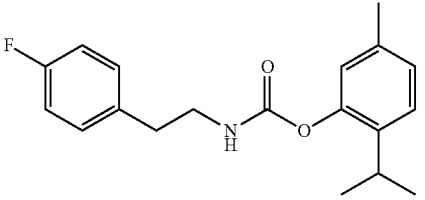 [SMILES: Cc1ccc(C(C)C)c(OC(=O)NCCc2ccc(F)cc2)c1] | 0.1968 |
| JW468 | 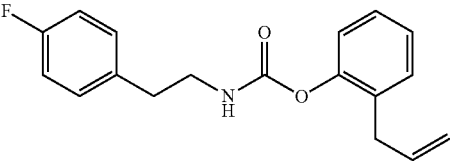 [SMILES: C=CCc1ccccc1OC(=O)NCCc1ccc(F)cc1] | 0.0943 |

TABLE 1-continued

KIAA 1363-Inhibitory Carbamates with IC$_{50}$ Values

| | Structure | IC$_{50}$ (µM) |
|---|---|---|
| JW469 | 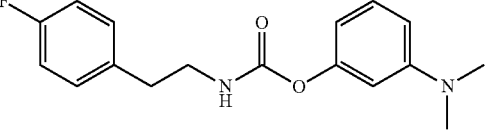 | 5.163 |
| JW472 | 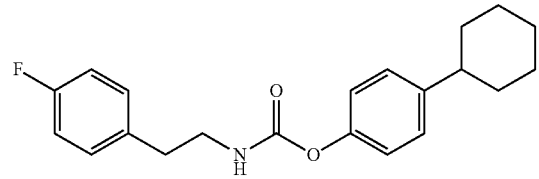 [SMILES: O=C(NCCc1ccc(F)cc1)Oc1ccc(C2CCCCC2)cc1] | 0.1189 |
| JW473 | 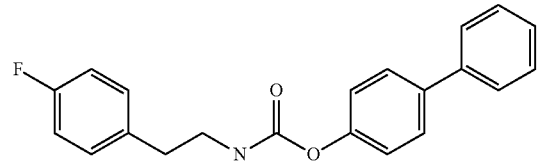 | 0.955 |
| JW474 | 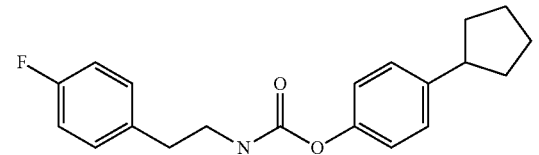 | 0.7952 |
| JW477 | 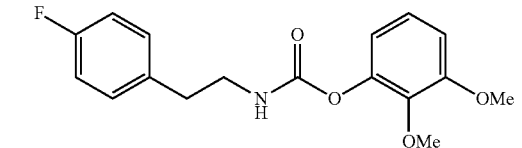 [SMILES: COc1cccc(OC(=O)NCCc2ccc(F)cc2)c1OC] | >10 |
| JW480 | 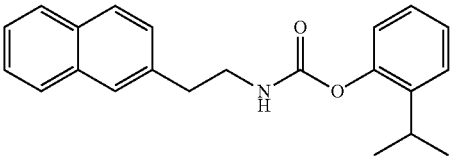 [SMILES: CC(C)c1ccccc1OC(=O)NCCc1ccc2ccccc2c1] | 0.0139 |
| JW481 | 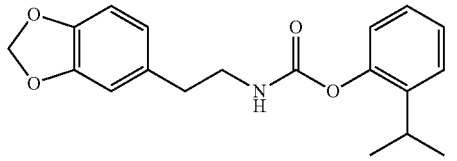 [SMILES: CC(C)c1ccccc1OC(=O)NCCc1ccc2c(c1)OCO2] | 0.0113 |
| JW482 | 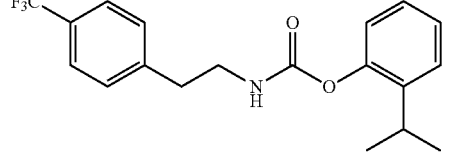 | 0.0094 |

KIAA1363 was identified and confirmed as a valuable therapeutic target for inhibition by a compound of the invention through the following experiments:

Aggressive Human Prostate Cancer Cells Show High Levels of KIAA1363 Activity.

Figure 1B:
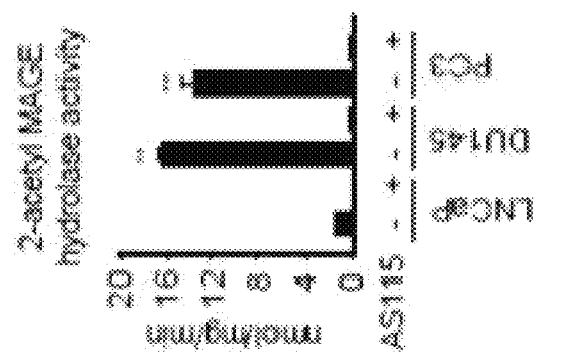
Figure 1C:
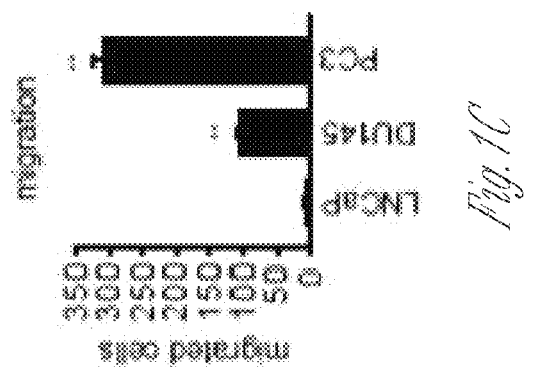
Figure 1D:
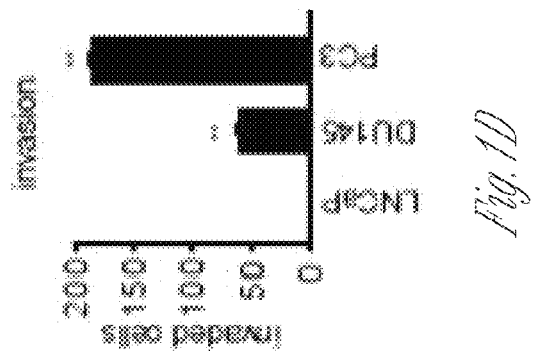
Figure 1E:
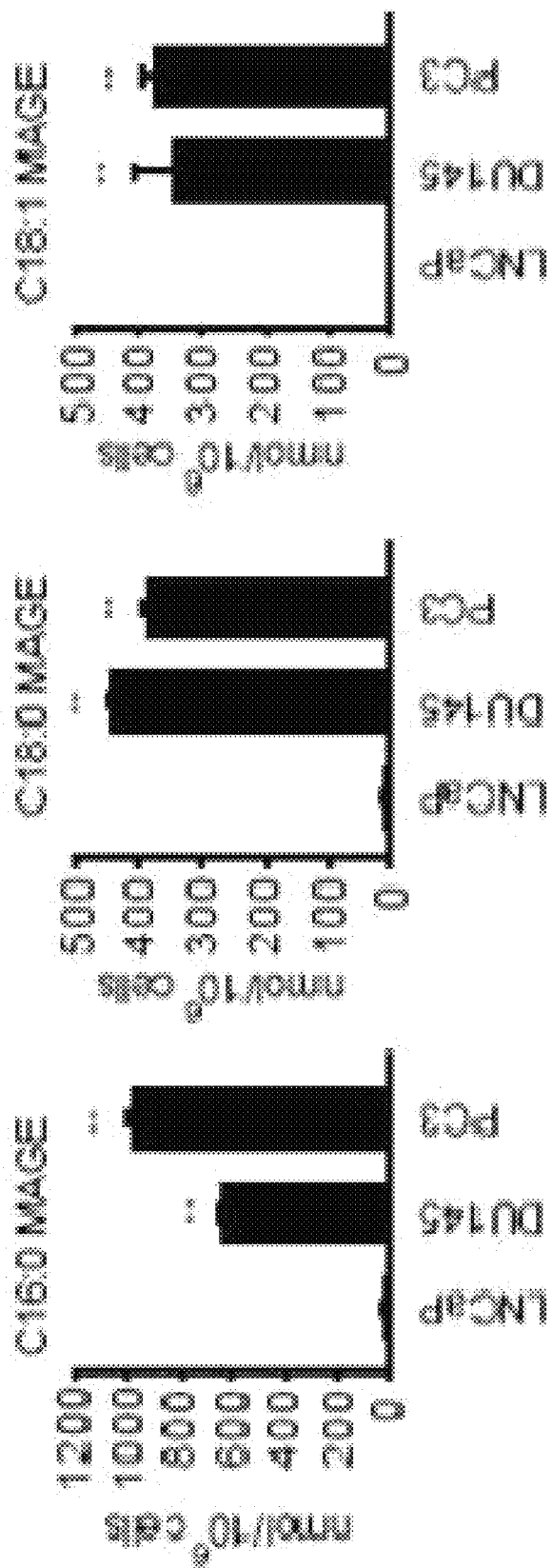

In previous ABPP studies, we found that KIAA1363 activity was elevated in aggressive human breast, melanoma, and ovarian cancer cells (Chiang et al., 2006; Jessani et al., 2002), as well as primary human breast tumors (Jessani et al., 2005). Here, we analyzed a panel of human prostate cancer cell lines by ABPP using the serine hydrolase-directed activity-based probe fluorophosphonate-rhodamine (Jessani et al., 2002; Patricelli et al., 2001) and observed that KIAA1363 activity, detectable as a ~45 kDa FP-rhodamine-reactive doublet (FIG. 1A), was much higher in the androgen-independent human prostate cancer lines PC3 and DU145 compared to the androgen-dependent human prostate cancer line LNCaP (FIGS. 1A and B). This difference in activity was also detected using the KIAA1363 substrate 2-acetyl MAGE (FIG. 1B). PC3 and DU145 cells showed much greater migratory (FIG. 1C) and invasive (FIG. 1D) activity compared to LNCaP cells, consistent with the reported differences in aggressiveness among these cancer lines (Hoosein et al., 1991). Finally, PC3 and DU145 cells possessed higher levels of the KIAA1363-regulated NELs C16:0, C18:0, and C18:1 MAGE compared to LNCaP cells (FIG. 1E). These data, together, indicate that aggressive prostate cancer cells contain a hyperactive KIAA1363-MAGE pathway.

Development of JW480, a Potent, Selective, and In Vivo Active KIAA1363 Inhibitor.

Figure 2A:
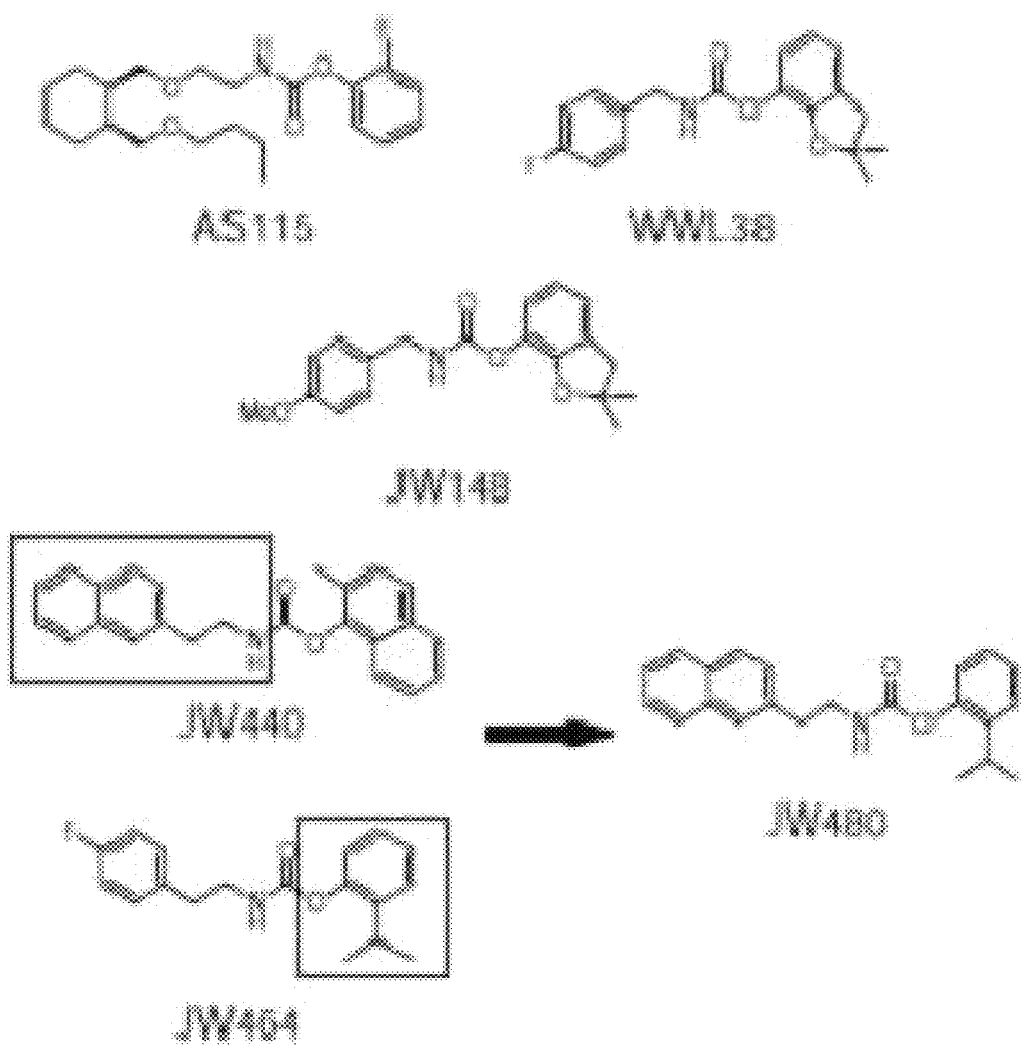
FIG. 2 shows aspects of the Development of JW480—a potent and selective KIAA1363 inhibitor. (A) Structures of various KIAA1363 inhibitors, including first-generation inhibitors, such as AS115, WWL38, and JW148, along with second-generation inhibitors JW440 and JW464, which showed improved selectivity and potency for KIAA1363, respectively. Combining key structural features of JW440 and JW464 (boxed) provided JW480, which showed improved potency and selectivity for KIAA1363. (B) The left panel shows a competitive ABPP gel for various KIAA1363 inhibitors with the mouse brain membrane proteome (10 μM inhibitor concentration). Note that AS115, but not other agents, also inhibits FAAH. The right panel shows concentration-dependent inhibition of KIAA1363 in mouse brain proteome. (C) Competitive ABPP gels comparing the activity of KIAA1363 inhibitors against the common off-target enzymes HSL and FAAH. HSL activity was measured in a rosiglitazone-differentiated 3T3-10T1/2 adipocyte proteome, while FAAH activity was measured in mouse brain proteome. (D) Concentration-dependent inhibition of AChE and KIAA1363 by JW148 and JW480. KIAA1363 activity was measured by competitive ABPP in a mouse brain proteome. AChE activity was measured in a mouse brain proteome using the substrate acetylthiocholine (Ellman et al., 1961) because this enzyme is too low in abundance for detection by gel-based ABPP. Note, however, that AChE activity can be measured by competitive ABPP-MudPIT (see FIG. 4C), which confirmed negligible cross-reactivity for JW480 with this enzyme. The following $IC_{50}$ values, also shown in the figure, were measured: JW148, $IC_{50}$ for KIAA1363 of 0.2 μM (95% confidence limit, 0.1-0.3 μM); $IC_{50}$ for AChE of 1 μM (1.09-1.3 μM); JW480 $IC_{50}$ for KIAA1363 of 0.02 μM (0.021-0.025 μM); $IC_{50}$ for AChE>100 μM. Gels are representative images from n=3; Data in (D) are presented as means±standard error of the mean (SEM); n=3/group.
Figure 2B:
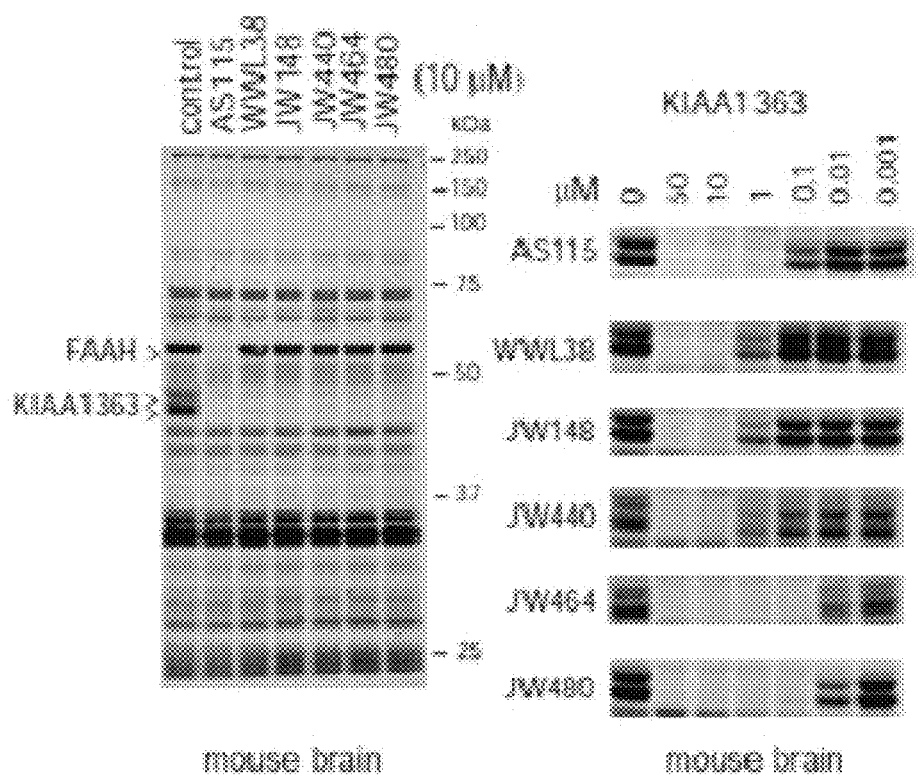
Figure 2C:
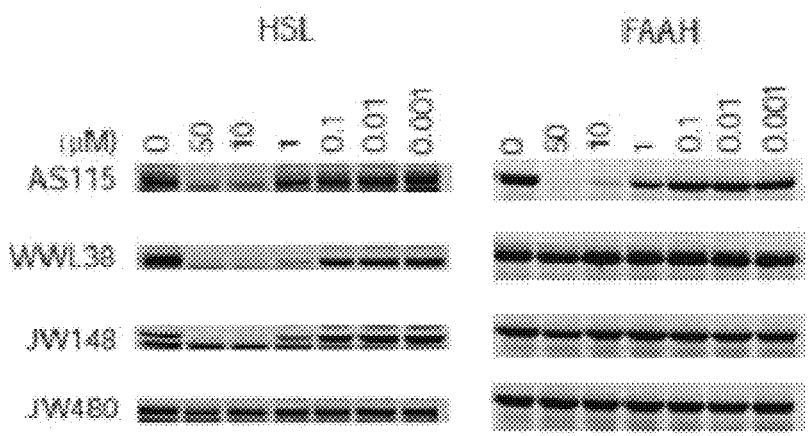
Figure 2D:
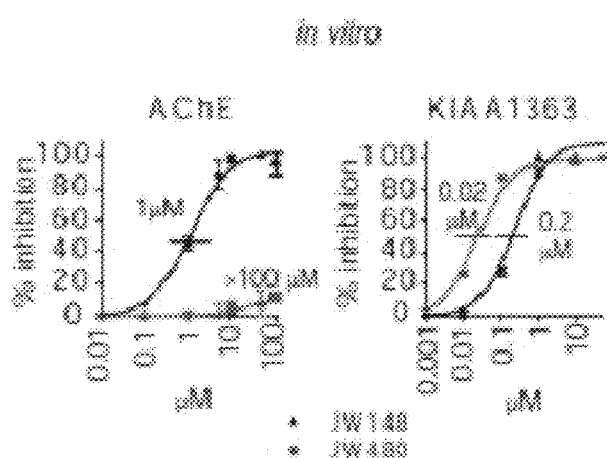
Figure 8A:
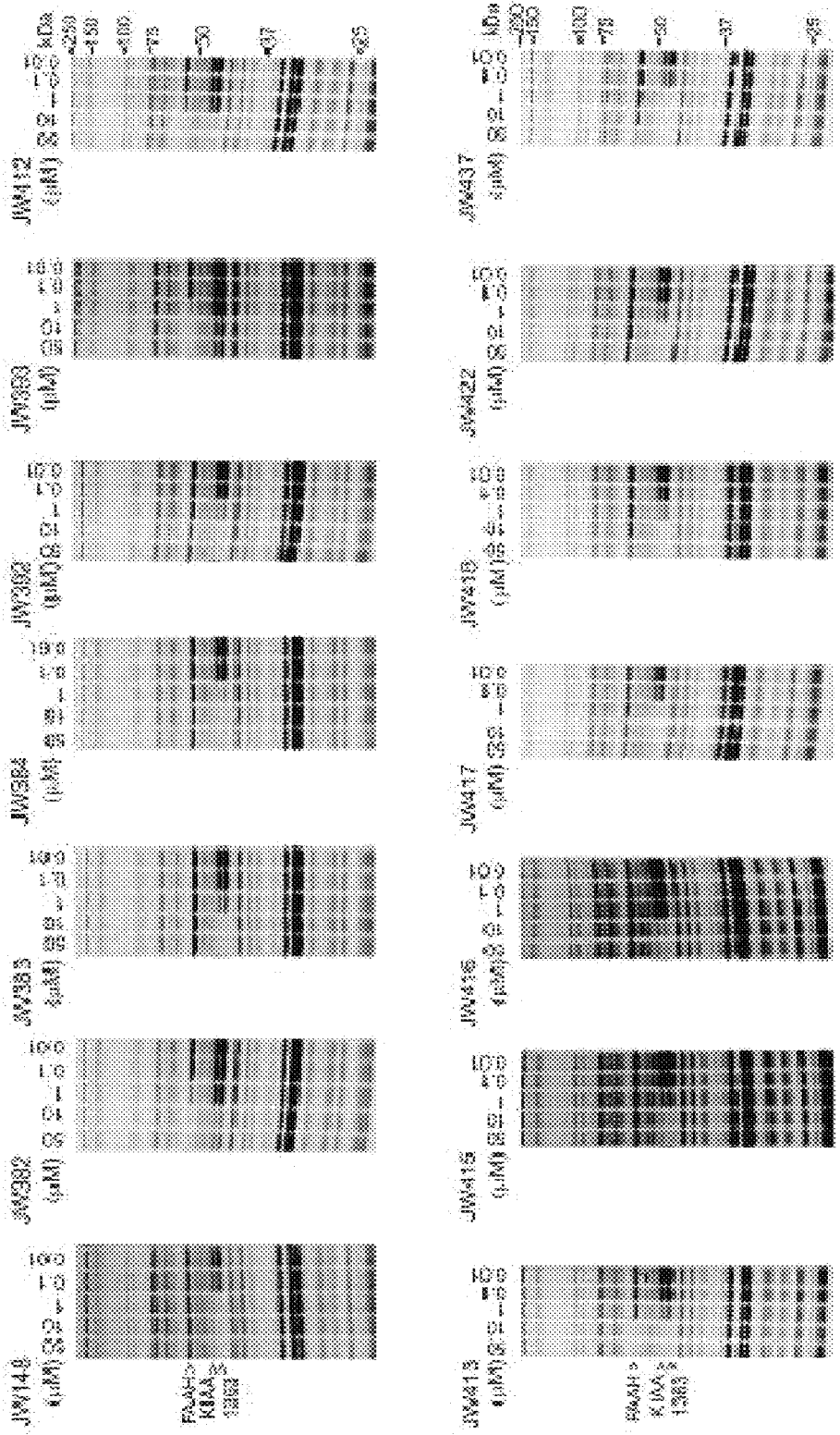
FIG. 8 shows representative gel-based ABPP results for KIAA1363 inhibitors analyzed in mouse brain membrane proteome.
Figure 8B:
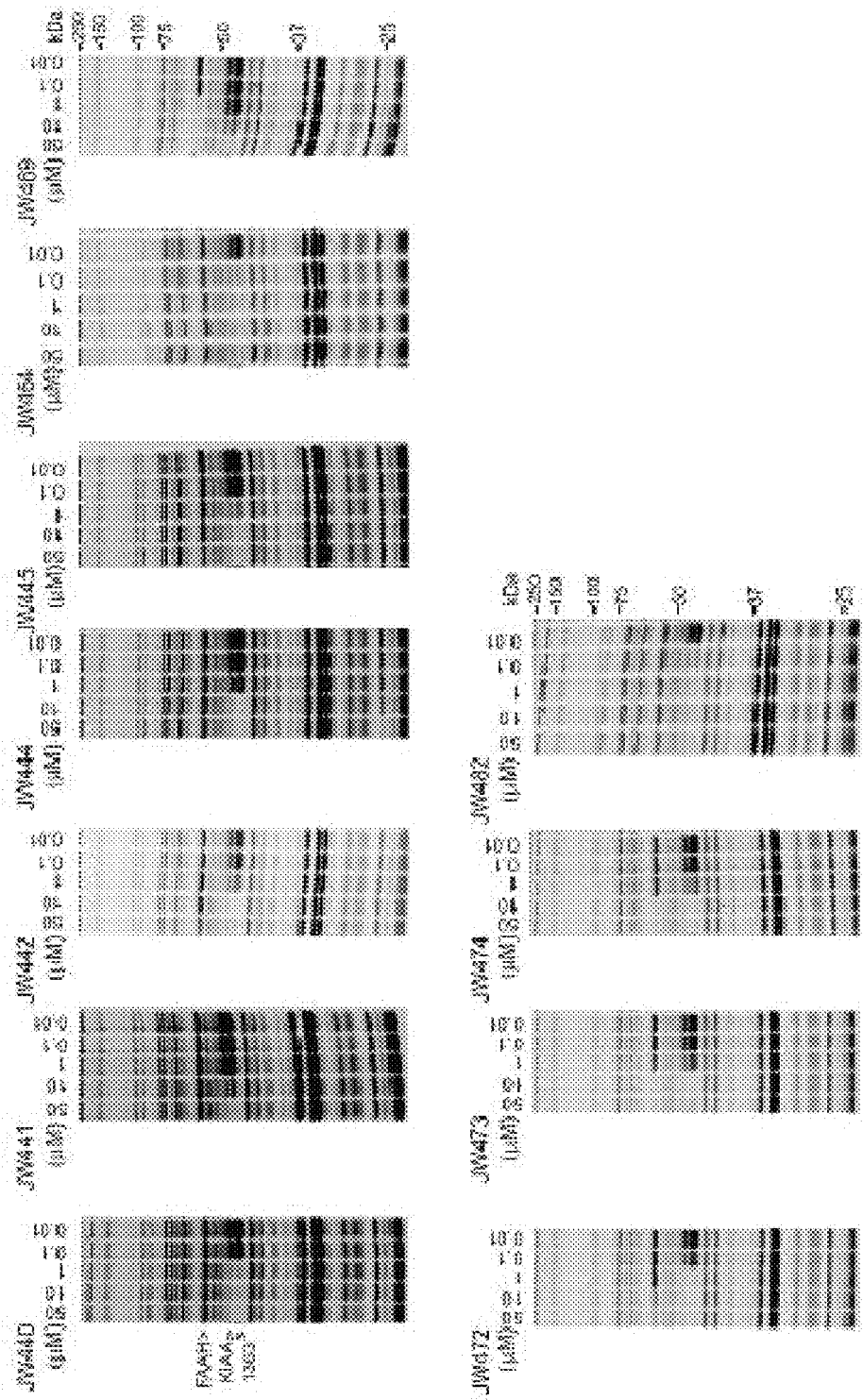

We next wanted to examine the function of KIAA1363 in prostate cancer cells. While lead inhibitors, such as trifluoromethyl ketones (Leung et al., 2003) and the carbamate AS115 (Chiang et al., 2006) (FIG. 2A), have been created for KIAA1363, these reagents lack the desired combination of selectivity and in vivo activity suitable for extensive biological studies. In a recent large-scale screen (Bachovchin et al., 2010), we discovered a new structural class of carbamates, representative members of which include WWL38 and JW148 (FIG. 2A), that inhibited KIAA1363 with good selectivity compared to common off-target enzymes such as fatty acid amide hydrolase (FAAH), as judged by gel-based competitive ABPP of a mouse brain proteome (FIG. 2B). This enhanced selectivity appeared to be imparted by the O-2,3-dihydrobenzofuran leaving group, which is well-tolerated by KIAA1363 but not most other serine hydrolases (see also FIG. 8 and Table S1). However, WWL38 and JW148 showed only moderate potency for KIAA1363 ($IC_{50}$ values ~200 nM) and still exhibited cross-reactivity with two other serine hydrolases—hormone-sensitive lipase (HSL) (FIG. 2C) and acetylcholinesterase (AChE) (FIG. 2D). We sought to enhance the potency and selectivity of these lead carbamates through ABPP-guided medicinal chemistry.

Figure 9A:
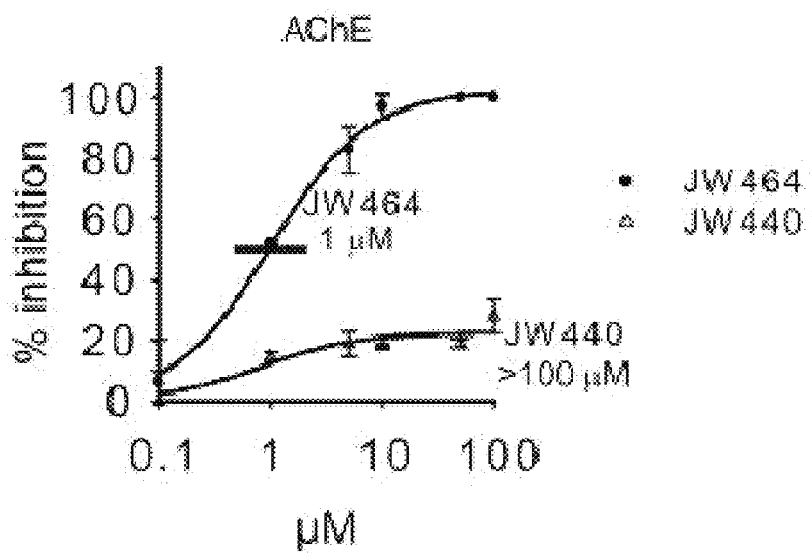
FIG. 9 shows activity of lead KIAA1363 inhibitors JW464 and JW440 against off-target enzymes AChE (A) and HSL (B). AChE activity was assessed by acetylthiocholine hydrolysis in mouse brain membrane proteome and HSL activity was determined by ABPP analysis of HSL from a rosiglitazone-differentiated 3T3-10T1/2 adipocyte proteome. Data are presented as means±standard error of the mean (SEM); n=3-4/group.
Figure 9B:
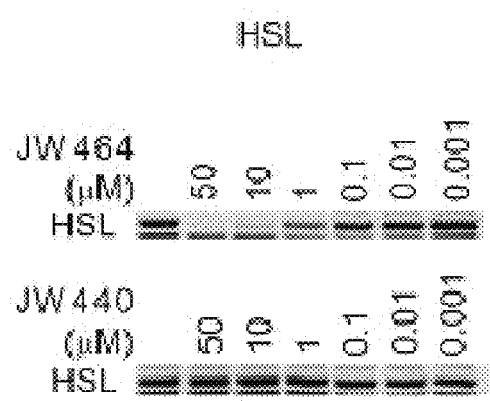

We noted that replacing the O-2,3-dihydrobenzofuran group of WWL38 and JW148 with an O-2-isopropylphenyl leaving group created a carbamate JW464 (FIG. 2A) with much improved potency for KIAA1363 (FIG. 2B), but which still showed cross-reactivity with AChE (FIG. 9). On the other hand, O-aryl carbamates with a bulkier N-ethylnaphthalene substituent, such as JW440 (FIG. 2B), showed little or no activity against AChE or HSL (FIG. 9), while maintaining good potency for KIAA1363 (FIG. 2B). Combining these two structural features engendered a carbamate JW480 that inhibited mouse brain KIAA1363 with exceptional potency (ICs value=20 nM; FIG. 2B, D), while showing negligible cross-reactivity with HSL (FIG. 2C), ACHE (FIG. 2D), or other mouse brain serine hydrolases (FIG. 2B).

Figures 10C, 10D, 10E:
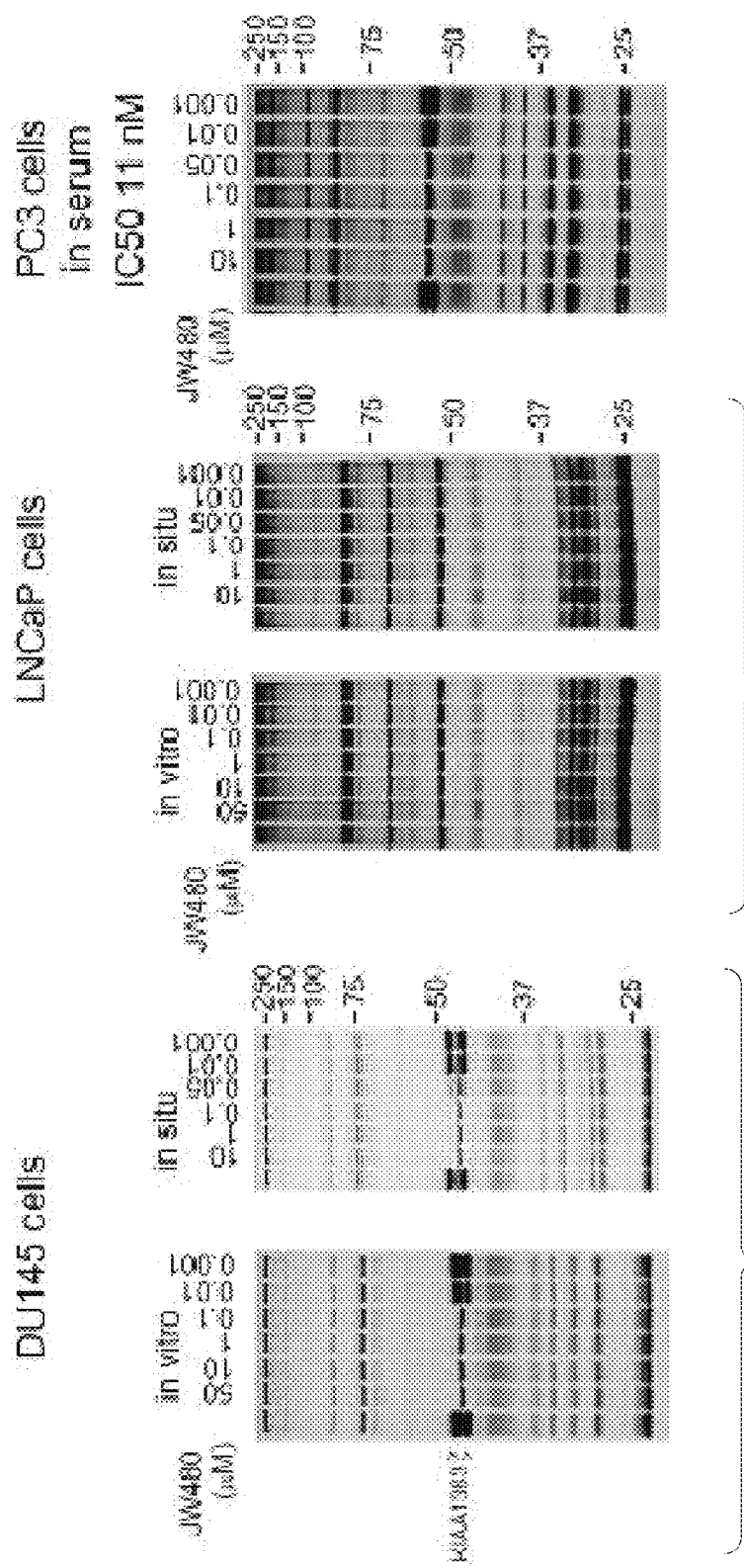
FIG. 10 shows evidence of inhibition of KIAA1363 in PC3 cells by JW480. (A) Inhibition of KIAA1363 by JW480 in PC3 cells as measured by hydrolysis of the substrate 2-acetyl MAGE Substrate assays were performed as described in the Experimental Procedures section. (B) Time-course of KIAA1363 inhibition in PC3 cells. PC3 cells were treated with JW480 (1 μM) and, after the indicated times, harvested and analyzed by competitive ABPP. Inhibition of KIAA1363 was maintained for at least 48 hr. Data are presented as means±standard error of the mean (SEM); n=3-4/group. (C, D) Gel-based competitive ABPP profiles of proteomes from DU145 (C) and LNCaP (D) cells treated with a range of concentrations of JW480 in vitro or in situ. (E) Gel-based competitive ABPP profiles of proteomes from PC3 cells treated with a range of concentrations of JW480 in situ in the presence of media containing 10% fetal calf serum.

We next confirmed that JW480 also inhibited human KIAA1363 in PC3 cell proteomes (in vitro treatment), showing an $IC_{50}$ value of 12 nM in competitive ABPP assays (FIG. 3A). Similar inhibition was observed in living PC3 cells in the presence of absence of 10% fetal calf serum (in situ treatment), where JW480 inactivated KIAA1363 with an $IC_{50}$ values of 6-12 nM (FIG. 3B and FIG. 10). We also confirmed inhibition of KIAA1363 by JW480 using a 2-acetyl MAGE substrate assay (FIG. 10). The in situ inhibition of KIAA1363 by JW480 (1 µM) was maintained for at least 48 hr (FIG. 10). JW480 showed excellent selectivity for KIAA1363 in PC3 cells (FIG. 3A. B), as well as in DU145 and LNCaP cells (FIG. 10), as judged by gel-based competitive ABPP. This selectivity was confirmed by competitive ABPP-MudPIT (Li et al., 2007; Long et al., 2009a), a mass-spectrometry-based method that displays higher resolution than gel-based ABPP and revealed no off-target activity for JW480 (1 uM in situ treatment, 4 hr) across the >30 serine hydrolase activities detected in PC3 cells (FIG. 3C).

We next asked whether JW480 could inhibit KIAA1363 in vivo by treating mice with varying quantities of this inhibitor (1-80 mg/kg, i.p. or oral administration, 4 hr) and then sacrificing the animals and analyzing their brain proteomes by competitive ABPP. JW480 proved to be highly active in vivo, showing complete inhibition of brain KIAA1363 at doses of 5 and 20 mg/kg following i.p. (FIG. 4A) and oral (FIG. 4B) routes of administration, respectively. As was observed in PC3 cells. JW480 showed excellent selectivity for KIAA1363 in brain proteomes from inhibitor-treated mice as judged by gel-based competitive ABPP (FIG. 4A, B). This selectivity was confirmed by competitive ABPP-MudPIT, where only a single off-target was detected among the ~30 serine hydrolase activities detected in the brain proteome—the carboxylesterase ES1 (FIG. 4C). ES1 is not expressed in the brain (Krishnasamy et al., 1998), but rather likely originates from contaminating blood in the brain tissue preparation [this enzyme is secreted into the blood by the liver (Krishnasamy et al., 1998)]. The selectivity profile of JW480 thus matches those of other carbamate inhibitors of serine hydrolases, such as the FAAH inhibitor URB597 (Kathuria et al., 2003) or the monoacylglycerol lipase inhibitor JZL184 (Long et al., 2009a), which also show excellent specificity for their target enzymes with the exception of some cross-reactivity with carboxylesterases (Alexander and Cravatt, 2005; Long et al., 2009b). Finally, time course studies confirmed that inhibition of KIAA1363 was maintained in vivo for up to 24 hr following a single administration of JW480 (20 mg/kg, oral; FIG. 4C, inset).

These data, taken together indicate that JW480 is a potent and selective inhibitor of both human and mouse KIAA1363 that can be used to inactivate this enzyme in living cells or animals.

JW480 Lowers MAGEs and Impairs Pathogenicity of Prostate Cancer Cells.

Figure 5A:
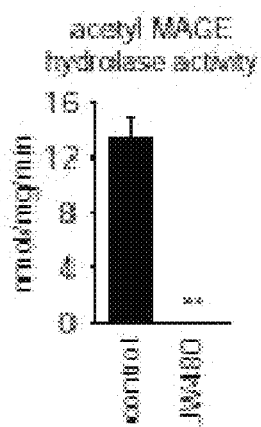
FIG. 5 shows evidence of the disruption of KIAA1363 activity reduces MAGE lipids in prostate cancer cells. (A and C) JW480 ablates KIAA1363 activity as assessed by 2-acetyl MAGE hydrolytic activity (1 μM, 48 h) in PC3 (A) and DU145 (C) cells. (B and D) JW480 significantly reduces MAGE levels in PC3 (B) and DU145 (D) (1 μM, 48 hr). (E) Stable knockdown of KIAA1363 using a short-hairpin oligonucleotide (shKIAA1363) reduces KIAA1363 activity by >70% in PC3 cells as assessed by ABPP (left) or 2-acetyl MAGE hydrolytic activity (right). (F) shKIAA1363 PC3 cells have significantly lower levels of MAGEs. **p<0.01 for JW480-treated or shKIAA1363 cells compared to their respective control groups (DMSO-treated and parental/sh-Control cells). Data are presented as means±standard error of the mean (SEM); n=4-5/group.
Figure 5B:
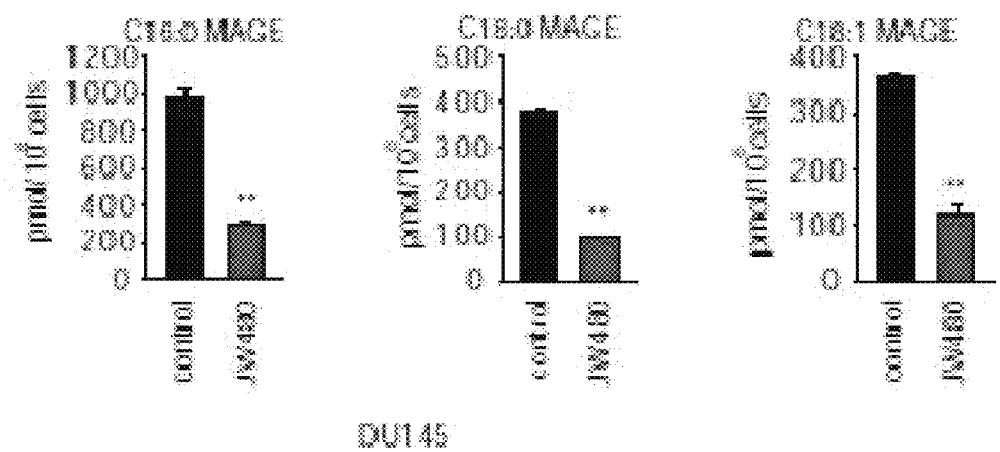
Figure 5C:
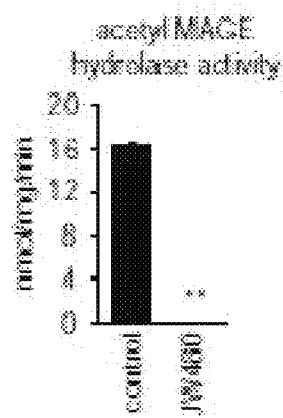
Figure 5D:
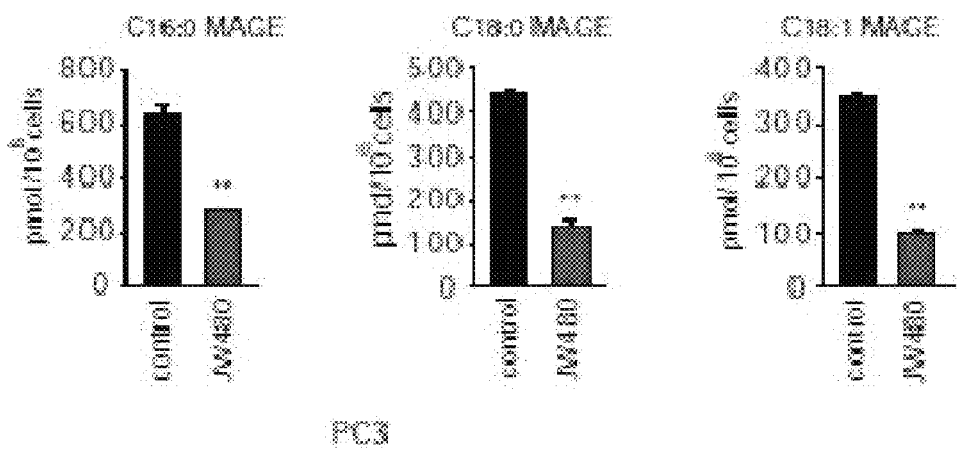
Figure 5E:
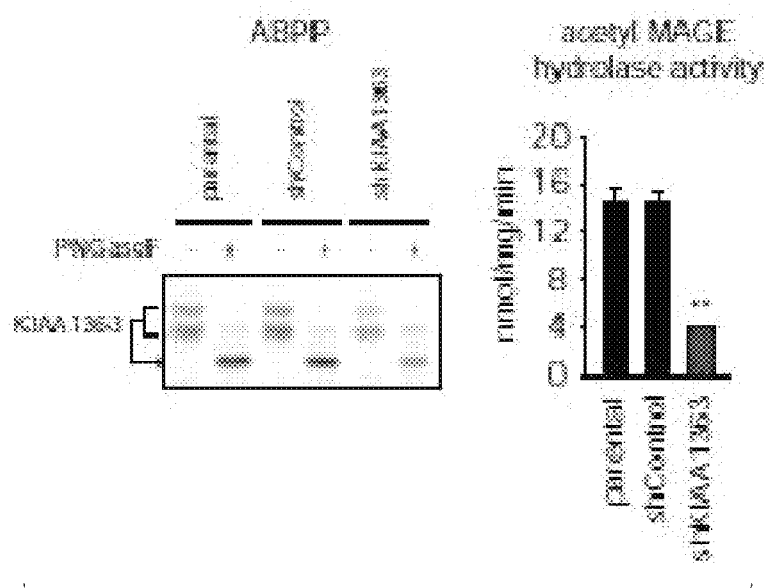
Figure 5F:
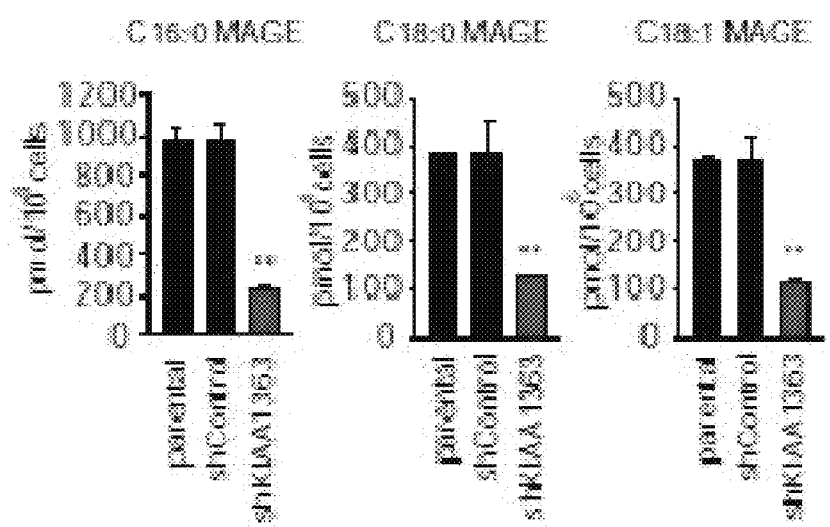
Figure 11:
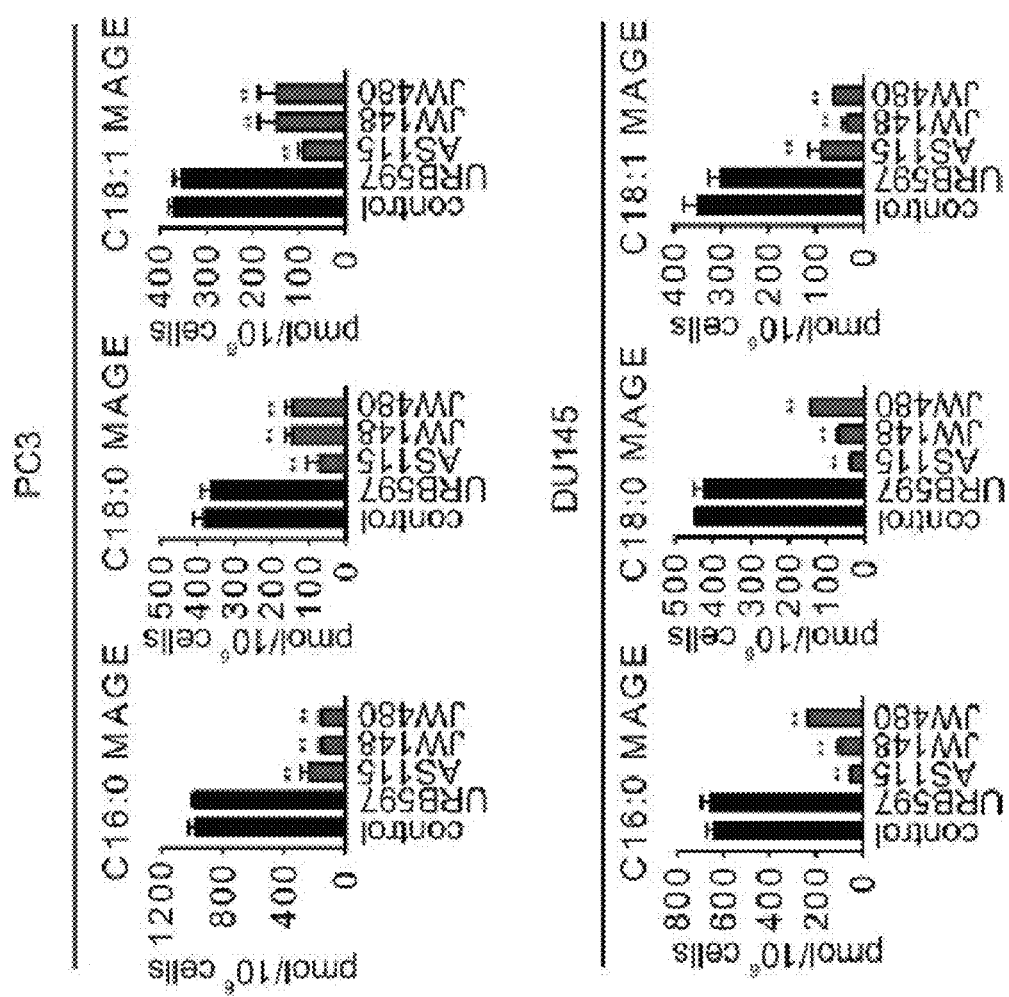
FIG. 11 shows effects of KIAA1363 inhibitors on MAGE levels in prostate cancer cells. KIAA1363 inhibitors AS115, JW148, and JW480 (10 μM, 4 h in situ), but not the FAAH inhibitor URB597 (10 μM, 4 h in situ) lower MAGE levels in PC3 and DU145 cells. **p<0.01 compared to DMSO control assays. Data are presented as means±standard error of the mean (SEM); n=4-5/group.
Figure 12A:
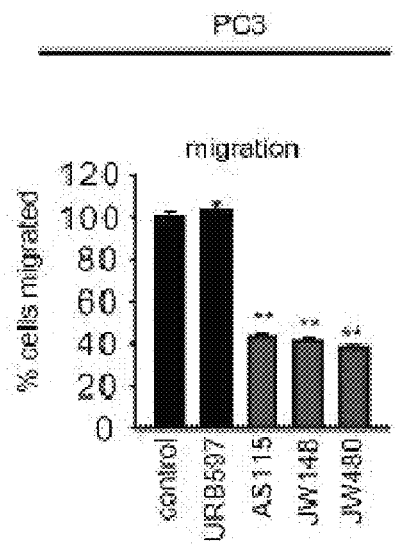
FIG. 12 shows effects of KIAA1363 inhibitors on prostate cancer cell pathogenicity. KIAA1363 inhibitors AS115, JW148, and JW480 (10 μM, 4 h in situ), but not the FAAH inhibitor URB597 (10 μM, 4 h in situ) impair PC3 and DU145 migration (A and B), serum-free cell survival (C and D), and invasion (F and G). E, JW480 (1 μM, 48 h in situ treatment) does not affect the survival of LNCaP cells, which express low levels of KIAA1363. **p<0.01 compared to DMSO control assays. Data are presented as means±standard error of the mean (SEM); n=4-5/group.
Figure 12B:
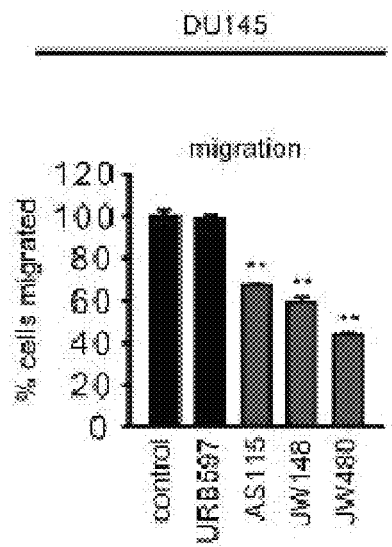
Figure 12C:
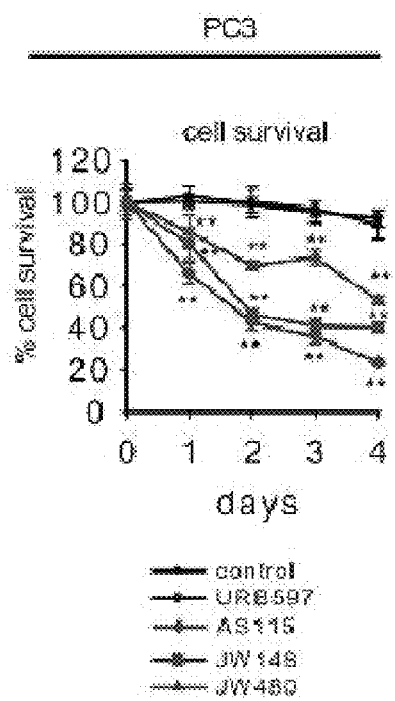
Figure 12D:
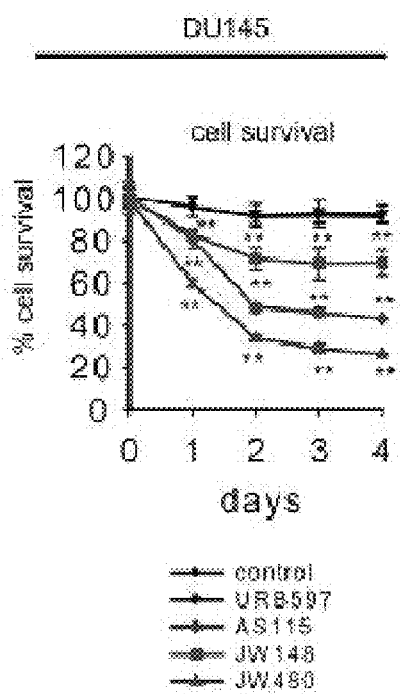
Figure 13:
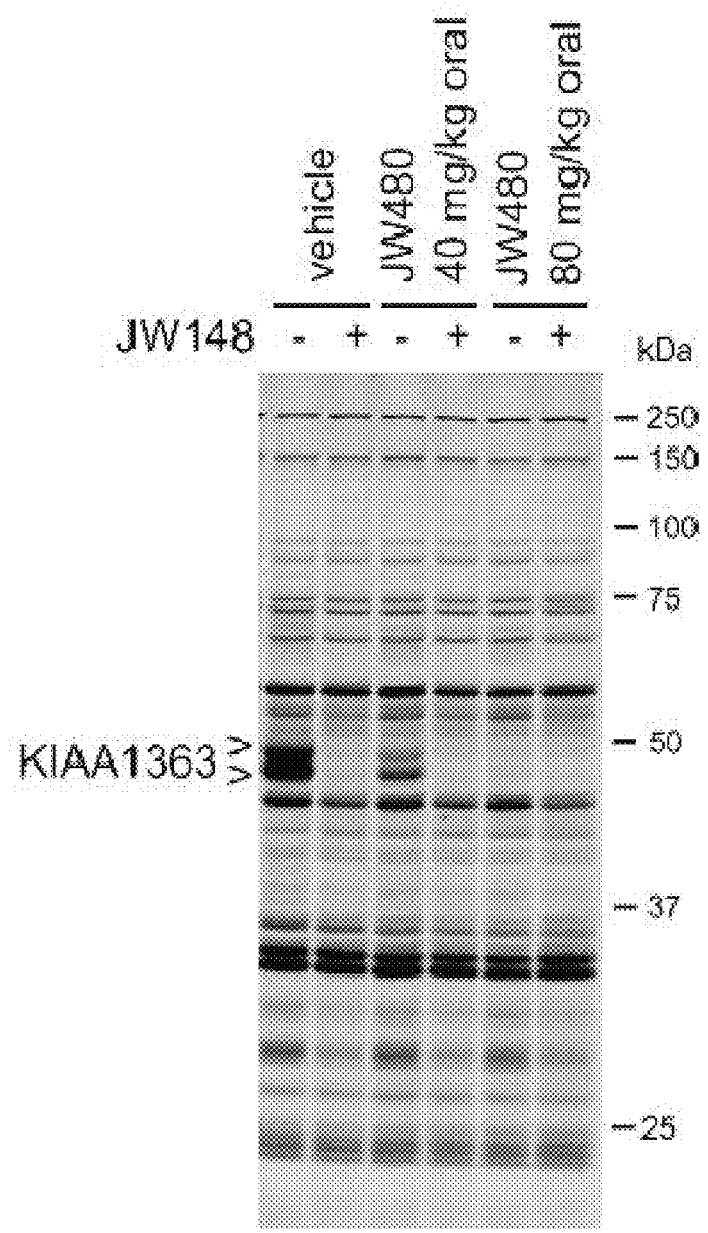
FIG. 13 shows evidence that higher quantities of JW480 are required to completely inhibit KIAA1363 in SCID mice. In contrast to normal mice, where 20 mg/kg (oral) of JW480 was required to completely inactivate brain KIAA1363, 80 mg/kg JW480 (oral) was required to achieve equivalent degrees of inactivation in the immunedeficient SCID mouse strain.

We next tested the effects of JW480 on the KIAA1363-MAGE pathway in prostate cancer cells. JW480 treatment (1 µM) completely blocked 2-acetyl MAGE hydrolase activity (FIG. 5A, C) and caused significant reductions in MAGE lipids (FIG. 5B, D) in both PC3 (FIG. 5B) and DU145 (FIG. 5D) cells. Similar effects were observed in a PC3 line where KIAA1363 was stably knocked down by a small hairpin (sh) RNA (shKIAA1363 cells; FIG. 5E, F). Other KIAA1363 inhibitors, such as AS115 and JW148, but not the FAAH inhibitor URB597, also caused reductions in MAGE lipids in prostate cancer cells (FIG. 11).

Figure 6A:
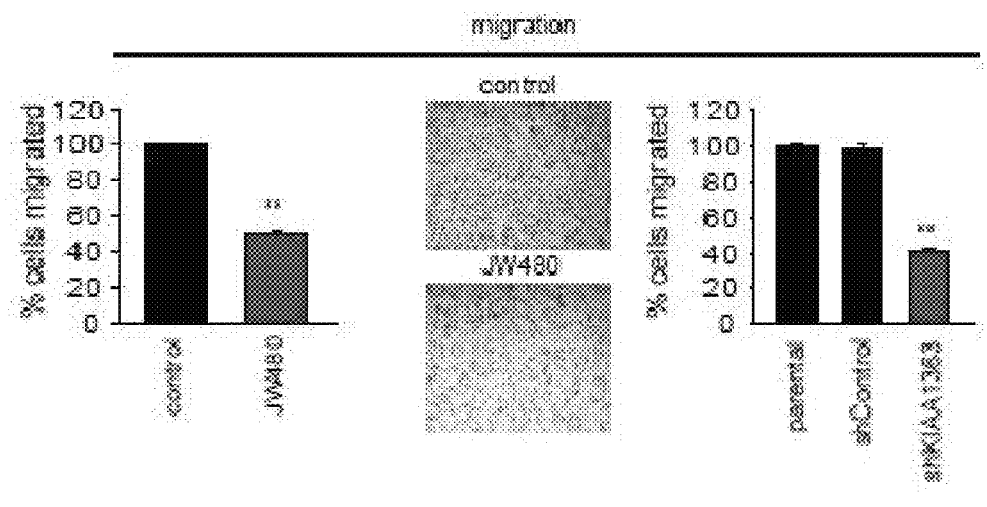
FIG. 6 shows evidence that disruption of KIAA1363 activity impairs prostate cancer cell pathogenicity. JW480-treated and shKIAA1363 PC3 cells show reduced migration (A), invasion (B), and serum-free cell survival (C). Cells were treated with JW480 (1 μM, 48 h in situ) for 48 hr prior to biological measurements. **p<0.01 for JW480-treated or shKIAA1363 cells compared to their respective control groups (DMSO-treated and parental/shControl cells). Data are presented as means±standard error of the mean (SEM); n=4-5/group.
Figure 6B:
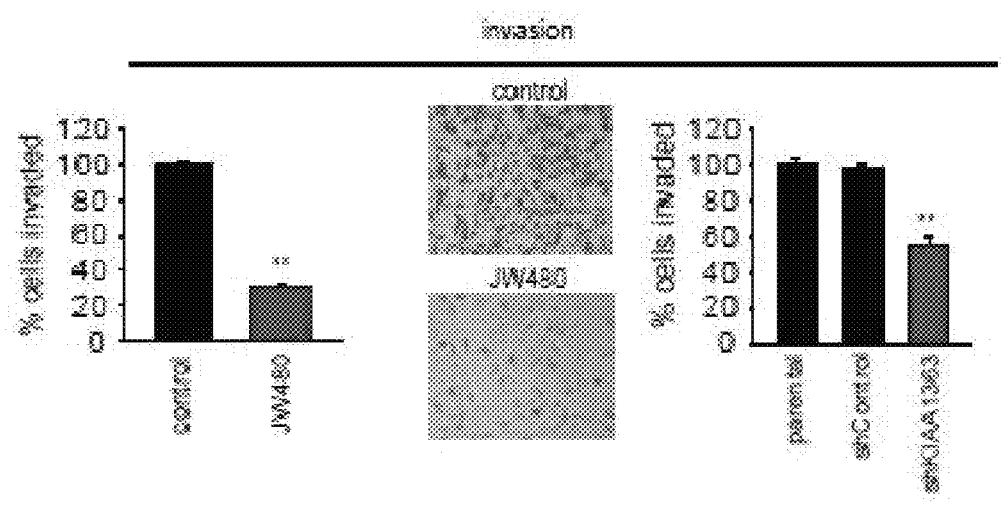
Figure 6C:
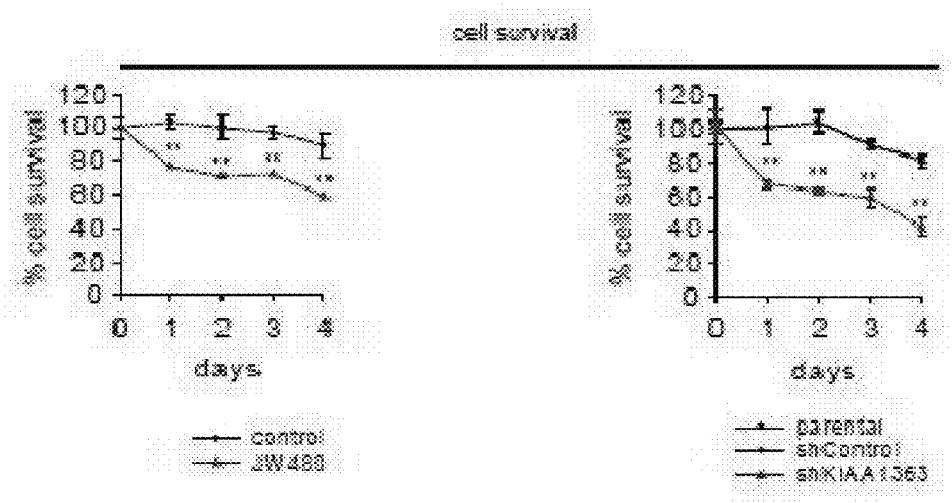
Figure 7A:
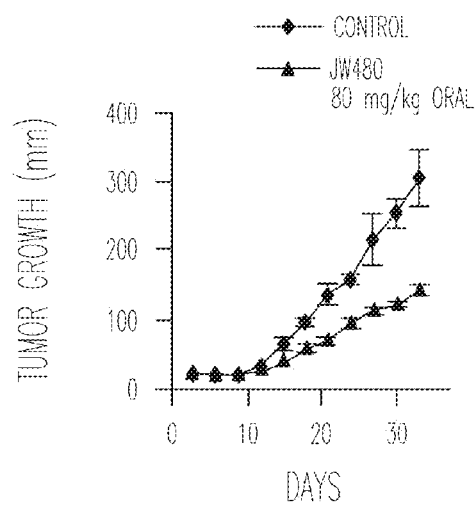
FIG. 7 shows evidence that disruption of KIAA1363 activity impairs prostate tumor growth in vivo. (A) JW480 treatment (80 mg/kg, oral gavage, one dose per day, initiated on the day of tumor cell implantation) significantly reduces PC3 tumor xenograft growth in immune-deficient SCID mice. We used a dose of 80 mg/kg JW480 because we found that a higher quantity of this compound was required to completely block KIAA1363 in SCID mice compared to normal mice. (B) Tumors from mice treated with JW480, removed 4 hr after the final administered dose of JW480 (day 33, part A), show complete loss of KIAA1363 activity compared to control (vehicle-treated) tumors as determined by ABPP. Ex vivo treatment with JW148 (10 μM, 30 min) was used to confirm that the upper and lower FP-rhodamine-reactive bands correspond to KIAA1363, while the middle FP-rhodamine-reactive band is another (JW148-insensitive) serine hydrolase. (C) shKIAA1363 PC3 cells also show significantly reduce tumor growth compared to parental and shControl PC3 cells in a SCID mouse xenograft model. **p<0.01 for JW480-treated or shKIAA1363 cells compared to their respective control groups (vehicle-treated and parental/shControl cells). Data are presented as means±standard error of the mean (SEM); n=6-8/group.
Figure 7B:
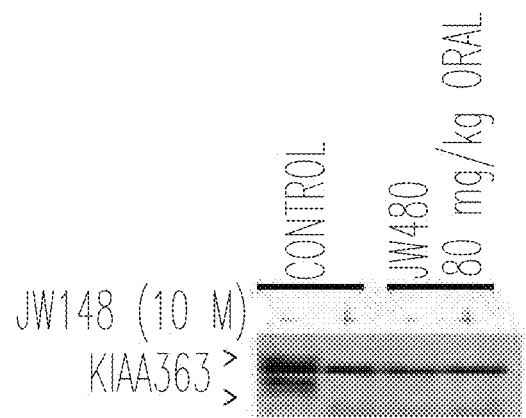
Figure 7C:
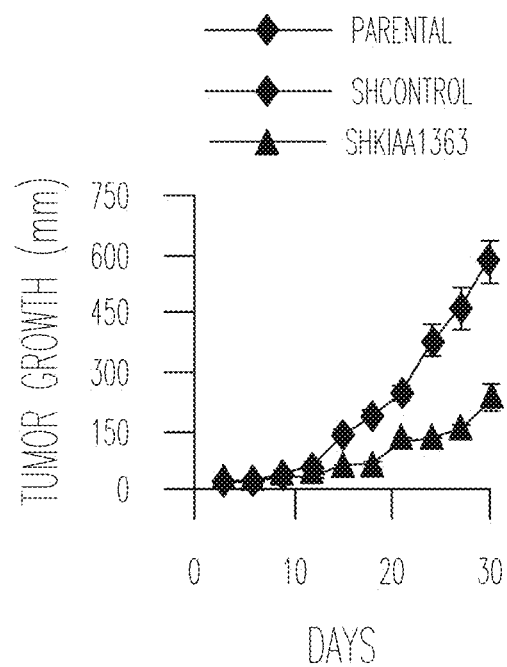

Additional studies provided evidence that the KIAA1363-MAGE pathway is important for prostate cancer aggressiveness. For instance, JW480-treated and shKIAA1363 prostate cancer cells displayed reductions in migration (FIG. 6A), invasion (FIG. 6B), and survival in serum-free media (FIG. 6C). These effects were also observed with other KIAA1363 inhibitors (AS115 and JW148), but not with the FAAH inhibitor URB597 (FIG. 12). JW480 did not affect the survival in LNCaP cells, which express low levels of KIAA1363 (FIG. 12). Finally, we took advantage of JW480's exceptional in vivo activity to test whether pharmacological blockade of KIAA1363 affected PC3 tumor growth in a mouse xenograft model. We found that PC3 tumor growth was significantly impaired in mice treated daily with JW480 (80 mg/kg, oral) compared to control mice treated with vehicle (FIG. 7A). We confirmed by competitive ABPP that KIAA1363 activity was completely ablated in tumors explanted from mice treated with JW480 (FIG. 7B). We observed a similar reduction in tumor growth for shKIAA1363 PC3 cells compared to control cells (FIG. 7C).

These results, taken together, show that pharmacological or shRNA-mediated disruption of KIAA1363 reduces MAGE levels and impairs the pathogenic properties of human prostate cancer cells.

Serine hydrolases are an exceptionally large and diverse class of enzymes that play important roles in virtually all biological processes in mammals (Simon and Cravatt, 2010). Many serine hydrolases, however, remain poorly characterized with respect to their biochemical and physiological functions. Using ABPP, we previously identified one such serine hydrolase, the integral membrane enzyme KIAA1363, as being highly expressed by aggressive human cancer cells (Jessani et al., 2002) and primary tumors (Jessani et al., 2005). We also succeeded in identifying lead inhibitors for KIAA1363, which helped to define a role for this enzyme in NEL metabolism in cancer cells (Chiang et al., 2006). These findings, when integrated with the large historical body of work designating NEL metabolism as a prominent biochemical pathway dysregulated in cancer cells (Albert and Anderson, 1977; Lin et al., 1978; Roos and Choppin, 1984; Snyder and Wood, 1969; Wood and Snyder, 1967), suggest that KIAA1363 might play an important role in tumorigenesis. Testing this hypothesis, however, required more advanced KIAA1363 inhibitors that possess the potency and selectivity needed for extensive pharmacological studies.

The starting scaffold for JW480 originated from a recent 'library-versus-library' competitive ABPP screen where we assayed 70+ serine hydrolases against 150+ carbamate small molecules (Bachovchin et al., 2010). The breadth of this screen pointed to areas for improvement of lead KIAA1363 inhibitors, most notably, in designating HSL and AChE as common off-targets for these compounds. Interestingly, and as noted previously (Bachovchin et al., 2010), neither of these enzymes share much sequence homology with KIAA1363, underscoring the value of proteomic profiling methods like competitive ABPP that can identify 'pharmacological homology' among distantly related enzymes. We were able to minimize cross-reactivity with HSL and AChE by incorporating a bulky naphthalene group into the N-alkyl substituent of JW480.

Eliminating AChE cross-reactivity was of obvious importance, given that potent inhibitors of this enzyme are neurotoxic (Casida and Quistad, 2005). Removing HSL cross-reactivity may also be valuable because both KIAA1363 and HSL are expressed at high levels in macrophages, where each enzyme has been suggested to play a role in neutral cholesterol ester hydrolysis (Buchebner et al., 2010; Igarashi et al., 2010; Okazaki et al., 2008). The relative contribution that KIAA1363 and HSL make to cholesterol ester metabolism in macrophages remains unclear, and we anticipate that JW480 should offer a valuable pharmacological tool to investigate this question. Among the more than 40 serine hydrolases counterscreened by competitive ABPP in our combined analyses of brain and cancer cell proteomes, only a single off-target for JW480 was detected—the carboxylesterase ES1. As has been discussed previously (Bachovchin et al., 2010), CEs are promiscuous enzymes involved in xenobiotic metabolism in tissues such as the liver. They are common off-targets for mechanism-based serine hydrolase inhibitors, including carbamates (Alexander and Cravatt, 2005; Bachovchin et al., 2010; Long et al., 2009b). We do not believe, however, that such cross-reactivity with ES1 (and possibly other CEs) is a major problem for using JW480 as a pharmacological tool to investigate KIAA1363 function, especially for studies in the nervous system and cancer, where CE expression is low. Furthermore, one can use carbamates that do not inhibit KIAA1363, but still show CE cross-reactivity as 'negative control' compounds, as we have shown in this study with the FAAH inhibitor URB597.

Using JW480 (and an shRNA probe that targets KIAA1363), we found that disrupting KIAA1363 reduces MAGE levels in human prostate cancer cells and impairs several of their pro-tumorigenic properties, including migration, invasion, and serum-free survival. These metabolic and cell biological effects were correlated with significant reductions in tumor growth in mouse xenograft models treated with JW480 (or using shKIAA1363 prostate cancer cells). These data collectively support a pro-tumorigenic function for KIAA1363. We should note, however, that tumors treated with JW480 or from shKIAA1363 prostate cancer cells continued to grow in vivo, indicating that blockade of KIAA1363 slows, but does not completely block tumor progression. This outcome was not due to incomplete inhibition of KIAA1363, as we were able to confirm full inactivation of KIAA1363 in explanted tumors from JW480-treated mice. In future studies, it would be interesting to test whether KIAA1363 inhibitors show additive or synergistic anti-tumor activity when combined with other chemotherapeutic agents. Also, the strong anti-invasive effects of JW480 suggest that blockade of KIAA1363 could impede cancer metastasis in vivo. Finally, more extensive biochemical and cell biological studies are required to understand the mechanism by which KIAA1363-MAGE pathway supports prostate cancer pathogenicity. Previous work showed that this pathway is coupled to the production of pro-tumorigenic lipids, such as alkyl-LPA, in ovarian cancer cells (Chiang et al., 2006). Broader metabolomic experiments should reveal whether changes in LPA or other bioactive lipids are also observed in JW480-treated prostate cancer cells.

In closing, we believe that JW480 possesses an impressive array of features that qualify it as a frontline pharmacological probe for KIAA1363, including high potency against both the human and mouse orthologues of this enzyme, minimal cross-reactivity with other serine hydrolases, and excellent activity in living cells and mice. We anticipate that future studies with JW480 will help to illuminate the role that KIAA1363 plays in many (patho)physiological processes, including cancer, macrophage biology, and the nervous system. From a methodological perspective, our success in converting lead carbamates originating from a large-scale screen (Bachovchin et al., 2010) into a KIAA1363 inhibitor that displays greatly improved potency and selectivity can be attributed, at least in part, to the information content garnered by competitive ABPP, which assays inhibitors against numerous enzymes in parallel directly in native proteomes. This type of "proteomic medicinal chemistry", which has also impacted other inhibitor development programs (Arastu-Kapur et al., 2008; Deu et al.; Li et al., 2007; Long et al., 2009a; Staub and Sieber. 2009), should continue to provide an efficient means to create versatile pharmacological probes for a wide range of enzymes.

Accordingly, compounds of the invention, through routine experimentation to determine suitability as a drug substance (pharmacokinetics, toxicity, etc.) are provided that can be used to treat a diverse range of malconditions, each mediated by its related serine hydrolase or multiple serine hydrolase enzymes. It is within ordinary skill to evaluate any compound disclosed and claimed herein for effectiveness in inhibition of a serine hydrolase and in the various cellular assays using the procedures described above or found in the scientific literature. Accordingly, the person of ordinary skill can prepare and evaluate any of the claimed compounds without undue experimentation.

Any compound found to be an effective inhibitor of a serine hydrolase implicated in a particular malcondition can likewise be tested in animal models and in human clinical studies using the skill and experience of the investigator to guide the selection of dosages and treatment regimens.

In various embodiments, the invention provides a pharmaceutical composition comprising a compound of the invention as described above. Compositions of the compounds of the invention, alone or in combination with another medicament, are provided herein. As set forth herein, compounds of the invention include stereoisomers, tautomers, solvates, prodrugs, pharmaceutically acceptable salts and mixtures thereof. Compositions containing a compound of the invention can be prepared by conventional techniques, e.g. as described in Remington: *The Science and Practice of Pharmacy*, 19th Ed., 1995, or later versions thereof, incorporated by reference herein. The compositions can appear in conventional forms, for example capsules, tablets, aerosols, solutions, suspensions or topical applications.

Typical compositions include a compound of the invention and a pharmaceutically acceptable excipient which can be a carrier or a diluent. For example, the active compound will usually be mixed with a carrier, or diluted by a carrier, or enclosed within a carrier which can be in the form of an ampoule, capsule, sachet, paper, or other container. When the active compound is mixed with a carrier, or when the carrier serves as a diluent, it can be solid, semi-solid, or liquid material that acts as a vehicle, excipient, or medium for the active compound. The active compound can be adsorbed on a granular solid carrier, for example contained in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent can include any sustained release material known in the art, such as glyceryl monostearate or glyceryl distearate, alone or mixed with a wax.

The formulations can be mixed with auxiliary agents which do not deleteriously react with the active compounds. Such additives can include wetting agents, emulsifying and suspending agents, salt for influencing osmotic pressure, buffers and/or coloring substances preserving agents, sweetening agents or flavoring agents. The compositions can also be sterilized if desired.

The route of administration can be any route which effectively transports the active compound of the invention to the appropriate or desired site of action, such as oral, nasal, pulmonary, buccal, subdermal, intradermal, transdermal or parenteral, e.g., rectal, depot, subcutaneous, intravenous, intraurethral, intramuscular, intranasal, ophthalmic solution or an ointment, the oral route being preferred.

If a solid carrier is used for oral administration, the preparation can be tabletted, placed in a hard gelatin capsule in powder or pellet form or it can be in the form of a troche or lozenge. If a liquid carrier is used, the preparation can be in the form of a syrup, emulsion, soft gelatin capsule or sterile injectable liquid such as an aqueous or non-aqueous liquid suspension or solution.

Injectable dosage forms generally include aqueous suspensions or oil suspensions which can be prepared using a suitable dispersant or wetting agent and a suspending agent Injectable forms can be in solution phase or in the form of a suspension, which is prepared with a solvent or diluent. Acceptable solvents or vehicles include sterilized water, Ringer's solution, or an isotonic aqueous saline solution. Alternatively, sterile oils can be employed as solvents or suspending agents. Preferably, the oil or fatty acid is non-volatile, including natural or synthetic oils, fatty acids, mono-, di- or tri-glycerides.

For injection, the formulation can also be a powder suitable for reconstitution with an appropriate solution as described above. Examples of these include, but are not limited to, freeze dried, rotary dried or spray dried powders, amorphous powders, granules, precipitates, or particulates. For injection, the formulations can optionally contain stabilizers, pH modifiers, surfactants, bioavailability modifiers and combinations of these. The compounds can be formulated for parenteral administration by injection such as by bolus injection or continuous infusion. A unit dosage form for injection can be in ampoules or in multi-dose containers.

The formulations of the invention can be designed to provide quick, sustained, or delayed release of the active ingredient after administration to the patient by employing procedures well known in the art. Thus, the formulations can also be formulated for controlled release or for slow release.

Compositions contemplated by the present invention can include, for example, micelles or liposomes, or some other encapsulated form, or can be administered in an extended release form to provide a prolonged storage and/or delivery effect. Therefore, the formulations can be compressed into pellets or cylinders and implanted intramuscularly or subcutaneously as depot injections. Such implants can employ known inert materials such as silicones and biodegradable polymers, e.g., polylactide-polyglycolide. Examples of other biodegradable polymers include poly(orthoesters) and poly (anhydrides).

For nasal administration, the preparation can contain a compound of the invention, dissolved or suspended in a liquid carrier, preferably an aqueous carrier, for aerosol application. The carrier can contain additives such as solubilizing agents, e.g., propylene glycol, surfactants, absorption enhancers such as lecithin (phosphatidylcholine) or cyclodextrin, or preservatives such as parabens.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet that can be prepared by conventional tabletting techniques can contain:

| Core: | |
| --- | --- |
| Active compound (as free compound or salt thereof) | 250 mg |
| Colloidal silicon dioxide (Aerosil) ® | 1.5 mg |
| Cellulose, microcryst. (Avicel) ® | 70 mg |

| Modified cellulose gum (Ac-Di-Sol) ® | 7.5 mg |
| Magnesium stearate | Ad. |
| Coating: | |
| HPMC approx. | 9 mg |
| *Mywacett 9-40 T approx. | 0.9 mg |

*Acylated monoglyceride used as plasticizer for film coating.

A typical capsule for oral administration contains compounds of the invention (250 mg), lactose (75 mg) and magnesium stearate (15 mg). The mixture is passed through a 60 mesh sieve and packed into a No. 1 gelatin capsule. A typical injectable preparation is produced by aseptically placing 250 mg of compounds of the invention into a vial, aseptically freeze-drying and sealing. For use, the contents of the vial are mixed with 2 mL of sterile physiological saline, to produce an injectable preparation.

The compounds of the invention can be administered to a mammal, especially a human in need of such treatment, prevention, elimination, alleviation or amelioration of a malcondition. Such mammals include also animals, both domestic animals, e.g. household pets, farm animals, and non-domestic animals such as wildlife.

The compounds of the invention are effective over a wide dosage range. For example, in the treatment of adult humans, dosages from about 0.05 to about 5000 mg, preferably from about 1 to about 2000 mg, and more preferably between about 2 and about 2000 mg per day can be used. A typical dosage is about 10 mg to about 1000 mg per day. In choosing a regimen for patients it can frequently be necessary to begin with a higher dosage and when the condition is under control to reduce the dosage. The exact dosage will depend upon the activity of the compound, mode of administration, on the therapy desired, form in which administered, the subject to be treated and the body weight of the subject to be treated, and the preference and experience of the physician or veterinarian in charge.

Generally, the compounds of the invention are dispensed in unit dosage form including from about 0.05 mg to about 1000 mg of active ingredient together with a pharmaceutically acceptable carrier per unit dosage.

Usually, dosage forms suitable for oral, nasal, pulmonal or transdermal administration include from about 125 µg to about 1250 mg, preferably from about 250 µg to about 500 mg, and more preferably from about 2.5 mg to about 250 mg, of the compounds admixed with a pharmaceutically acceptable carrier or diluent.

Dosage forms can be administered daily, or more than once a day, such as twice or thrice daily. Alternatively dosage forms can be administered less frequently than daily, such as every other day, or weekly, if found to be advisable by a prescribing physician.

In various embodiments, the invention provides a method of inhibiting a serine hydrolase KIAA1363, comprising contacting the hydrolase in vitro or in vivo with an effective concentration or quantity of a compound of the invention.

In various embodiments, the invention provides a method of treating a malcondition associated with a serine hydrolase, comprising administering to a patient afflicted with the malcondition an effective amount of a compound of the invention at a frequency and for a duration to provide a beneficial effect to the patient. For example, the malcondition can comprise cancer, such as prostate cancer.

In various embodiments, the invention provides a use of a compound of the invention for treatment of a malcondition, such as wherein the malcondition is associated with a serine hydrolase; for example, the malcondition can be cancer, such as prostate cancer.

In various embodiments, the invention provides a method of imaging, in vivo or in vitro, a spatial or temporal distribution, or both, of a serine hydrolase KIAA1363 within a cell or tissue, comprising contacting the cell or tissue with an effective amount or concentration of a carbamate compound of the invention comprising a fluorophore group, then, examining the cell or tissue under illumination comprising light of an excitation frequency of the fluorophore, such that light of the fluorophore emission spectrum is emitted from a spatial region, or over a period of time, or both, where the serine hydrolase is associated with the fluorophore group.

For example, a fluorescent probe comprising a carbamate compound of the invention comprising a fluorophore group can be a compound of formula (I), wherein $R^1$ is a group of formula FL-W—, wherein W is a linker bonding a fluorophore FL to the carbamate nitrogen atom, W comprising a bond, an alkylene group, an oxygen atom, an amino group, a carbonyl group, an alkylenecarbonyl group, a carboxamido group, or an alkylene carboxamido group.

For example, the cell or tissue can be studied using fluorescence microscopy to identify regions where the fluorophore is bound to the serine hydrolase, such as by irreversible acylation of the active serine residue of the hydrolase by the carbamate inhibitor. There is a particular need for activity-based imaging probes for KIAA1363, since this enzyme is subject to extensive and variable post-translational modification (primarily glycosylation) which has, so far, impeded efforts to develop antibodies for immunofluorescence imaging. Our established structure-activity relationship suggested that the naphthyl-containing carbamoylating arm of JW480 could potentially be replaced with a hydrophobic fluorophore group without substantial losses in potency or selectivity for KIAA1363.

Figure 14A:
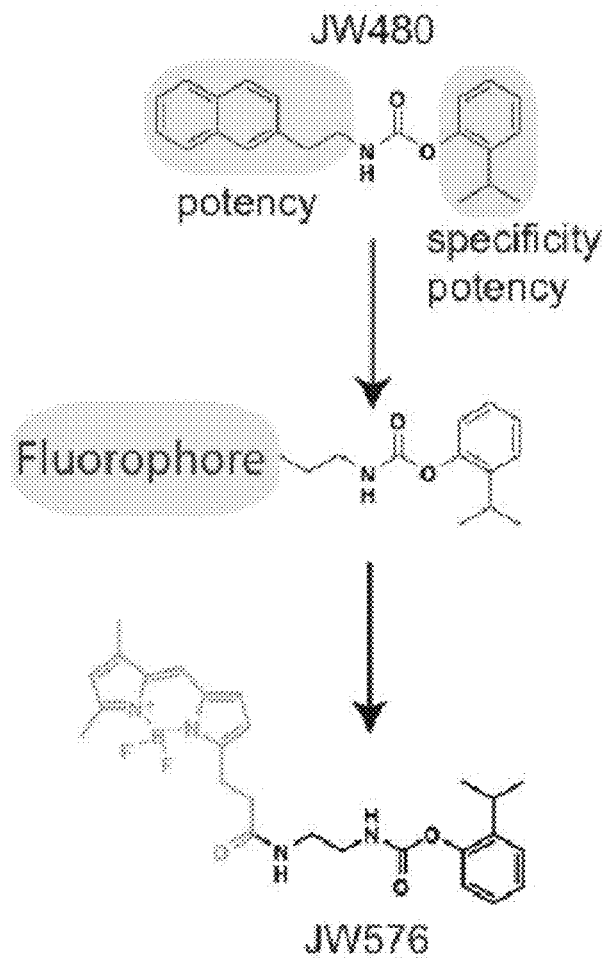
FIG. 14 shows steps in the development of a fluorescent activity-based probe that selectively targets the serine hydrolase KIAA1363. (A) Design of JW576, an activity-based probe that selectively targets KIAA1363. (B) Excitation and emission spectra of JW576. (C) Competitive ABPP profiling of PC3 cells in situ. (D) Time-course of KIAA1363 labeling by JW576 (1 μM) in PC3 cells. (E) Labeling of recombinant KIAA1363 by JW576. Mock- or KIAA1363-transfected COS7 cells were treated with JW576 (0.1 μM) with or without JW480 competitor (1 μM) for 2 hr. (F) Inhibition of 2-AcMAGE hydrolysis activity of KIAA1363 in PC3 and SKOV3 cells treated in situ with JW576.
Figure 14B:
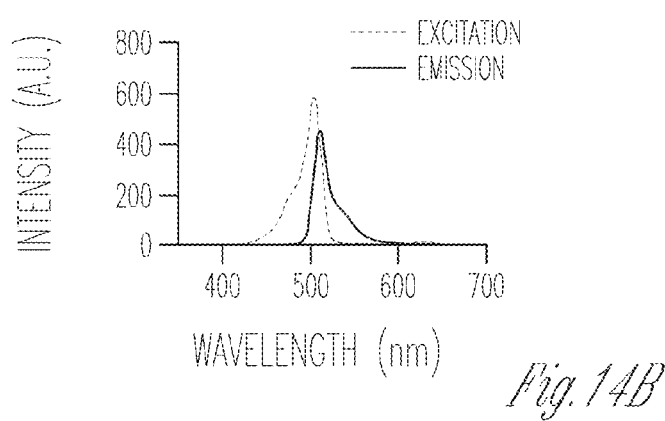

Of the types of fluorophores that could be incorporated into a KIAA1363-selective probe, fluorophores of comparable size, shape, and hydrophobicity as a naphthyl group were chosen. More specifically, a fluorophore of BODIPY was selected owing to its similar overall size and hydrophobicity, JW576, wherein the BODIPY fluorophore was appended to the parent carbamate structure through a propylamide linker (FIG. 14a). Excitation and emission spectra of JW576 revealed maxima at 505 nm and 512 nm, respectively (FIG. 14b). These results indicated that the embedded fluorophore retains the spectral properties of the parent BODIPY compound and should be suitable for fluorescence detection of KIAA1363 and any other potential JW576-reactive proteins. Similar results can be obtained using analogs of the BODIPY structural class, or using coumarin based fluorophores, examples of which are provided below.

Figure 14C:
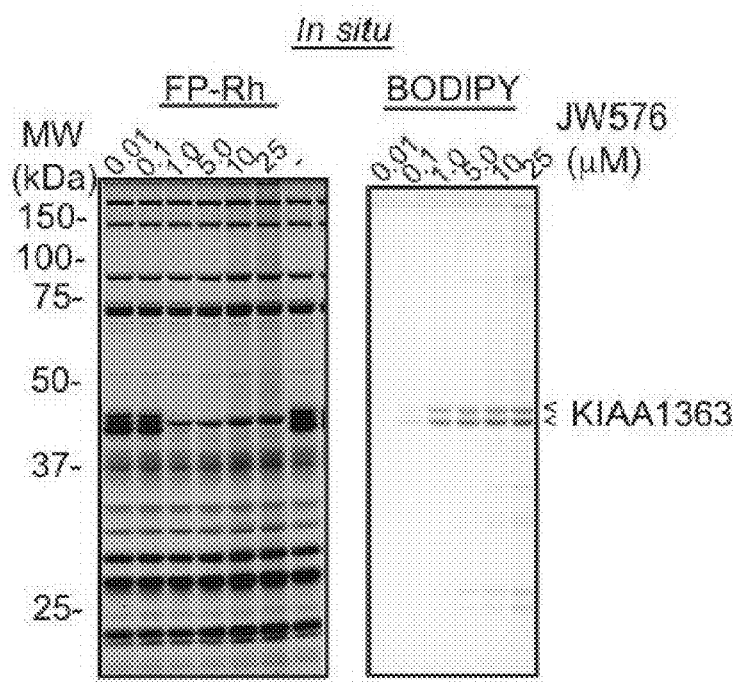
Figure 14D:
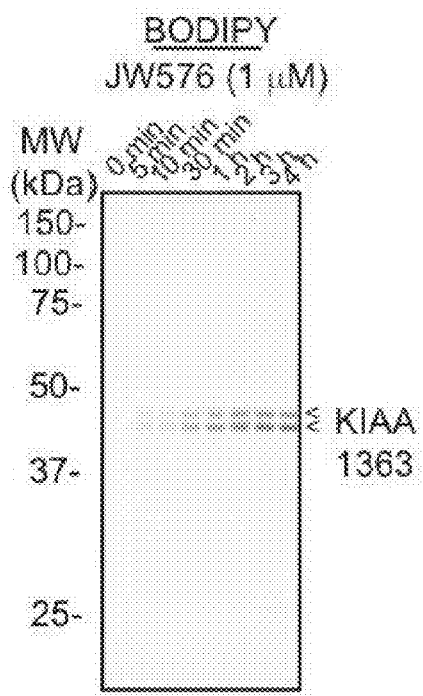
Figure 14E:
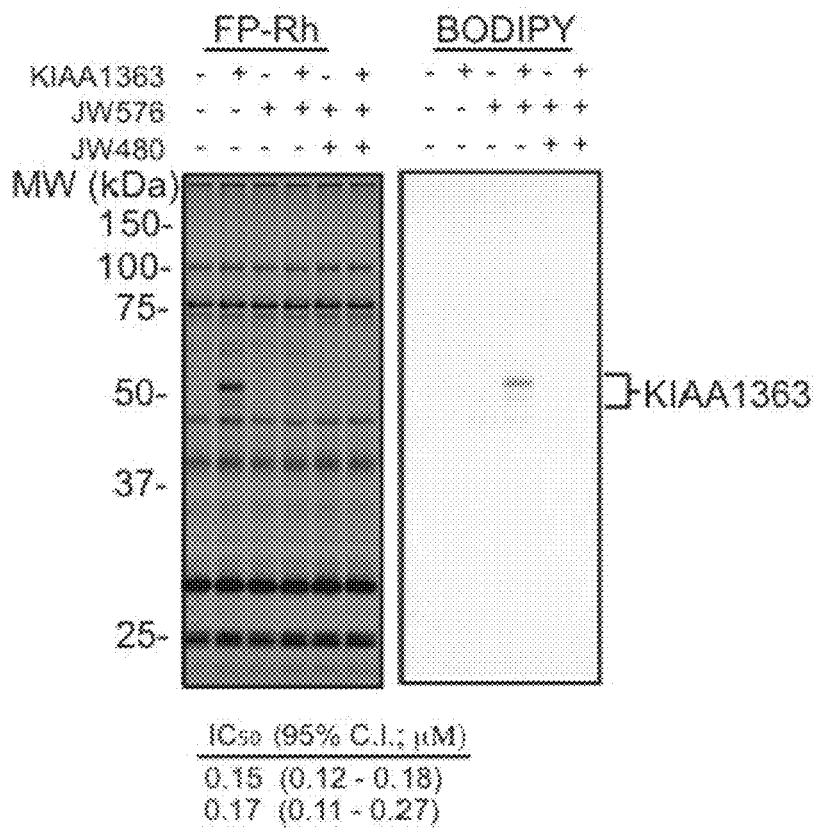
Figure 14F:
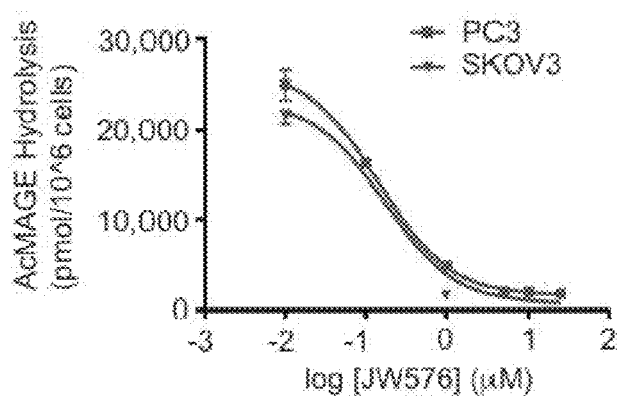

We first evaluated whether JW576 specifically targeted KIAA1363 by performing competitive ABPP with the serine hydrolase-directed probe fluorophosphonate-rhodamine (FP-Rh) (M. P. Patrcelli, D. K. Giang, L. M. Stamp, J. J. Burbaum, *Proteomics* 2001, 1, 1067-1071.). PC3 cancer cells, which have high endogenous KIAA1363 levels (see J. W. Chang, D. K. Nomura, B. F. Cravatt, *Chem Biol* 2011, 18, 476-484), were treated with JW576 in situ (0.01-25 µM for 4 hr), after which cells were homogenized, treated with FP-Rh (1 µM), and analyzed by gel-based ABPP. JW576 was found to selectively inhibit both ~40-45 kDa glycoforms of KIAA1363 with an $IC_{50}$ value of 0.34±0.15 µM (FIG. 14c). Re-scanning of the gel on the BODIPY fluorescence channel confirmed that JW576 inhibition of FP-Rh labeling of KIAA1363 was paralleled by the appearance of a JW576-KIAA1363 covalent adduct (FIG. 14c). Importantly, scanning for BODIPY fluorescence also permitted detection of any other JW576-protein adducts, which were only observed at trace levels and at high concentrations of JW576 (≥5 µM) above the $IC_{50}$ value for KIAA1363 labeling (FIG. 14c). Similar profiles were observed for JW576 in PC3 cell lysates and in other cancer cell lines. KIAA1363 inhibition and labeling by JW576 (1 µM) were also found to be time-dependent, with near-complete target modification and negligible off-target interactions observed within an hour in living PC3 cells (FIG. 14d). We also confirmed specific labeling in COS7 cells transfected with either a mock- or KIAA1363-expressing plasmid, where JW576-labeled KIAA1363 signals were abrogated by pretreatment with JW480 (FIG. 14e). Finally, we found that JW576 blocked KIAA1363 activity in cancer cells using a C16:0 2-acetyl MAGE substrate hydrolysis assay (FIG. 14f), which provided similar in situ $IC_{50}$ values (0.15-0.17 µM) as competitive ABPP assays. Collectively, these data confirmed that JW576 serves as a potent and selective fluorescent inhibitor for KIAA1363 in cancer cells.

We next assessed whether JW576 could be used to image KIAA1363 activity in cancer cells by confocal fluorescence microscopy. PC3 cells were treated with JW576 (0.5 µM) for 0.5-4 hr and imaged on BODIPY and DAPI channels to detect retained JW576 signals and nuclear DNA, respectively. Significant, time-dependent increases in BODIPY fluorescence were observed throughout the cancer cell body, and these signals were blocked by co-treatment with 10×JW480 inhibitor. These results indicated that the observed BODIPY fluorescence signals reflect specific labeling of KIAA1363 by JW576, as opposed to non-specific retention of the compound. Also supporting this conclusion, gel-based ABPP showed specific, time-dependent and JW480-sensitive labeling of KIAA1363 by JW576. With the parameters for fluorescence imaging established, we performed confocal microscopy experiments in three aggressive human cancer cell lines from distinct tumors of origin—prostate (PC3), breast (231MFP) and ovarian (SKOV3)—all of which are known to express high levels of KIAA1363 (D. K. Nomura, J. Z. Long, S. Niessen, H. S. Hoover, S. Ng, B. F. Cravatt, Cell 2010, 140, 49-61; J. W. Chang, D. K. Nomura, B. F. Cravatt, Chem Biol 2011, 18, 476-484.). In each case, strong, JW480-sensitive intracellular staining was observed for JW576-treated cells. Similarly strong intracellular staining was detected in COS7 cells transfected with a KIAA1363 cDNA, but not in mock-transfected COS7 cells. These results establish the utility of JW576 as a fluorescent imaging probe for direct visualization of active KIAA1363 in cells and indicate that this enzyme is localized predominantly to intracellular membrane compartments in cancer cells.

In addition to spatial mapping of active KIAA1363 in cancer cells, we wondered whether JW576 could be used for temporal tracking of the cellular turnover of KIAA1363. For this study, we followed the general protocols for traditional pulse-chase experiments, but used JW576 treatment in place of metabolic incorporation of radiolabeled amino acids. Two different human cancer cell lines (SKOV3 and DU145) were pulse-treated with JW576 (5 µM) for 10 minutes, washed with fresh media, and then incubated with media containing an excess of JW480 to quench any unreacted KIAA1363. Cell proteomes were then harvested at the indicated times over 48 hours and KIAA1363 activity levels measured by gel-based ABPP (FIG. 15a, c). Time-dependent reductions in KIAA1363 signals were observed in both cell lines and fitting the quantified band intensities to an exponential decay model provided half-life estimates of 14.2 and 22.9 hours for KIAA1363 in SKOV3 and DU145 cells, respectively (FIG. 15b, d).

We tested whether JW576 could label KIAA1363 in C57Bl/6J mice by treating animals with escalating doses of the compound (5-40 mg/kg, i.p.) for 4 hr. Mice were then sacrificed and proteomes from heart, a tissue that expresses high levels of KIAA1363, were analyzed by gel-based ABPP. Scanning on the BODIPY channel revealed significant labeling of KIAA1363 at all tested doses (FIG. 16a). The rate of in vivo labeling of KIAA1363 by JW576 was fast, with near-maximal signals being observed as early as 30 min post-dosing (FIG. 16b). JW576 maintained good selectivity for KIAA1363 in vivo, with only a single, faint additional probe target (70 kDa protein) being detected in the heart proteome (FIGS. 16a, b). We confirmed that the 40-45 kDa JW576-labeled protein doublet corresponded to KIAA1363 by repeating in vivo treatments in wild-type (WT) and mKIAA1363 knockout (KO) mice (FIG. 16c). We also analyzed these KIAA1363-WT and KO heart proteomes by competitive ABPP with FP-Rh, which revealed substantial reductions in KIAA1363 activity in WT mice treated with JW576 and complete absence of KIAA1363 signals in KO mice (FIG. 16c). These competitive ABPP gels also provided evidence that the 70 kDa protein labeled by JW576 was itself a serine hydrolase (FIG. 16c), likely corresponding to the blood carboxylesterase ES1, which is a known off-target of JW480, the parent carbamate inhibitor from which JW576 was derived. Overall, these studies confirm that JW576 can be used to rapidly label KIAA1363 activity with good selectivity in vivo.

Examples of $R^1$ Fluorophores

A $R^1$ group fluorophore can be any suitable fluorescent function group that can be coupled, such as via a spacer moiety, to the nitrogen atom of the carbamate group. It is believed that irreversible inhibition of the serine hydrolase occurs via acylation of the enzyme's active site serine residue by the aminoacyl group of the carbamate, with loss of the alkoxy group. Accordingly, a fluorescent probe of the invention bears the fluorophore on the carbamate amino group. Preferably, a spatially flat, aromatic group such as a fluorescent heteroaryl group, acts as the fluorophore. It is within ordinary skill to prepare and test a fluorescent probe as disclosed and claimed herein using the procedures discussed herein in conjunction with ordinary skill.

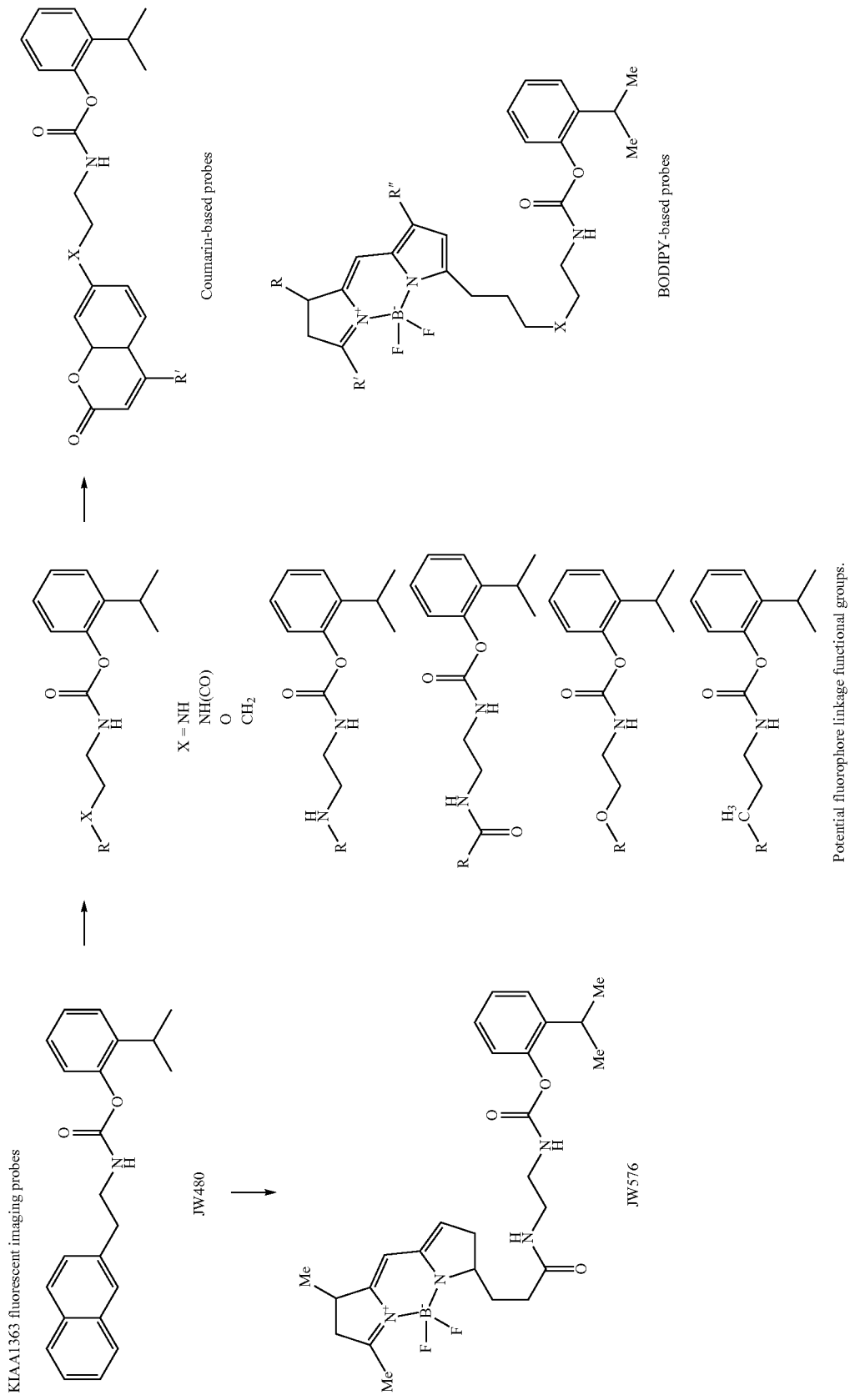

Some examples of fluorophores suitable for use in fluorescent carbamate probes of the invention, having potent serine hydrolase inhibitory activity, include BODIPY based probes and coumarin based probes, examples of which are shown below. They are bonded via a linker at, for example, the position indicated by the wavy line, to the nitrogen atom of the carbamate group, as shown in the following formula, wherein R is a fluorophore group,

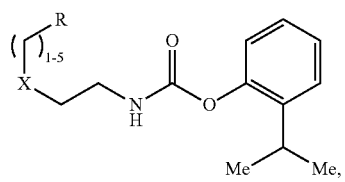

wherein X can be NH, NHC(=O), O, $CH_2$, C(=O), or the like. Groups other than the o-isopropylphenyl group shown, e.g., other aryl and heteroaryl groups, can be disposed as group $Ar^1$ of formula (I), such as are disclosed herein.

Some specific examples of BODIPY-type fluorophores include:

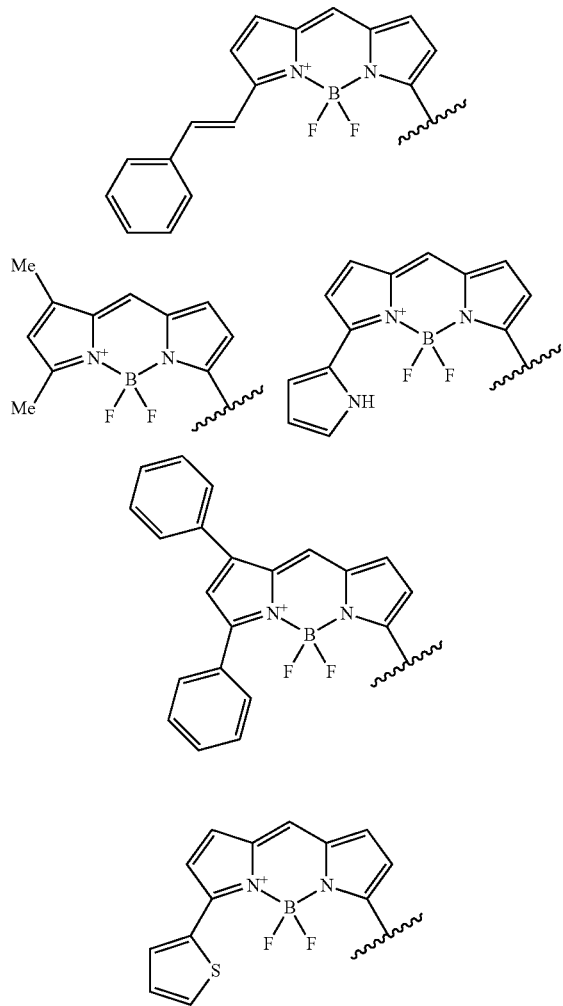

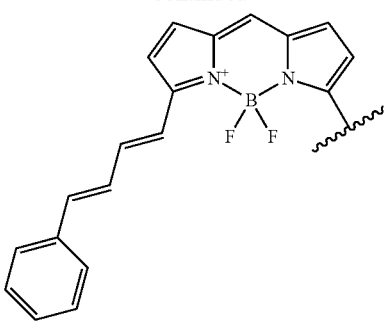

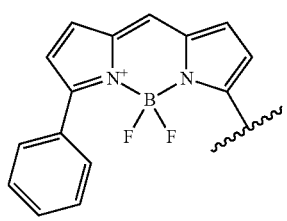

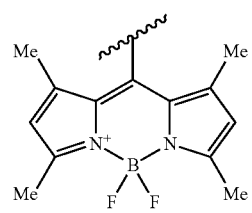

Alternatively, coumarin based fluorophores can be used, such as

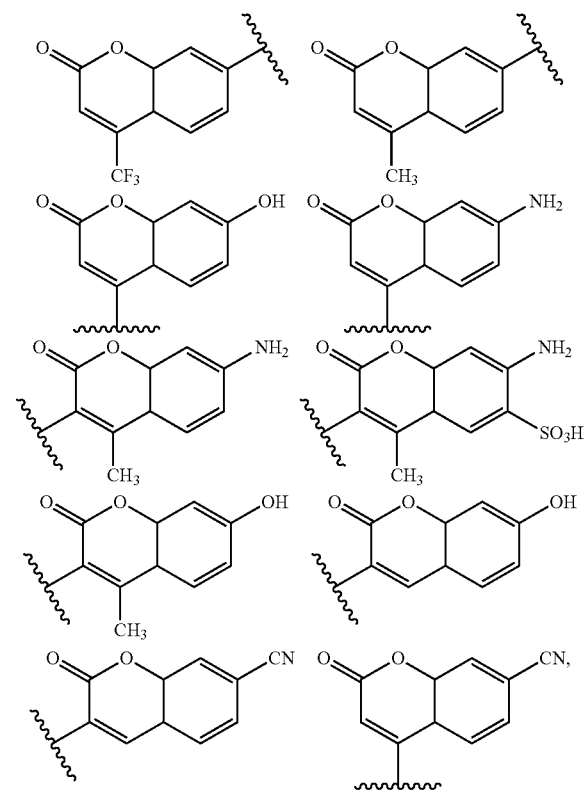

wherein a wavy line indicates a point of bonding to the linker moiety connecting the fluorophore to the carbamate nitrogen atom.

Synthetic Methods for Fluorescent Probes

Carbamates of formula (I) wherein the R1 group comprises a fluorophore can be prepared analogously to other carbamates of formula (I) disclosed herein, using ordinary skill in synthetic organic chemistry to select appropriate precursors and couple them to yield the carbamate.

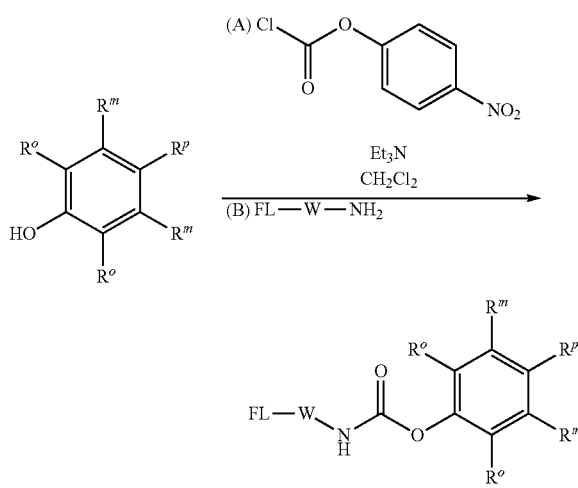

For example, a phenol bearing the desired substituent pattern of group $Ar^1$ can be selected and carbonylated, such as by reaction with an activated chloroformate like p-nitrochloroformate. The activated carbonate can then be reacted with an amino-terminal FL-W group, such as can be selected by a person of ordinary skill in the art. For example, an aminoethyl BODIPY analog can be coupled with the activated carbonate intermediate to yield a compound of formula (I) wherein $R^1$ is FL-W, the fluorophore-linker moiety. Alternatively, coupling a activated carboxylated fluorescent molecule with an amino-functional carbamate can be used, as shown in the following scheme.

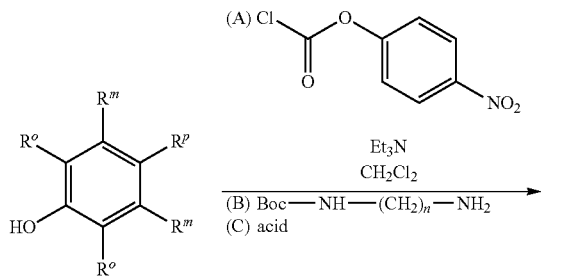

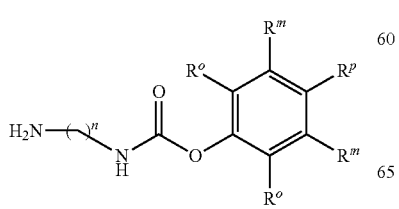

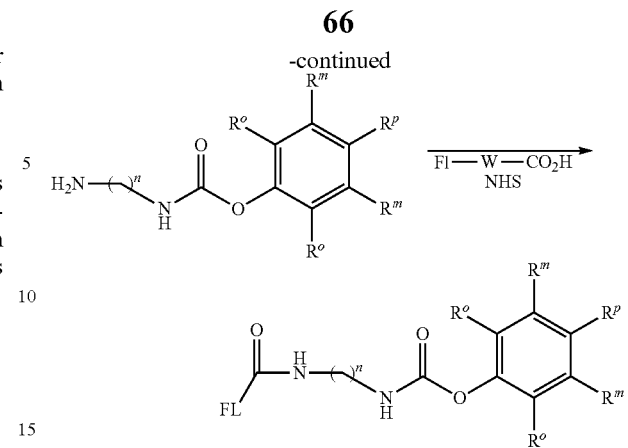

Coumarin based fluorophores can be incorporated into compounds of the invention of formula (I) by a variety of methods apparent to persons of skill in the art. A scheme is shown below.

Representative Coumarin-Containing Fluorescent Probe Synthetic Scheme

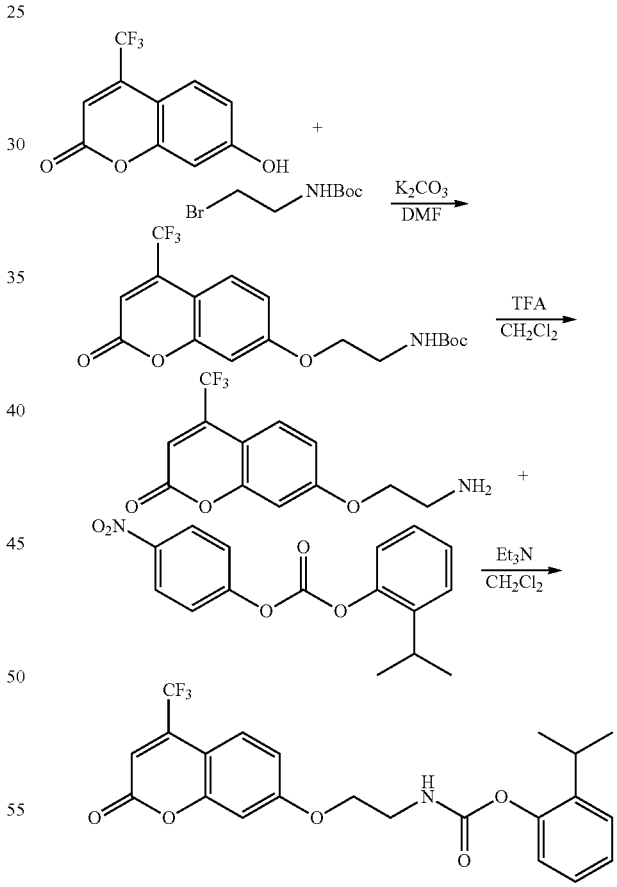

EXAMPLES

Synthetic Methods

General Synthetic Methods.

All chemicals were obtained from Aldrich, Acros, Fisher, Fluka or Maybridge and were used without further purification, except where noted. Dry solvents (dichloromethane) and triethylamine were obtained by passing these through activated alumina columns. All reactions were carried out under an inert nitrogen atmosphere using oven-baked glassware unless otherwise noted. Flash chromatography was performed using 230-400 mesh silica gel 60. $^1$H spectra were recorded on a Varian Mercury-300 MHz spectrometer. Chemical shifts are reported in δ values relative to tetramethylsilane, and coupling constants (J) are reported in Hz.
Representative Synthetic Scheme $^1$H NMR 300 MHz (CDCl$_3$) δ 7.85 (m, 3H), 7.71 (s, 1H), 7.50 (m, 2H), 7.40 (d, J=8.4 Hz, 1H), 7.29 (m, 1H), 7.19 (m, 2H), 7.04 (d, J=4.9 Hz, 1H), 5.08 (s, 1H), 3.67 (q, J=6.5 Hz, 2H), 3.08 (m, 3H), 1.20 (d, J=6.9 Hz, 6H), HRMS (m/z): [M+H]$^+$ calculated for C$_{22}$H$_{23}$NO$_2$, 334.1801. found, 334.1799.

All other compounds were synthesized according to the above scheme, using appropriate amines and alcohols.

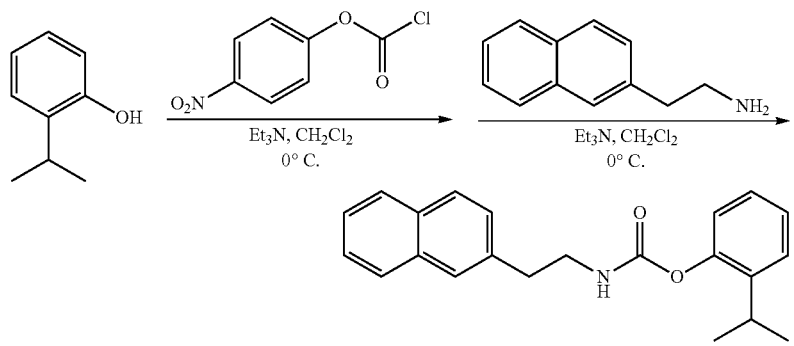

Specific Synthetic Methods 2-isopropylphenyl (2-(naphthalen-2-yl)ethyl)carbamate (JW480)

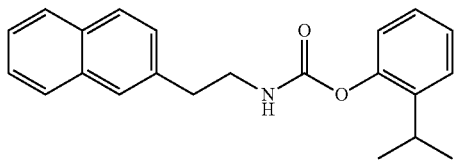 [SMILES: CC(C)c1ccccc1OC(=O)NCCc1ccc2ccccc2c1]

To a solution of 2-isopropylphenol (5.0 g, 36.713 mmol) in dichloromethane (183.0 mL) was added 4-nitrophenyl chloroformate (8.1 g, 40.385 mmol) and Et$_3$N (10.3 mL, 73.426 mmol) at 0° C. After stirring at 0° C. 2 hours, the reaction mixture was treated with 30.0 mL of saturated aqueous NaHCO$_3$ solution. The organic layer was separated and the aqueous layer was extracted with dichloromethane. The combined organic extracts were washed with brine, dried over MgSO$_4$, filtered and concentrated. The crude product was used without further purification. To a solution of crude carbonate intermediate in dichloromethane (150 mL) was added 2-(naphthalen-2-yl)ethanamine (6.9 g, 40.385 mmol) and Et$_3$N (10.3 mL, 73.426 mmol) at 0° C. After stirring at 0° C. 2 hours, the reaction mixture was treated with 30.0 mL of saturated aqueous NaHCO$_3$ solution. The organic layer was separated and the aqueous layer was extracted with dichloromethane. The combined organic extracts were washed with brine, dried over MgSO$_4$, filtered and concentrated. The crude product was purified by flash column chromatography using a 9:1 v/v hexane:ethyl acetate as solvent to afford title compound (11.5 g, 94% yield) as a white solid.

Characterization of Exemplary Compounds

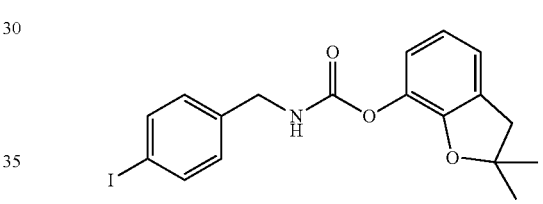

JW147: 2,2-dimethyl-2,3-dihydrobenzofuran-7-yl 4-iodobenzylcarbamate $^1$H NMR 300 MHz (CDCl$_3$) δ 7.71 (d, J=8.2 Hz, 2H), 7.14 (d, J=8.2 Hz, 2H), 7.01 (dd, J=4.1, 10.3 Hz, 2H), 6.81 (m, 1H), 5.42 (s, 1H), 4.43 (d, J=6.1 Hz, 2H), 3.07 (s, 2H), 1.52 (s, 6H), HRMS (m/z): [M+H]$^+$ calculated for C$_{18}$H$_{18}$INO$_3$, 424.0404. found, 424.0400.

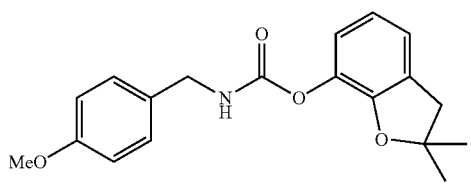 [SMILES: COc1ccc(CNC(=O)Oc2cccc3c2OC(C)(C)C3)cc1]

JW148: 2,2-dimethyl-2,3-dihydrobenzofuran-7-yl 4-methoxybenzylcarbamate $^1$H NMR 300 MHz (CDCl$_3$) δ 7.29 (d, J=9.0 Hz, 2H), 6.98 (d, J=6.1 Hz, 2H), 6.90 (m, 2H), 6.79 (m, 1H), 5.33 (s, 1H), 4.39 (d, J=6.1 Hz, 2H), 3.82 (s, 3H), 3.04 (s, 2H), 1.50 (s, 6H), HRMS (m/z): [M+H]$^+$ calculated for C$_{19}$H$_{21}$NO$_4$, 328.1543. found, 328.1548.

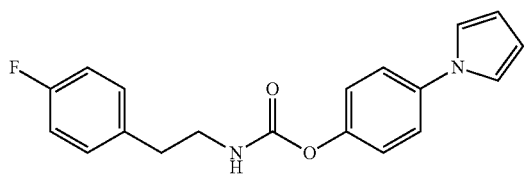 [SMILES: O=C(NCCc1ccc(F)cc1)Oc1ccc(-n2cccc2)cc1]

JW382: 4-(1H-pyrrol-1-yl)phenyl
4-fluorophenethylcarbamate $^1$H NMR 300 MHz (CDCl$_3$) δ 7.36 (m, 2H), 7.20 (m, 4H), 7.05 (m, 4H), 6.34 (m, 2H), 5.04 (s, 1H), 3.53 (q, J=6.1 Hz, 2H), 2.89 (t, J=6.0 Hz, 2H), HRMS (m/z): [M+H]$^+$ calculated for C$_{19}$H$_{17}$FN$_2$O$_2$, 325.1347. found, 325.1341.

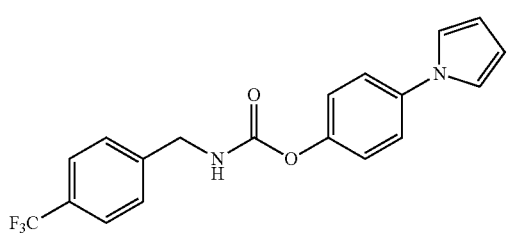 [SMILES: O=C(NCc1ccc(C(F)(F)F)cc1)Oc1ccc(-n2cccc2)cc1]

JW383: 4-(1H-pyrrol-1-yl)phenyl
4-(trifluoromethyl)benzylcarbamate $^1$H NMR 300 MHz (CDCl$_3$) δ 7.65 (d, J=8.9 Hz, 2H), 7.50 (d, J=8.8 Hz, 2H), 7.40 (d, J=9.0 Hz, 2H), 7.22 (d, J=8.8 Hz, 2H), 7.06 (m, 2H), 6.36 (m, 2H), 5.47 (s, 1H), 4.55 (d, J=6.0 Hz, 2H), HRMS (m/z): [M+H]$^+$ calculated for C$_{19}$H$_{15}$F$_3$N$_2$O$_2$, 361.1158. found, 361.1153.

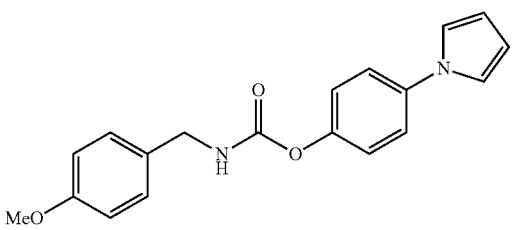 [SMILES: COc1ccc(CNC(=O)Oc2ccc(-n3cccc3)cc2)cc1]

JW384: 4-(1H-pyrrol-1-yl)phenyl
4-methoxybenzylcarbamate $^1$H NMR 300 MHz (CDCl$_3$) δ 7.37 (d, J=8.8 Hz, 2H), 7.29 (d, J=6.1 Hz, 2H), 7.20 (d, J=9.1 Hz, 2H), 7.04 (m, 2H), 6.90 (m, 2H), 6.34 (m, 2H), 5.29 (s, 1H), 4.40 (d. J=6.3 Hz, 2H), 3.82 (s, 3H), HRMS (m/z): [M+H]$^+$ calculated for C$_{19}$H$_{18}$N$_2$O$_3$, 323.139. found, 323.1385.

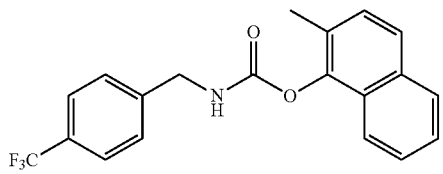 [SMILES: Cc1ccc2ccccc2c1OC(=O)NCc1ccc(C(F)(F)F)cc1]

JW385: 2-methylnaphthalen-1-yl
4-(trifluoromethyl)benzylcarbamate $^1$H NMR 300 MHz (CDCl$_3$) δ 7.77 (m, 2H), 7.60 (m, 3H), 7.45 (m, 4H), 7.30 (d, J=6.3 Hz, 1H), 5.62 (s, 1H), 4.55 (d, J=6.1 Hz, 2H), 2.35 (s, 3H). HRMS (m/z): [M+H]$^+$ calculated for C$_{20}$H$_{16}$F$_3$NO$_2$, 360.1206. found, 360.1201.

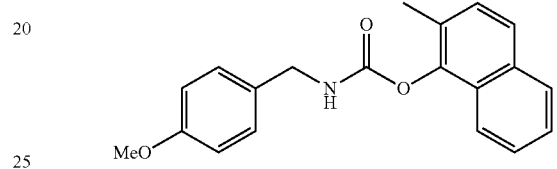

JW386: 2-methylnaphthalen-1-yl
4-methoxybenzylcarbamate $^1$H NMR 300 MHz (CDCl$_3$) δ 7.78 (m, 2H), 7.62 (d, J=8.9 Hz, 1H), 7.42 (m, 2H), 7.29 (m, 3H), 6.88 (d, J=8.8 Hz, 2H), 5.45 (s, 1H), 4.42 (d, J=6.0 Hz, 2H), 3.79 (s, 3H), 2.34 (s, 3H), HRMS (m/z): [M+H]$^+$ calculated for C$_{20}$H$_{19}$NO$_3$, 322.1438. found, 322.1435.

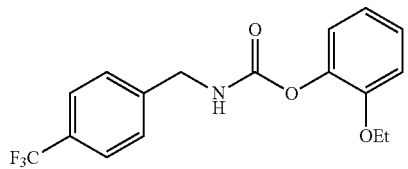 [SMILES: CCOc1ccccc1OC(=O)NCc1ccc(C(F)(F)F)cc1]

JW387: 2-ethoxyphenyl
4-(trifluoromethyl)benzylcarbamate $^1$H NMR 300 MHz (CDCl$_3$) δ 7.57 (d, J=5.8 Hz, 2H), 7.45 (d, J=8.8 Hz, 2H), 7.10 (m, 2H), 6.89 (m, 2H), 5.44 (s, 1H), 4.48 (d, J=6.1 Hz, 2H), 4.02 (q, J=6.3 Hz, 2H), 1.32 (t, J=6.5 Hz, 3H), HRMS (m/z): [M+H]$^+$ calculated for C$_{17}$H$_{16}$F$_3$NO$_3$, 340.1155. found, 340.1158.

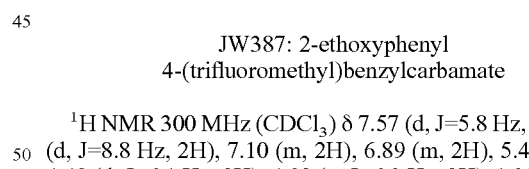

JW388: 2-ethoxyphenyl 4-methoxybenzylcarbamate $^1$H NMR 300 MHz (CDCl$_3$) δ 7.22 (d, J=9.2 Hz, 1H), 7.05 (m, 2H), 6.85 (m, 4H), 6.75 (d, J=9.0 Hz, 1H), 5.29 (s, 1H), 4.34 (d, J=6.4 Hz, 2H), 4.00 (q, J=6.1 Hz, 2H), 3.75 (s, 3H), 1.30 (t, J=6.0 Hz, 3H), HRMS (m/z): [M+H]⁺ calculated for C₁₇H₁₉NO₄, 302.1387. found, 302.1389.

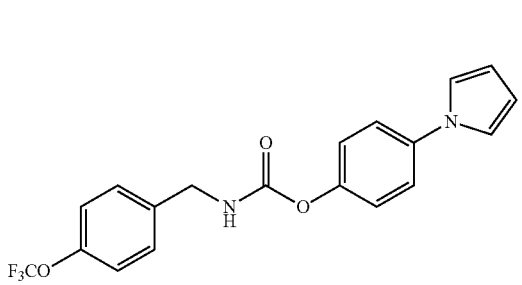 [SMILES: O=C(NCc1ccc(OC(F)(F)F)cc1)Oc1ccc(-n2cccc2)cc1]

JW389: 4-(1H-pyrrol-1-yl)phenyl 4-(trifluoromethoxy)benzylcarbamate

¹H NMR 300 MHz (CDCl₃) δ 7.40 (m, 4H), 7.27 (m, 1H), 7.22 (m, 3H), 7.05 (t, J=3.2 Hz, 2H), 6.36 (t, J=3.2 Hz, 2H), 5.40 (s, 1H), 4.49 (d, J=6.3 Hz, 2H), HRMS (m/z): [M+H]⁺ calculated for C₁₉H₁₅F₃N₂O₃, 377.1107. found, 377.1107.

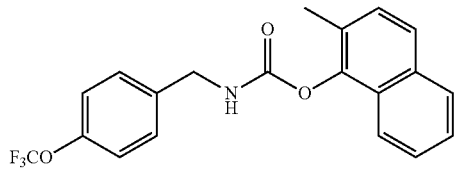

JW390: 2-methylnaphthalen-1-yl 4-(trifluoromethoxy)benzylcarbamate

¹H NMR 300 MHz (CDCl₃) δ 7.83 (m, 2H), 7.67 (d, J=8.8 Hz, 1H), 7.46 (m, 4H), 7.34 (d, J=6.3 Hz, 1H), 7.26 (m, 1H), 7.23 (m, 1H), 5.60 (s, 1H), 4.53 (d, J=6.1 Hz, 2H), 2.38 (s, 3H), HRMS (m/z): [M+H]⁺ calculated for C₂₀H₁₆F₃NO₃, 376.1155. found, 376.1155.

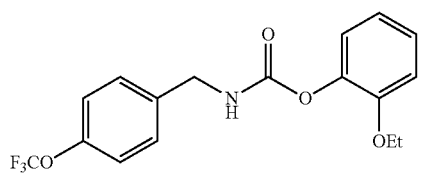 [SMILES: CCOc1ccccc1OC(=O)NCc1ccc(OC(F)(F)F)cc1]

JW391: 2-ethoxyphenyl 4-(trifluoromethoxy)benzylcarbamate

¹H NMR 300 MHz (CDCl₃) δ 7.42 (d, J=9.0 Hz, 2H), 7.18 (m, 4H), 6.95 (m, 2H), 5.45 (s, 1H), 4.48 (d, J=6.1 Hz, 2H), 4.08 (q, J=5.9 Hz, 2H), 1.38 (t, J=6.1 Hz, 3H), HRMS (m/z): [M+H]⁺ calculated for C₁₇H₁₆F₃NO₄, 356.1104. found, 356.1102.

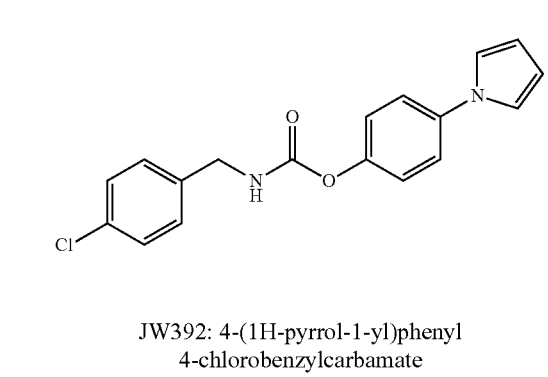

JW392: 4-(1H-pyrrol-1-yl)phenyl 4-chlorobenzylcarbamate

¹H NMR 300 MHz (CDCl₃) δ 7.35 (m, 6H), 7.21 (m, 2H), 7.05 (m, 2H), 6.35 (m, 2H), 5.37 (s, 1H), 4.45 (d, J=6.4 Hz, 2H), HRMS (m/z): [M+H]⁺ calculated for C₁₈H₁₅ClN₂O₂, 327.0895. found, 327.0893.

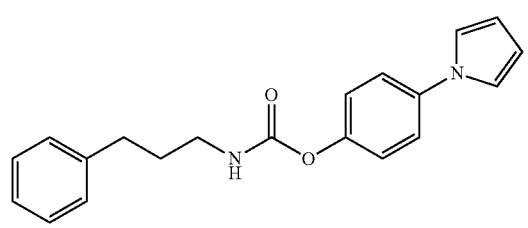 [SMILES: O=C(NCCCc1ccccc1)Oc1ccc(-n2cccc2)cc1]

JW393: 4-(1H-pyrrol-1-yl)phenyl (3-phenylpropyl)carbamate

¹H NMR 300 MHz (CDCl₃) δ 7.37 (m, 2H), 7.28 (m, 3H), 7.20 (m, 4H), 7.05 (m, 2H), 6.34 (m, 2H), 5.04 (s, 1H), 3.33 (q, J=6.2 Hz, 2H), 2.72 (t, J=5.8 Hz, 2H), 1.95 (m, 2H), HRMS (m/z): [M+H]⁺ calculated for C₂₀H₂₀N₂O₂, 321.1597. found, 321.1599.

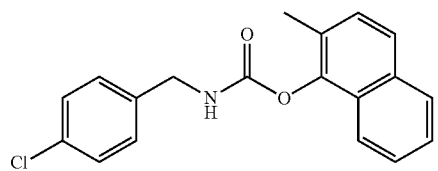 [SMILES: Cc1ccc2ccccc2c1OC(=O)NCc1ccc(Cl)cc1]

JW395: 2-methylnaphthalen-1-yl 4-chlorobenzylcarbamate

¹H NMR 300 MHz (CDCl₃) δ 7.86 (m, 2H), 7.70 (d, J=8.9 Hz, 1H), 7.51 (m, 3H), 7.38 (m, 4H), 5.62 (s, 1H), 4.53 (d, J=6.0 Hz, 2H), 2.42 (s, 3H), HRMS (m/z): [M+H]⁺ calculated for C₁₉H₁₆ClNO₂, 326.0942. found, 326.0938.

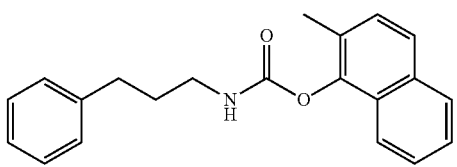 [SMILES: Cc1ccc2ccccc2c1OC(=O)NCCCc1ccccc1]

JW396: 2-methylnaphthalen-1-yl (3-phenylpropyl)carbamate $^1$H NMR 300 MHz (CDCl$_3$) δ 7.84 (t, J=5.9 Hz, 2H), 7.66 (d, J=6.2 Hz, 1H), 7.47 (m, 2H), 7.33 (m, 3H), 7.23 (m, 3H), 5.25 (s, 1H), 3.38 (q, J=6.1 Hz, 2H), 2.75 (t, J=6.7 Hz, 2H), 2.39 (s, 3H), 1.98 (m, 2H), HRMS (m/z): [M+H]$^+$ calculated for C$_{21}$H$_{21}$NO$_2$, 320.1645. found, 320.1635.

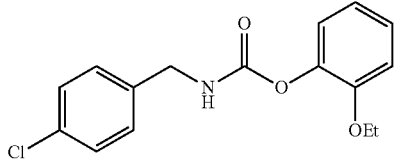 [SMILES: CCOc1ccccc1OC(=O)NCc1ccc(Cl)cc1]

JW398: 2-ethoxyphenyl 4-chlorobenzylcarbamate $^1$H NMR 300 MHz (CDCl$_3$) δ 7.35 (m, 4H), 7.17 (m, 2H), 6.97 (m, 2H), 5.44 (s, 1H), 4.47 (d, J=6.0 Hz, 2H), 4.08 (q, J=5.8 Hz, 2H), 1.42 (t. J=6.0 Hz, 3H), HRMS (m/z): [M+H]$^+$ calculated for C$_{16}$H$_{16}$ClNO$_3$, 306.0891. found, 306.0889.

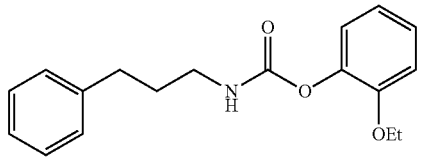 [SMILES: CCOc1ccccc1OC(=O)NCCCc1ccccc1]

JW399: 2-ethoxyphenyl(3-phenylpropyl)carbamate $^1$H NMR 300 MHz (CDCl$_3$) δ 7.30 (m, 2H), 7.18 (m, 5H), 6.94 (m, 2H), 5.09 (s, 1H), 4.07 (q, J=6.3 Hz, 2H), 3.32 (q, J=6.1 Hz, 2H), 2.72 (t, J=6.0 Hz, 2H), 1.93 (m, 2H), 1.40 (t, J=5.8 Hz, 3H), HRMS (m/z): [M+H]$^+$ calculated for C$_{18}$H$_{21}$NO$_3$, 300.1594. found, 300.1593.

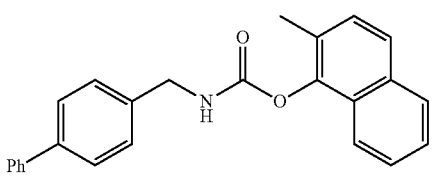

JW405: 2-methylnaphthalen-1-yl([1,1'-biphenyl]-4-ylmethyl)carbamate $^1$H NMR 300 MHz (CDCl$_3$) δ 7.86 (m, 2H), 7.64 (m, 5H), 7.48 (m, 6H), 7.37 (m, 2H), 5.61 (s, 1H), 4.59 (d, J=6.0 Hz, 2H), 2.42 (s, 3H), HRMS (m/z): [M+H]$^+$ calculated for C$_{25}$H$_{21}$NO$_2$, 368.1645. found, 368.1640.

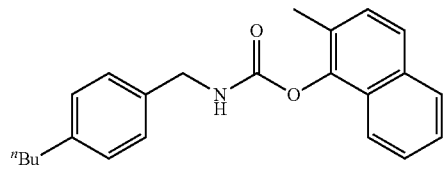

JW406: 2-methylnaphthalen-1-yl 4-butylbenzylcarbamate $^1$H NMR 300 MHz (CDCl$_3$) 7.85 (m, 2H), 7.67 (d, J=8.8 Hz, 1H), 7.47 (m, 2H), 7.33 (m, 3H), 7.22 (m, 2H), 5.53 (s, 1H), 4.51 (d, J=6.1 Hz, 2H), 2.64 (t, J=5.9 Hz, 2H), 2.40 (s, 3H), 1.63 (m, 2H), 1.38 (m, 2H), 0.95 (t, J=8.6 Hz, 3H), HRMS (m/z): [M+H]$^+$ calculated for C$_{23}$H$_{25}$NO$_2$, 348.1958. found, 348.1954.

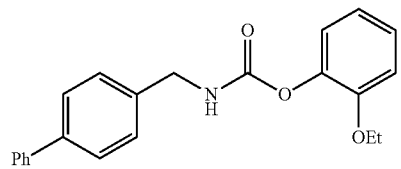

JW408: 2-ethoxyphenyl([1,1'-biphenyl]-4-ylmethyl)carbamate $^1$H NMR 300 MHz (CDCl$_3$) δ 7.61 (m, 4H), 7.47 (m, 4H), 7.37 (m, 1H), 7.16 (m, 2H), 6.96 (m, 2H), 5.45 (s, 1H), 4.53 (d, J=6.0 Hz, 2H), 4.10 (q, J=5.9 Hz, 2H), 1.42 (t, J=6.0 Hz, 3H), HRMS (m/z): [M+H]$^+$ calculated for C$_{22}$H$_{21}$NO$_3$, 348.1594. found, 348.1596.

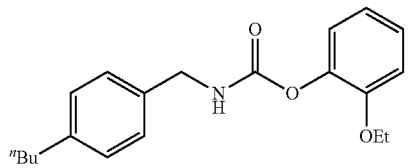

JW409: 2-ethoxyphenyl 4-butylbenzylcarbamate $^1$H NMR 300 MHz (CDCl$_3$) δ 7.29 (m, 2H), 7.17 (m, 3H), 7.11 (m, 1H), 6.93 (m, 2H), 5.34 (s, 1H), 4.43 (d, J=6.3 Hz, 2H), 4.06 (q, J=6.2 Hz, 2H), 2.61 (t, J=8.3 Hz, 2H), 1.59 (m, 2H), 1.36 (m, 5H), 0.93 (t, J=8.4 Hz, 3H), HRMS (m/z): [M+H]$^+$ calculated for C$_{20}$H$_{25}$NO$_3$, 328.1907. found, 328.1903.

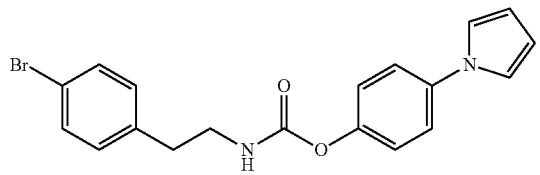 [SMILES: O=C(NCCc1ccc(Br)cc1)Oc1ccc(-n2cccc2)cc1]

JW412: 4-(1H-pyrrol-1-yl)phenyl 4-bromophenethylcarbamate $^1$H NMR 300 MHz (CDCl$_3$) δ 7.47 (m, 2H), 7.36 (m, 2H), 7.14 (m, 4H), 7.04 (t, J=3.2 Hz, 2H), 6.34 (t, J=3.0 Hz, 2H), 5.03 (s, 1H), 3.53 (q, J=6.1 Hz, 2H), 2.87 (t. J=6.0 Hz, 2H). HRMS (m/z): [M+H]$^+$ calculated for C$_{19}$H$_{17}$BrN$_2$O$_2$, 385.0546. found, 385.0547.

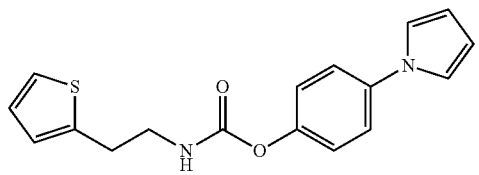 [SMILES: O=C(NCCc1cccs1)Oc1ccc(-n2cccc2)cc1]

JW413: 4-(1H-pyrrol-1-yl)phenyl (2-(thiophen-2-yl)ethyl)carbamate $^1$H NMR 300 MHz (CDCl$_3$) δ 7.38 (m, 2H), 7.20 (m, 3H), 7.05 (m, 2H), 6.99 (m, 1H), 6.90 (m, 1H), 6.34 (m, 2H), 5.18 (s, 1H), 3.58 (q, J=6.5 Hz, 2H), 3.14 (t, J=6.5 Hz, 2H), HRMS (m/z): [M+H]$^+$ calculated for C$_{17}$H$_{16}$N$_2$O$_2$S, 313.1005. found, 313.1009.

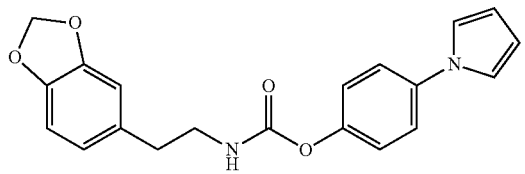 [SMILES: O=C(NCCc1ccc2c(c1)OCO2)Oc1ccc(-n2cccc2)cc1]

JW414: 4-(1H-pyrrol-1-yl)phenyl (2-(benzo[d][1,3]dioxol-5-yl)ethyl)carbamate $^1$H NMR 300 MHz (CDCl$_3$) δ 7.37 (d, J=8.9 Hz, 2H), 7.17 (d, J=8.9 Hz, 2H), 7.04 (t, J=2.2 Hz, 2H), 6.73 (m, 3H), 6.34 (dd, J=3.2, 5.4 Hz, 2H), 5.96 (s, 2H), 5.05 (s, 1H), 3.51 (q, J=6.8 Hz, 2H), 2.83 (t, J=6.8 Hz, 2H), HRMS (m/z): [M+H]$^+$ calculated for C$_{20}$H$_{11}$N$_2$O$_4$, 351.1339. found, 351.1346.

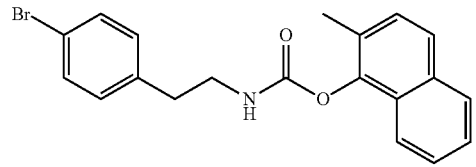 [SMILES: Cc1ccc2ccccc2c1OC(=O)NCCc1ccc(Br)cc1]

JW415: 2-methylnaphthalen-1-yl 4-bromophenethylcarbamate $^1$H NMR 300 MHz (CDCl$_3$) δ 7.80 (d, J=7.6 Hz, 1H), 7.73 (d, J=8.3 Hz, 1H), 7.64 (d, J=8.3 Hz, 1H), 7.46 (m, 4H), 7.31 (d, J=8.3 Hz, 1H), 7.14 (d, J=8.3 Hz, 2H), 5.22 (s, 1H), 3.58 (q, J=6.7 Hz, 2H), 2.89 (t, J=6.8 Hz, 2H), 2.32 (s, 3H), HRMS (m/z): [M+H]$^+$ calculated for C$_{20}$H$_{18}$BrNO$_2$, 384.0594. found, 384.0593.

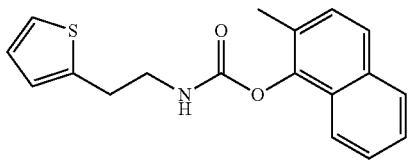 [SMILES: Cc1ccc2ccccc2c1OC(=O)NCCc1cccs1]

JW416: 2-methylnaphthalen-1-yl (2-(thiophen-2-yl)ethyl)carbamate $^1$H NMR 300 MHz (CDCl$_3$) δ 7.82 (d, J=8.3 Hz, 2H), 7.66 (d, J=8.4 Hz, 1H), 7.46 (m, 2H), 7.32 (m, 1H), 7.23 (dd, J=0.6, 5.1 Hz, 1H), 7.01 (dd, J=3.5, 5.1 Hz, 1H), 6.93 (d, J=3.3 Hz, 1H), 5.40 (s, 1H), 3.63 (q, J=6.4 Hz, 2H), 3.17 (t, J=6.5 Hz, 2H), 2.37 (s, 3H), HRMS (m/z): [M+H]$^+$ calculated for C$_{18}$H$_{17}$NO$_2$S, 312.1053. found, 312.1058.

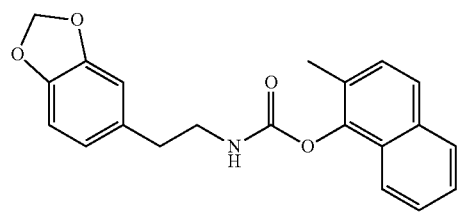 [SMILES: Cc1ccc2ccccc2c1OC(=O)NCCc1ccc2c(c1)OCO2]

JW417: 2-methylnaphthalen-1-yl (2-(benzo[d][1,3]dioxol-5-yl)ethyl)carbamate $^1$H NMR 300 MHz (CDCl$_3$) δ 7.79 (t, J=6.2 Hz, 2H), 7.64 (d, J=9.1 Hz, 1H), 7.45 (m, 2H), 7.32 (d. J=5.4 Hz, 1H), 6.76 (m, 3H), 5.96 (s, 2H), 5.24 (s, 1H), 3.55 (q, J=6.5 Hz, 2H), 2.85 (t, J=6.3 Hz, 2H), 2.35 (s, 3H), HRMS (m/z): [M+H]$^+$ calculated for C$_{21}$H$_{19}$NO$_4$, 350.1387. found, 350.1385.

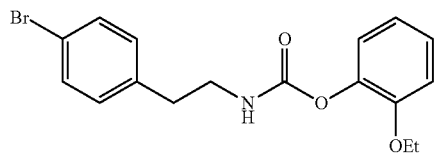 [SMILES: CCOc1ccccc1OC(=O)NCCc1ccc(Br)cc1]

JW418: 2-ethoxyphenyl 4-bromophenethylcarbamate $^1$H NMR 300 MHz (CDCl$_3$) δ 7.47 (d, J=7.9 Hz, 2H), 7.17 (m, 3H), 7.09 (d, J=7.8 Hz, 1H), 6.95 (dd, J=8.0, 12.1 Hz, 2H), 5.12 (s, 1H), 4.09 (q, J=7.0 Hz, 2H), 3.52 (q, J=6.6 Hz, 2H), 2.88 (t. J=6.9 Hz, 2H), 1.42 (t, J=7.0 Hz, 3H), HRMS (m/z): [M+H]$^+$ calculated for C$_{17}$H$_{18}$BrNO$_3$, 364.0543. found, 364.0538.

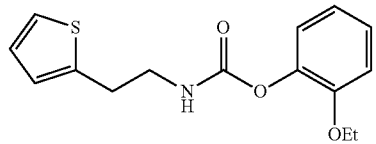 [SMILES: CCOc1ccccc1OC(=O)NCCc1cccs1]

JW419: 2-ethoxyphenyl(2-(thiophen-2-yl)ethyl)carbamate $^1$H NMR 300 MHz (CDCl$_3$) δ 7.14 (m, 3H), 6.94 (m, 4H), 5.23 (s, 1H), 4.07 (q, J=7.1 Hz, 2H), 3.56 (dd, J=6.1, 12.5 Hz, 2H), 3.12 (t, J=6.6 Hz, 2H), 1.40 (t, J=7.0 Hz, 3H), HRMS (m/z): [M+H]$^+$ calculated for C$_{15}$H$_{17}$NO$_3$S, 292.1002. found, 292.1008.

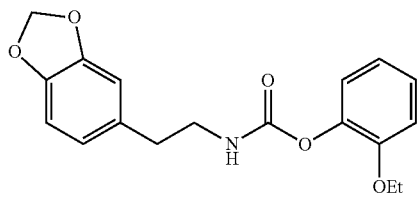 [SMILES: CCOc1ccccc1OC(=O)NCCc1ccc2c(c1)OCO2]

JW420: 2-ethoxyphenyl (2-(benzo[d][1,3]dioxol-5-yl)ethyl)carbamate $^1$H NMR 300 MHz (CDCl$_3$) δ 7.15 (m, 2H), 6.97 (m, 2H), 6.76 (m, 3H), 5.13 (s, 1H), 4.10 (q, J=7.0 Hz, 2H), 3.51 (q, J=6.6 Hz, 2H), 2.84 (t, J=6.8 Hz, 2H), 1.43 (t, J=6.9 Hz, 3H), HRMS (m/z): [M+H]$^+$ calculated for C$_{18}$H$_{19}$NO$_5$, 330.1336. found, 330.1336.

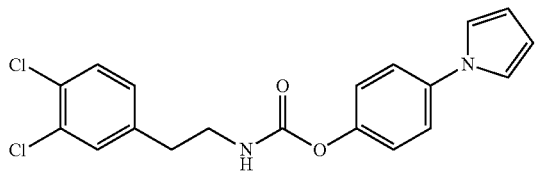 [SMILES: O=C(NCCc1ccc(Cl)c(Cl)c1)Oc1ccc(-n2cccc2)cc1]

JW421: 4-(1H-pyrrol-1-yl)phenyl 3,4-dichlorophenethylcarbamate $^1$H NMR 300 MHz (CDCl$_3$) δ 7.40 (m, 3H), 7.19 (d, J=8.5 Hz, 2H), 7.12 (dd, J=2.8, 6.4 Hz, 1H), 7.07 (m, 2H), 6.91 (d, J=7.0 Hz, 1H), 6.37 (t, J=0.8 Hz, 2H), 5.10 (s, 1H), 3.56 (q, J=6.2 Hz, 2H), 2.90 (t, J=6.3 Hz, 2H), HRMS (m/z): [M+H]$^+$ calculated for C$_{19}$H$_{16}$Cl$_2$N$_2$O$_2$, 375.0662. found, 375.0676.

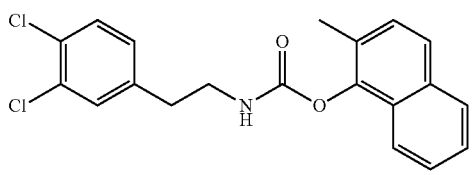 [SMILES: Cc1ccc2ccccc2c1OC(=O)NCCc1ccc(Cl)c(Cl)c1]

JW422: 2-methylnaphthalen-1-yl 3,4-dichlorophenethylcarbamate $^1$H NMR 300 MHz (CDCl$_3$) δ 7.78 (d, J=8.0 Hz, 2H), 7.66 (d, J=7.9 Hz, 1H), 7.42 (m, 5H), 7.11 (d, J=8.1 Hz, 1H), 5.25 (s, 1H), 3.59 (q, J=6.6 Hz, 2H), 2.91 (t, J=6.9 Hz, 2H), 2.34 (s, 3H), HRMS (m/z): [M+H]$^+$ calculated for C$_{20}$H$_{17}$Cl$_2$NO$_2$, 374.0709. found, 374.0713.

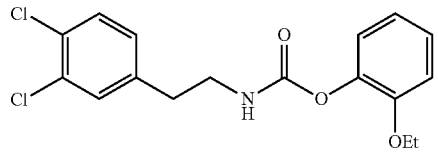 [SMILES: CCOc1ccccc1OC(=O)NCCc1ccc(Cl)c(Cl)c1]

JW423: 2-ethoxyphenyl 3,4-dichlorophenethylcarbamate $^1$H NMR 300 MHz (CDCl$_3$) δ 7.38 (m, 2H), 7.11 (m, 3H), 6.93 (m, 2H), 5.12 (s, 1H), 4.07 (q, J=6.9 Hz, 2H), 3.50 (q, J=7.5 Hz, 2H), 2.86 (1. J=6.9 Hz, 2H), 1.39 (t, J=7.2 Hz, 3H), HRMS (m/z): [M+H]$^+$ calculated for C$_{17}$H$_{17}$Cl$_2$NO$_3$, 354.0658. found, 354.0660.

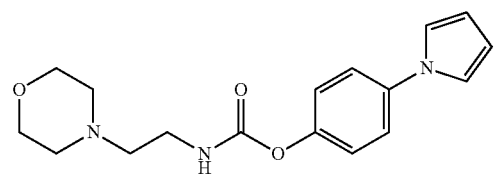 [SMILES: O=C(NCCN1CCOCC1)Oc1ccc(-n2cccc2)cc1]

JW425: 4-(1H-pyrrol-1-yl)phenyl (2-morpholinoethyl)carbamate $^1$H NMR 300 MHz (CDCl$_3$) δ 7.37 (d, J=8.7 Hz, 2H), 7.20 (d, J=9.0 Hz, 2H), 7.04 (m, 2H), 6.34 (m, 2H), 5.59 (s, 1H), 3.74 (m, 4H), 3.40 (q, J=5.4 Hz, 2H), 2.54 (m, 6H), HRMS (m/z): [M+H]$^+$ calculated for C$_{17}$H$_{21}$N$_3$O$_3$, 316.1656. found, 316.1657.

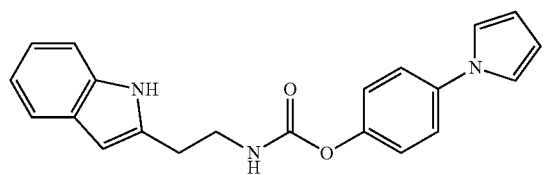 [SMILES: O=C(NCCc1cc2ccccc2[nH]1)Oc1ccc(-n2cccc2)cc1]

JW426: 4-(1H-pyrrol-1-yl)phenyl (2-(1H-indol-2-yl)ethyl)carbamate $^1$H NMR 300 MHz (CDCl$_3$) δ 8.08 (s, 1H), 7.69 (d, J=8.4 Hz, 1H), 7.41 (m, 4H), 7.20 (m, 4H), 7.06 (t, J=2.1 Hz, 2H), 6.37 (t, J=2.1 Hz, 2H), 5.14 (s, 1H), 3.67 (q, J=6.3 Hz, 2H), 3.11 (t, J=6.9 Hz, 2H), HRMS (m/z): [M+H]$^+$ calculated for C$_{21}$H$_{19}$N$_3$O$_2$, 346.155. found, 346.1554.

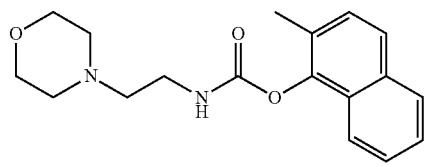 [SMILES: Cc1ccc2ccccc2c1OC(=O)NCCN1CCOCC1]

JW427: 2-methylnaphthalen-1-yl (2-morpholinoethyl)carbamate $^1$H NMR 300 MHz (CDCl$_3$) δ 7.85 (m, 2H), 7.66 (m, 1H), 7.47 (m, 2H), 7.36 (m, 1H), 5.72 (s, 1H), 3.75 (m, 4H), 3.44 (q, J=6.0 Hz, 2H), 2.56 (m, 6H), 2.40 (s, 3H), HRMS (m/z): [M+H]$^+$ calculated for C$_{18}$H$_{22}$N$_2$O$_3$, 315.1703. found, 315.1709.

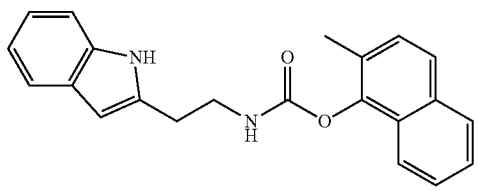 [SMILES: Cc1ccc2ccccc2c1OC(=O)NCCc1cc2ccccc2[nH]1]

JW428: 2-methylnaphthalen-1-yl (2-(1H-indol-2-yl)ethyl)carbamate $^1$H NMR 300 MHz (CDCl$_3$) δ 8.11 (s, 1H), 7.80 (m, 2H), 7.67 (m, 2H), 7.45 (m, 4H), 7.32 (m, 2H), 7.18 (m, 1H), 5.33 (s, 1H), 3.70 (q, J=6.6 Hz, 2H), 3.12 (t, J=6.6 Hz, 2H), 2.35 (s, 3H), HRMS (m/z): [M+H]$^+$ calculated for C$_{22}$H$_{20}$N$_2$O$_2$, 345.1597. found, 345.1597.

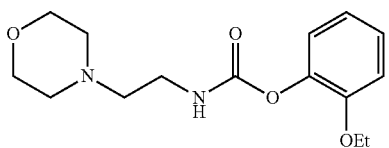 [SMILES: CCOc1ccccc1OC(=O)NCCN1CCOCC1]

JW429: 2-ethoxyphenyl (2-morpholinoethyl)carbamate $^1$H NMR 300 MHz (CDCl$_3$) δ 7.14 (m, 2H), 6.94 (m, 2H), 5.62 (s, 1H), 4.08 (q, J=6.9 Hz, 2H), 3.73 (m, 4H), 3.39 (q, J=5.7 Hz, 2H), 2.53 (m, 6H), 1.40 (t, J=6.3 Hz, 3H), HRMS (m/z): [M+H]$^+$ calculated for C$_{15}$H$_{22}$N$_2$O$_4$, 295.1652. found, 295.1655.

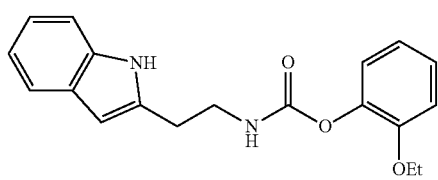 [SMILES: CCOc1ccccc1OC(=O)NCCc1cc2ccccc2[nH]1]

JW430: 2-ethoxyphenyl (2-(1H-indol-2-yl)ethyl)carbamate $^1$H NMR 300 MHz (CDCl$_3$) δ 8.02 (s, 1H), 7.60 (m, 2H), 7.39 (m, 3H), 7.29 (m, 1H), 7.13 (m, 2H), 6.97 (m, 1H), 5.37 (s, 1H), 4.10 (q, J=6.9 Hz, 2H), 3.48 (q, J=6.3 Hz, 2H), 2.94 (t, J=6.6 Hz, 2H), 1.42 (t, J=7.2 Hz, 3H), HRMS (m/z): [M+H]$^+$ calculated for C$_{19}$H$_{20}$N$_2$O$_3$, 325.1547. found, 325.1547.

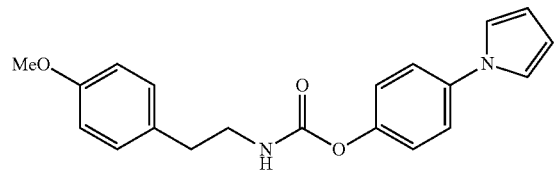 [SMILES: COc1ccc(CCNC(=O)Oc2ccc(-n3cccc3)cc2)cc1]

JW431: 4-(1H-pyrrol-1-yl)phenyl 4-methoxyphenethylcarbamate $^1$H NMR 300 MHz (CDCl$_3$) δ 7.39 (d, J=8.7 Hz, 2H), 7.19 (m, 4H), 7.07 (t, J=2.1 Hz, 2H), 6.92 (d, J=8.4 Hz, 2H), 6.37 (t, J=2.1 Hz, 2H), 5.06 (s, 1H), 3.84 (s, 3H), 3.55 (q, J=6.6 Hz, 2H), 2.88 (t, J=6.9 Hz, 2H), HRMS (m/z): [M+H]$^+$ calculated for C$_{20}$H$_{20}$N$_2$O$_3$, 337.1547. found, 337.1551.

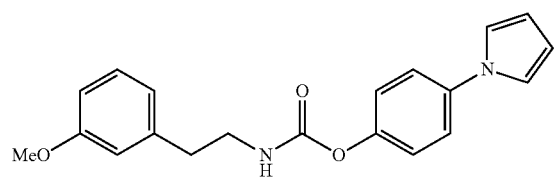 [SMILES: COc1cccc(CCNC(=O)Oc2ccc(-n3cccc3)cc2)c1]

JW432: 4-(1H-pyrrol-1-yl)phenyl 3-methoxyphenethylcarbamate $^1$H NMR 300 MHz (CDCl$_3$) δ 7.39 (d, J=8.7 Hz, 2H), 7.29 (m, 1H), 7.20 (d, J=9 Hz, 2H), 7.07 (t, J=2.1 Hz, 2H), 6.85 (m, 3H), 6.37 (t, J=2.1 Hz, 2H), 5.08 (s, 1H), 3.85 (s, 3H), 3.59 (q, J=6.6 Hz, 2H), 2.91 (t, J=6.9 Hz, 2H), HRMS (m/z): [M+H]$^+$ calculated for C$_{20}$H$_{20}$N$_2$O$_3$, 337.1547. found, 337.1550.

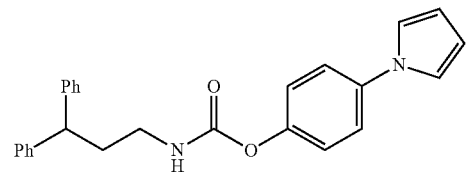 [SMILES: O=C(NCCC(c1ccccc1)c1ccccc1)Oc1ccc(-n2cccc2)cc1]

JW433: 4-(1H-pyrrol-1-yl)phenyl (3,3-diphenylpropyl)carbamate $^1$H NMR 300 MHz (CDCl$_3$) δ 7.33 (m, 13H), 7.22 (m, 2H), 7.07 (t, J=2.1 Hz, 1H), 6.37 (t, J=2.1 Hz, 2H), 5.02 (s, 1H), 4.05 (t, J=7.5 Hz, 1H), 3.29 (q, J=6.6 Hz, 2H), 2.41 (t, J=7.2 Hz, 2H), HRMS (m/z): [M+H]$^+$ calculated for C$_{26}$H$_{24}$N$_2$O$_2$, 397.191. found, 397.1912.

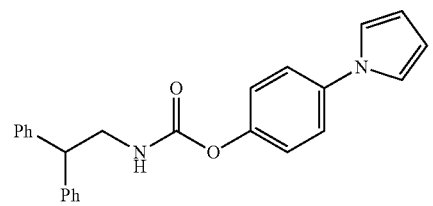 [SMILES: O=C(NCC(c1ccccc1)c1ccccc1)Oc1ccc(-n2cccc2)cc1]

JW434: 4-(1H-pyrrol-1-yl)phenyl (2,2-diphenylethyl)carbamate $^1$H NMR 300 MHz (CDCl$_3$) δ 7.34 (m, 12H), 7.16 (d, J=8.7 Hz, 2H), 7.06 (m, 2H), 6.36 (t, J=2.1 Hz, 2H), 5.04 (s, 1H), 4.31 (t, J=7.8 Hz, 1H), 3.96 (m, 2H), HRMS (m/z): [M+H]$^+$ calculated for C$_{25}$H$_{22}$N$_2$O$_2$, 383.1754. found, 383.1758.

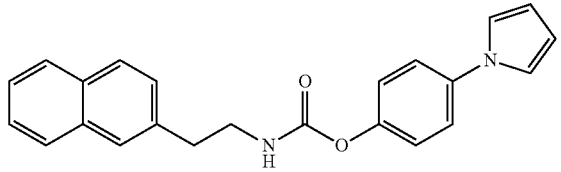 [SMILES: O=C(NCCc1ccc2ccccc2c1)Oc1ccc(-n2cccc2)cc1]

JW435: 4-(1H-pyrrol-1-yl)phenyl (2-(naphthalen-2-yl)ethyl)carbamate $^1$H NMR 300 MHz (CDCl$_3$) δ 7.87 (m, 3H), 7.73 (s, 1H), 7.52 (m, 2H), 7.40 (m, 3H), 7.18 (d, J=8.7 Hz, 2H), 7.04 (m, 2H), 6.36 (m, 2H), 5.08 (s, 1H), 3.68 (q, J=6.6 Hz, 2H), 3.11 (t, J=6.6 Hz, 2H), HRMS (m/z): [M+H]$^+$ calculated for C$_{23}$H$_{20}$N$_2$O$_2$, 357.1597. found, 357.1610.

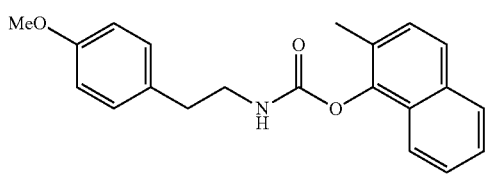

JW436: 2-methylnaphthalen-1-yl 4-methoxyphenethylcarbamate $^1$H NMR 300 MHz (CDCl$_3$) δ 7.79 (t, J=9.3 Hz, 2H), 7.65 (d, J=8.4 Hz, 1H), 7.45 (m, 2H), 7.27 (d, J=8.7 Hz, 1H), 7.19 (d, J=8.7 Hz, 2H), 6.90 (d, J=8.7 Hz, 2H), 5.22 (s, 1H), 3.82 (s, 3H), 3.58 (q, J=6.6 Hz, 2H), 2.89 (t, J=6.6 Hz, 2H), 2.35 (s, 3H), HRMS (m/z): [M+H]$^+$ calculated for C$_{21}$H$_{21}$NO$_3$, 336.1594. found, 336.1596.

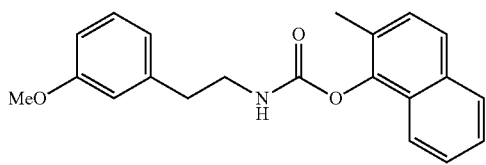 [SMILES: COc1cccc(CCNC(=O)Oc2c(C)ccc3ccccc23)c1]

JW437: 2-methylnaphthalen-1-yl 3-methoxyphenethylcarbamate $^1$H NMR 300 MHz (CDCl$_3$) δ 7.83 (t, J=7.4 Hz, 2H), 7.68 (d, J=8.4 Hz, 1H), 7.49 (m, 2H), 7.32 (m, 2H), 6.88 (m, 3H), 5.29 (s, 1H), 3.86 (s, 3H), 3.65 (q, J=6.6 Hz, 2H), 2.96 (t, J=6.8 Hz, 2H), 2.39 (s, 3H), HRMS (m/z): [M+H]$^+$ calculated for C$_{21}$H$_{21}$NO$_3$, 336.1594. found, 336.1598.

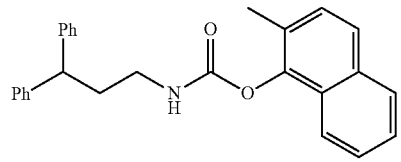

JW438: 2-methylnaphthalen-1-yl (3,3-diphenylpropyl)carbamate $^1$H NMR 300 MHz (CDCl$_3$) δ 7.82 (m, 2H), 7.64 (m, 1H), 7.46 (m, 3H), 7.30 (m, 10H), 5.22 (s, 1H), 4.06 (t, J=7.9 Hz, 1H), 3.32 (q, J=7.5 Hz, 2H), 2.42 (t, J=6 Hz, 2H), 2.37 (s, 3H), HRMS (m/z): [M+H]$^+$ calculated for C$_{27}$H$_{25}$NO$_2$, 396.1958. found, 396.1960.

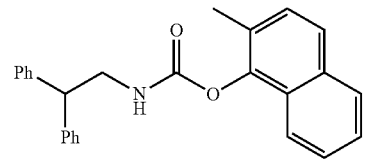 [SMILES: Cc1ccc2ccccc2c1OC(=O)NCC(c1ccccc1)c1ccccc1]

JW439: 2-methylnaphthalen-1-yl (2,2-diphenylethyl)carbamate $^1$H NMR 300 MHz (CDCl$_3$) δ 7.81 (m, 2H), 7.64 (m, 3H), 7.36 (m, 11H), 5.25 (s, 1H), 4.35 (t, J=8.1 Hz, 1H), 3.99 (m, 2H), 2.29 (s, 3H), HRMS (m/z): [M+H]$^+$ calculated for C$_{26}$H$_{23}$NO$_2$, 382.1801. found, 382.1805.

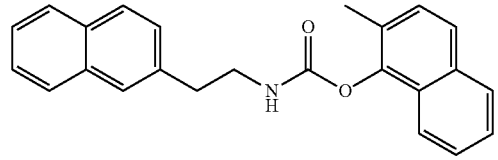 [SMILES: Cc1ccc2ccccc2c1OC(=O)NCCc1ccc2ccccc2c1]

JW440: 2-methylnaphthalen-1-yl (2-(naphthalen-2-yl)ethyl)carbamate $^1$H NMR 300 MHz (CDCl$_3$) δ 7.83 (m, 6H), 7.66 (d, J=6.0 Hz, 1H), 7.52 (m, 2H), 7.43 (m, 3H), 7.33 (d, J=9.0 Hz, 1H), 5.30 (s, 1H), 3.73 (q, J=6.1 Hz, 2H), 3.14 (t, J=6.0 Hz, 2H), 2.36 (s, 3H), HRMS (m/z): [M+H]$^+$ calculated for C$_{24}$H$_{21}$NO$_2$, 356.1645. found, 356.1648.

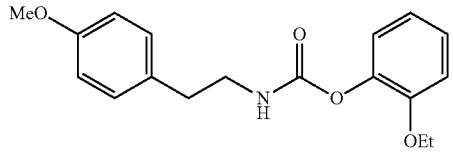

JW441: 2-ethoxyphenyl 4-methoxyphenethylcarbamate $^1$H NMR 300 MHz (CDCl$_3$) δ 7.15 (m, 3H), 7.08 (d, J=7.5 Hz, 1H), 6.91 (m, 4H), 5.10 (s, 1H), 4.07 (q, J=7.0 Hz, 2H), 3.80 (s, 3H), 3.51 (q, J=9.0 Hz, 2H), 2.84 (t, J=6.9 Hz, 2H), 1.40 (t, J=6.9 Hz, 3H), HRMS (m/z): [M+H]$^+$ calculated for C$_{18}$H$_{21}$NO$_4$, 316.1543. found, 316.1545.

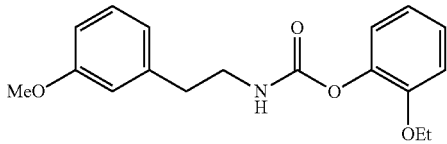 [SMILES: CCOc1ccccc1OC(=O)NCCc1cccc(OC)c1]

JW442: 2-ethoxyphenyl 3-methoxyphenethylcarbamate $^1$H NMR 300 MHz (CDCl$_3$) δ 7.26 (m, 2H), 7.13 (m, 2H), 6.94 (m, 2H), 6.82 (m, 2H), 5.13 (s, 1H), 4.08 (q, J=7.0 Hz, 2H), 3.82 (s, 3H), 3.54 (q, J=6.7 Hz, 2H), 2.88 (t, J=7.0 Hz, 2H), 1.41 (t, J=6.9 Hz, 3H), HRMS (m/z): [M+H]$^+$ calculated for C$_{18}$H$_{21}$NO$_4$, 316.1543. found, 316.1545.

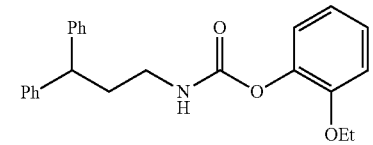 [SMILES: CCOc1ccccc1OC(=O)NCCC(c1ccccc1)c1ccccc1]

JW443: 2-ethoxyphenyl (3,3-diphenylpropyl)carbamate $^1$H NMR 300 MHz (CDCl$_3$) δ 7.29 (m, 9H), 7.15 (m, 3H), 6.93 (m, 2H), 5.08 (s, 1H), 4.06 (m, 3H), 3.25 (dd, J=6.8, 13.6 Hz, 2H), 2.38 (t, J=7.6 Hz, 2H), 1.37 (t, J=6.9 Hz, 3H), HRMS (m/z): [M+H]$^+$ calculated for C$_{24}$H$_{25}$NO$_3$, 376.1907. found, 376.1910.

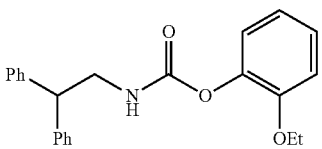

JW444: 2-ethoxyphenyl (2,2-diphenylethyl)carbamate $^1$H NMR 300 MHz (CDCl$_3$) δ 7.32 (m, 10H), 7.18 (t, J=7.2 Hz, 1H), 7.08 (d. J=7.5 Hz, 1H), 6.95 (m, 2H), 5.10 (s, 1H), 4.31 (t, J=7.8 Hz, 1H), 4.08 (q, J=6.9 Hz, 2H), 3.95 (t, J=6.8 Hz, 2H), 1.42 (t. J=6.9 Hz, 3H). HRMS (m/z): [M+H]$^+$ calculated for C$_{23}$H$_{23}$NO$_3$, 362.1751. found, 362.1747.

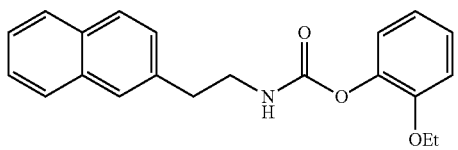 [SMILES: CCOc1ccccc1OC(=O)NCCc1ccc2ccccc2c1]

JW445: 2-ethoxyphenyl(2-(naphthalen-2-yl)ethyl)carbamate $^1$H NMR 300 MHz (CDCl$_3$) δ 7.86 (m, 3H), 7.74 (m, 1H), 7.53 (m, 3H), 7.16 (m, 2H), 6.96 (m, 2H), 5.34 (s, 1H), 4.10 (q, J=6.8 Hz, 2H), 3.66 (q, J=7.9 Hz, 2H), 3.10 (t, J=6.9 Hz, 2H), 1.43 (t, J=7.3 Hz, 3H), HRMS (m/z): [M+H]$^+$ calculated for C$_{21}$H$_{21}$NO$_3$, 336.1594. found, 336.1594.

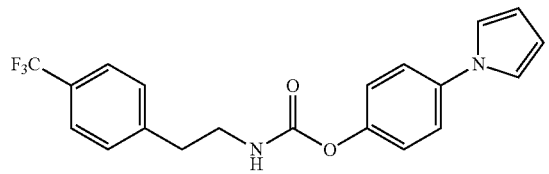 [SMILES: O=C(NCCc1ccc(C(F)(F)F)cc1)Oc1ccc(-n2cccc2)cc1]

JW446: 4-(1H-pyrrol-1-yl)phenyl 4-(trifluoromethyl)phenethylcarbamate $^1$H NMR 300 MHz (CDCl$_3$) δ 7.62 (d, J=7.9 Hz, 2H), 7.38 (m, 4H), 7.17 (m, 2H), 7.05 (t, J=2.2 Hz, 2H), 6.35 (m, 2H), 5.08 (s, 1H), 3.58 (q, J=6.7 Hz, 2H), 2.99 (t, J=7.0 Hz, 2H), HRMS (m/z): [M+H]$^+$ calculated for C$_{20}$H$_{17}$F$_3$N$_2$O$_2$, 375.1315. found, 375.1325.

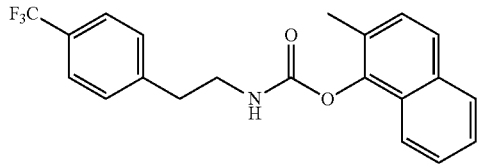 [SMILES: Cc1ccc2ccccc2c1OC(=O)NCCc1ccc(C(F)(F)F)cc1]

JW447: 2-methylnaphthalen-1-yl 4-(trifluoromethyl)phenethylcarbamate $^1$H NMR 300 MHz (CDCl$_3$) δ 7.80 (m, 2H), 7.66 (m, 3H), 7.45 (m, 4H), 7.35 (d, J=9 Hz, 1H), 5.29 (s, 1H), 3.66 (q, J=6.1 Hz, 2H), 3.04 (t, J=6.0 Hz, 2H), 2.34 (s, 3H), HRMS (m/z): [M+H]$^+$ calculated for C$_{21}$H$_{18}$F$_3$NO$_2$, 374.1362. found, 374.1363.

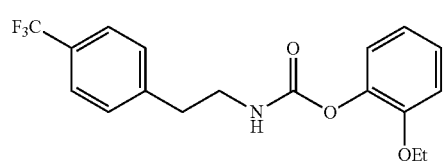 [SMILES: CCOc1ccccc1OC(=O)NCCc1ccc(C(F)(F)F)cc1]

JW448: 2-ethoxyphenyl 4-(trifluoromethyl)phenethylcarbamate $^1$H NMR 300 MHz (CDCl$_3$) δ 7.63 (d, J=8.2 Hz, 2H), 7.42 (m, 2H), 7.20 (m, 1H), 7.10 (m, 1H), 6.98 (m, 2H), 5.15 (s, 1H), 4.10 (q, J=7.0 Hz, 2H), 3.58 (q, J=7.1 Hz, 2H), 2.99 (t, J=6.6 Hz, 2H), 1.43 (t, J=7.0 Hz, 3H), HRMS (m/z): [M+H]$^+$ calculated for C$_{18}$H$_{18}$F$_3$NO$_3$, 354.1311. found, 354.1306.

85

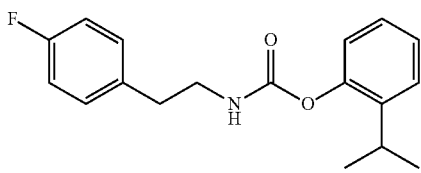 [SMILES: CC(C)c1ccccc1OC(=O)NCCc1ccc(F)cc1]

JW464: 2-isopropylphenyl 4-fluorophenethylcarbamate $^1$H NMR 300 MHz (CDCl$_3$) δ 7.32 (m, 1H), 7.21 (m, 4H), 7.05 (m, 3H), 5.06 (s, 1H), 3.55 (q, J=6.0 Hz, 2H), 3.08 (m, 1H), 2.90 (t, J=6.1 Hz, 2H), 1.22 (d, J=8.9 Hz, 6H), HRMS (m/z): [M+H]$^+$ calculated for C$_{18}$H$_{20}$FNO$_2$, 302.1551. found, 302.1549.

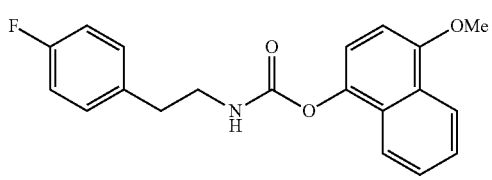 [SMILES: COc1ccc(OC(=O)NCCc2ccc(F)cc2)c2ccccc12]

JW465: 4-methoxynaphthalen-1-yl 4-fluorophenethylcarbamate $^1$H NMR 300 MHz (CDCl$_3$) δ 8.29 (m, 1H), 7.81 (m, 1H), 7.54 (m, 3H), 7.29 (m, 1H), 7.18 (m, 1H), 7.08 (m, 2H), 6.79 (m, 1H), 5.22 (s, 1H), 4.03 (s, 3H), 3.59 (q, J=6.2 Hz, 2H), 2.94 (t, J=6.1 Hz, 2H), HRMS (m/z): [M+H]$^+$ calculated for C$_{20}$H$_{18}$FNO$_3$, 340.1343. found, 340.1346.

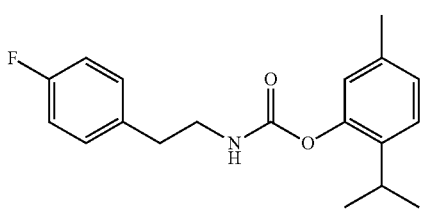 [SMILES: Cc1ccc(C(C)C)c(OC(=O)NCCc2ccc(F)cc2)c1]

JW466: 2-isopropyl-5-methylphenyl 4-fluorophenethylcarbamate $^1$H NMR 300 MHz (CDCl$_3$) δ 7.22 (m, 3H), 7.05 (m, 3H), 6.87 (s, 1H), 5.06 (s, 1H), 3.51 (q, J=6.0 Hz, 2H), 3.04 (m, 1H), 2.91 (t, J=6.9 Hz, 2H), 2.34 (s, 3H), 1.27 (d, J=7.3 Hz, 6H), HRMS (m/z): [M+H]$^+$ calculated for C$_{19}$H$_{22}$FNO$_2$, 316.1707. found, 316.1712.

86

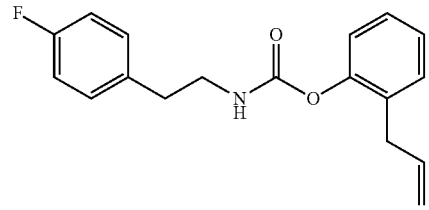 [SMILES: C=CCc1ccccc1OC(=O)NCCc1ccc(F)cc1]

JW468: 2-allylphenyl 4-fluorophenethylcarbamate $^1$H NMR 300 MHz (CDCl$_3$) δ 7.21 (m, 5H), 7.04 (m, 3H), 5.93 (m, 1H), 5.06 (m, 3H), 3.55 (q, J=6.6 Hz, 2H), 3.32 (d, J=6.5 Hz, 2H), 2.89 (t, J=6.9 Hz, 2H), HRMS (m/z): [M+H]$^+$ calculated for C$_{18}$H$_{18}$FNO$_2$, 300.1309. found, 300.1412.

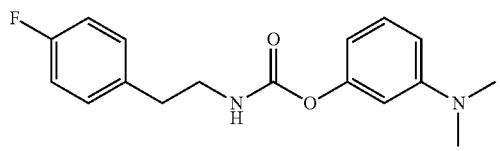 [SMILES: CN(C)c1cccc(OC(=O)NCCc2ccc(F)cc2)c1]

JW469: 3-(dimethylamino)phenyl 4-fluorophenethylcarbamate $^1$H NMR 300 MHz (CDCl$_3$) δ 7.18 (m, 3H), 7.02 (t, J=8.6 Hz, 2H), 6.56 (d, J=8.3 Hz, 1H), 6.44 (m, 2H), 4.98 (s, 1H), 3.51 (q, J=6.8 Hz, 2H), 2.93 (s, 6H), 2.86 (t, J=6.7 Hz, 2H), HRMS (m/z): [M+H]$^+$ calculated for C$_{17}$H$_{19}$FN$_2$O$_2$, 303.1503. found, 303.1506.

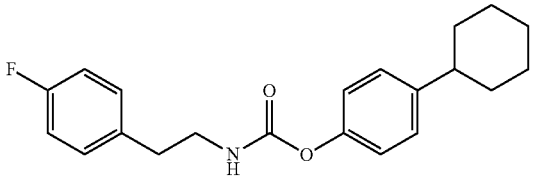 [SMILES: O=C(NCCc1ccc(F)cc1)Oc1ccc(C2CCCCC2)cc1]

JW472: 4-cyclohexylphenyl 4-fluorophenethylcarbamate $^1$H NMR 300 MHz (CDCl$_3$) δ 7.20 (m, 4H), 7.03 (m, 4H), 5.00 (s, 1H), 3.51 (q, J=6.7 Hz, 2H), 2.87 (t, J=6.9 Hz, 2H), 2.49 (m, 1H), 1.79 (m, 4H), 1.35 (m, 6H), HRMS (m/z): [M+H]$^+$ calculated for C$_{21}$H$_{24}$FNO$_2$, 342.1864. found, 342.1870.

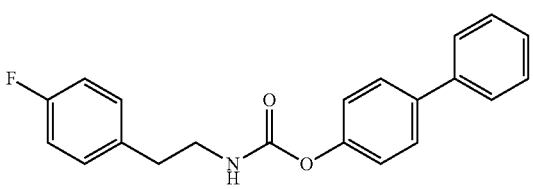 [SMILES: O=C(NCCc1ccc(F)cc1)Oc1ccc(-c2ccccc2)cc1]

JW473: [1,1'-biphenyl]-4-yl 4-fluorophenethylcarbamate $^1$H NMR 300 MHz (CDCl$_3$) δ 7.57 (m, 4H), 7.44 (t, J=7.8 Hz, 2H), 7.35 (t, J=7.2 Hz, 1H), 7.21 (m, 4H), 7.04 (m, 2H), 5.06 (s, 1H), 3.54 (q, J=6.7 Hz, 2H), 2.90 (t, J=6.9 Hz, 2H), HRMS (m/z): [M+H]$^+$ calculated for C$_{21}$H$_{18}$FNO$_2$, 336.1394. found, 336.1395.

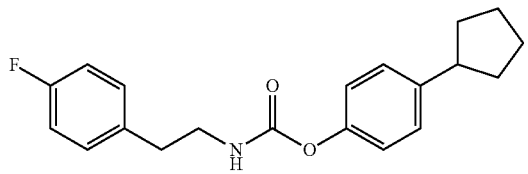 [SMILES: O=C(NCCc1ccc(F)cc1)Oc1ccc(C2CCCC2)cc1]

JW474: 4-cyclopentylphenyl 4-fluorophenethylcarbamate $^1$H NMR 300 MHz (CDCl$_3$) δ 7.19 (m, 4H), 7.02 (m, 4H), 4.99 (s, 1H), 3.50 (q, J=6.8 Hz, 2H), 2.97 (m, 1H), 2.86 (t, J=6.6 Hz, 2H), 2.05 (m, 2H), 1.72 (m, 4H), 1.59 (m, 2H), HRMS (m/z): [M+H]$^+$ calculated for C$_{20}$H$_{22}$FNO$_2$, 328.1707. found, 328.1699.

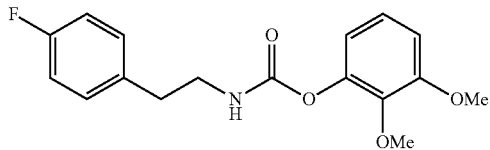 [SMILES: COc1cccc(OC(=O)NCCc2ccc(F)cc2)c1OC]

JW477: 2,3-dimethoxyphenyl 4-fluorophenethylcarbamate $^1$H NMR 300 MHz (CDCl$_3$) δ 7.22 (m, 2H), 7.03 (m, 3H), 6.82 (m, 1H), 6.72 (m, 1H), 5.13 (s, 1H), 3.88 (s, 3H), 3.85 (s, 3H), 3.53 (q, J=6.7 Hz, 2H), 2.89 (t, J=6.9 Hz, 2H), HRMS (m/z): [M+H]$^+$ calculated for C$_{17}$H$_{18}$FNO$_4$, 320.1293. found, 320.1300.

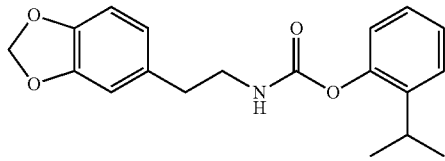 [SMILES: CC(C)c1ccccc1OC(=O)NCCc1ccc2c(c1)OCO2]

JW481: 2-isopropylphenyl (2-(benzo[d][1,3]dioxol-5-yl)ethyl)carbamate $^1$H NMR 300 MHz (CDCl$_3$) δ 7.29 (m, 1H), 7.19 (m, 2H), 7.05 (m, 1H), 6.74 (m, 3H), 5.96 (d, J=1.1 Hz, 2H), 5.05 (s, 1H), 3.51 (q, J=6.6 Hz, 2H), 3.09 (m, 1H), 2.82 (t, J=6.8 Hz, 2H), 1.23 (d, J=8.7 Hz, 6H), HRMS (m/z): [M+H]$^+$ calculated for C$_{19}$H$_{21}$NO$_4$, 328.1543. found, 328.1542.

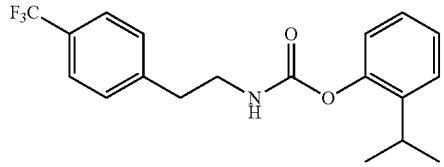 [SMILES: CC(C)c1ccccc1OC(=O)NCCc1ccc(C(F)(F)F)cc1]

JW482: 2-isopropylphenyl 4-(trifluoromethyl)phenethylcarbamate $^1$H NMR 300 MHz (CDCl$_3$) δ 7.61 (d, J=8.0 Hz, 2H), 7.38 (d, J=8.0 Hz, 2H), 7.28 (m, 1H), 7.20 (m, 2H), 7.03 (m, 1H), 5.07 (s, 1H), 3.59 (q, J=6.8 Hz, 2H), 3.03 (m, 3H), 1.21 (d, J=6.9 Hz, 6H), HRMS (m/z): [M+H]$^+$ calculated for C$_{19}$H$_{20}$F$_3$NO$_2$, 352.1519. found, 352.1519.

Biology

Preparation of Mouse Tissue Proteomes

Tissues were Dounce-homogenized in PBS, pH 7.4, followed by a low-speed spin (1,400 g, 5 min) to remove debris. The supernatant was then subjected to centrifugation (100,000×g, 45 min) to provide the cytosolic fraction in the supernatant and the unsoluble fraction as a pellet. The pellet was washed and resuspended in PBS buffer by sonication. Total protein concentration in each fraction was determined using a protein assay kit (Bio-Rad). Samples were stored at −80° C. until use.

Inhibitor Treatments of Cells

Inhibitors were dissolved in DMSO and diluted into media or buffer prior to cell or proteome treatment, respectively. For in vitro treatment, final DMSO concentration was 4%. For in situ treatments of cells for ABPP, lipid measurements, migration, cell-survival, and invasion assays, 2×10$^6$ cells were seeded in 6 cm dishes (~100% confluency) 24 h prior to inhibitor pre-treatment (in DMSO at 0.1% final concentration) in serum-free media (3 mL) for the designated time before harvesting cells for ABPP or lipid measurements or before the initiation of migration, cell-survival, and invasion assays.

2-Acetyl MAGE Hydrolytic Activity Assays

Cells were pretreated with KIAA1363 inhibitors in situ (for 4 hr in serum-free F-12K media before harvesting cells by scraping) or in vitro (for 30 min at 37° C. in PBS) before addition of 2-acetyl MAGE (100 µM) to cell lysates at room temperature for 30 min in a volume of 200 µL. Reactions were quenched with 600 µL 2:1 chloroform:methanol and 10 nmol of C12:0 MAGE internal standard was added. The organic layer was extracted and 30 µL injected into an Agilent 1100-MSD LC-MS. LC-MS settings were as previously described (Chiang et al., 2006). Product levels (C16:0 MAGE) were quantified in relation to the internal standard. Specific activity was determined during the linear phase of enzymatic reactions (i.e., less than 20% substrate utilized).

AChE Activity Assays

AChE activity was measured using a method similar to that described previously (Ellman et al., 1961). Briefly, 50 µL of 10 mM acetylthiocholine was added to 200 µL of PBS containing 2 mM DTNB and 20 µg of cell lysate or mouse brain membrane proteome. Absorbance was measured at 412 nm over 5 min, and the rate of product accumulation was calculated from the slope of the absorbance over time. For assays involving preincubation with inhibitors, the reactions were prepared without acetylthiocholine and JW480 was incubated at the indicated concentration for 30 min at 37° C.

Acetylthiocholine was then added and the assay was carried out exactly as described above.

Competitive ABPP Experiments

For ABPP experiments, cell lysate and tissue proteomes were treated with 1 μM FP-rhodamine for 30 min at room temperature (50 μL total reaction volume) as described previously (Nomura et al., 2010). Reactions were quenched with one volume of standard 4×SDS/PAGE loading buffer (reducing), separated by SDS/PAGE (10% acrylamide), and visualized in-gel with a Hitachi FMBio IIe flatbed fluorescence scanner (MiraiBio). Inhibitors were preincubated prior (30 min or 4 h at 37° C. in vitro or in situ, respectively) to the addition of FP-rhodamine.

Competitive ABPP-MudPIT Analysis of Serine Hydrolase Activities in Proteomes

Competitive ABPP-MudPIT experiments were performed as previously described (Nomura et al., 2010). Briefly, 1 mg of proteome was labeled with 5 μM FP-biotin, followed by solubilization with 1% Triton X-100, denaturation by SDS and heating, avidin precipitation of labeled proteins, and on-bead tryptic digest. Tryptic peptides were then loaded on to a biphasic (strong cation exchange/reverse phase) capillary column and analyzed by two-dimensional liquid chromatography (2D-LC) separation in combination with tandem mass spectrometry using an Agilent 1100 LC system coupled with a ThermoFisher LTQ linear ion trap mass spectrometer. Spectral counts are reported as the average of three samples with the standard error of the mean (SEM).

Generation of KIAA1363 Knockdown Cells

Stable knockdown of KIAA1363 in PC3 cells was achieved using a targeted short-hairpin oligonucleotide described previously (Chiang et al., 2006).

Cell Migration, Cell Survival, and Invasion Studies

Cell migration, cell survival, and invasion studies were performed as previously described (Nomura et al., 2010). Briefly, migration assays were performed in Transwell chambers (Corning) with 8 μm pore-sized membranes coated with 10 μg/mL collagen at 37° C. for LNCaP (24 h), PC3 (4 h) and DU145 cells (24 h), respectively. Cell survival assays were performed using the Cell Proliferation Reagent WST-1 (Roche) Invasion assays were conducted using the BD Matrigel Invasion Chambers per the manufacturer's protocol. Inhibitors were preincubated for the stated duration before seeding cells into migration, cell-survival, or invasion chambers. Prior to seeding the cells in these chambers, cells were serum-starved for 4 h. Inhibitors were also present during the migration, cell-survival, and invasion assays.

In Vivo Studies with JW480

JW480 was administered by oral gavage (in PEG300, 4 μL/g mouse) or intraperitoneally (in 18:1:1 v/v/v solution of saline:ethanol:emulphor, 10 μL/g). After the indicated amount of time, mice were anesthetized with isoflurane and killed by decapitation. Tissues were removed and then flash frozen in liquid $N_2$. Tissues were stored at −80° C. until use. Animal experiments were conducted in accordance with the guidelines of the institutional Animal Care and Use Committee of The Scripps Research Institute.

Tumor Xenograft Studies

Human cancer xenografts were established by transplanting cancer cell lines ectopically into the flank of C.B17 SCID mice (Taconic Farms). Briefly, cells were washed two times with PBS, trypsinized, and harvested in serum-containing medium. Next, the harvested cells were washed two times with serum-free medium and resuspended at a concentration of $2.0 \times 10^4$ cells/μL and 100 μL was injected. Growth of the tumors was measured every 3 days with calipers. For chronic JW480 treatment studies, mice were treated with JW480 or vehicle once daily (at approximately the same time everyday) by oral gavage in PEG300 (4 μL/g mouse). The treatments were initiated immediately after ectopic injection of cancer cells.

Lipid Measurements in Cancer Cells

Lipid measurements were performed in cancer cells as previously described (Chiang et al., 2006). Briefly, frozen cell pellets from cells harvested after 4 h serum starvation were extracted in 2:1:1 chloroform:methanol:Tris buffer pH 8.0 by dounce homogenization with 10 nmol of internal standard C12 MAGE. The organic layer was removed, dried under $N_2$, and resuspended in 120 μL of chloroform, and 30 μL was injected into an Agilent 1100-MSD LC-MS. MAGE levels were quantified by measuring the area under the peak and were normalized to the C12 MAGE internal standard.

Fluorescent Probe Carbamates

General Synthetic Methods

All chemicals were obtained from Aldrich, Acros, Fisher, Fluka or Invitrogen and were used without further purification, except where noted. Dry solvents (dichloromethane) and triethylamine were obtained by passage through activated alumina columns. All reactions were carried out under an inert nitrogen atmosphere using oven-baked glassware unless otherwise noted. Flash chromatography was performed using 230-400 mesh silica gel 60. $^1$H spectra were recorded on a Varian 400 MHz spectrometer. Chemical shifts are reported in values relative to tetramethylsilane, and coupling constants (J) are reported in Hz.

Synthesis of JW576

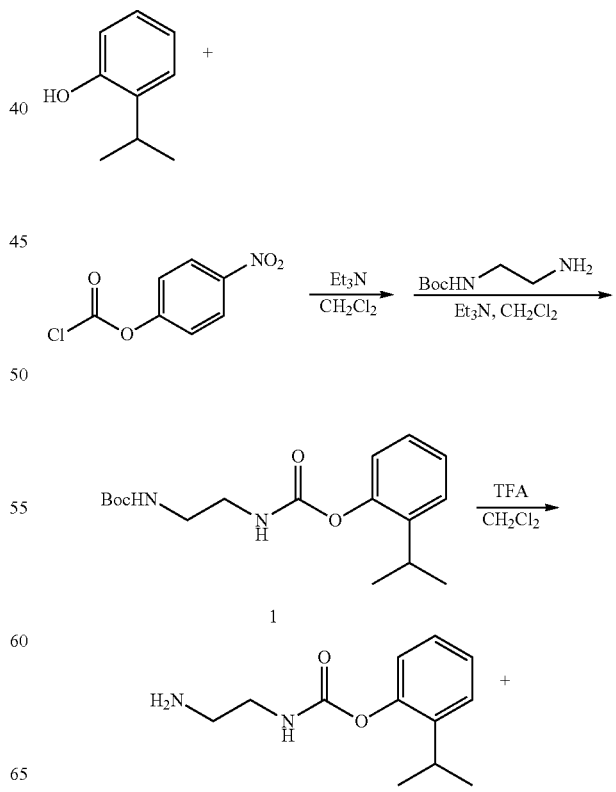

Scheme 1

-continued

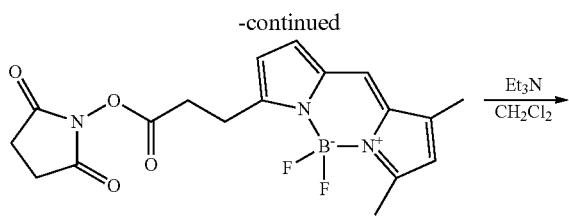

1H), 1.46 (s, 9H), 1.21 (d, J=4.0 Hz, 6H), HRMS (m/z): [M+H]$^+$ calculated for $C_{17}H_{26}N_2O_4$, 323.1965. found, 323.1976.

JW576: 5,5-difluoro-7-(3-((2-(((2-isopropylphenoxy)carbonyl)amino)ethyl)amino)-3-oxopropyl)-1,3-dimethyl-5H-dipyrrolo[1,2-c:2',1'-f][1,3,2]diazaborinin-4-ium-5-uide

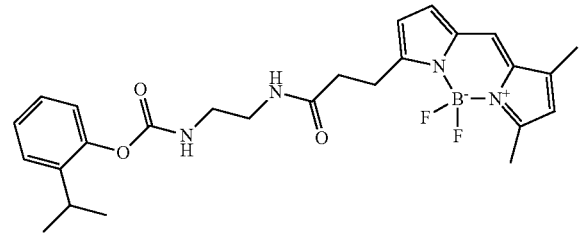

To a solution of tert-butyl (2-isopropylphenyl)ethane-1,2-diyldicarbamate (10 mg, 0.031 mmol) in dichloromethane (0.5 mL) was added TFA (11 mg, 0.093 mmol) at 0° C. After stirred at room temperature overnight, the reaction mixture was treated with 3.0 mL of saturated aqueous $NaHCO_3$ solution. The organic layer was separated and the aqueous layer was extracted with dichloromethane. The combined organic extracts were washed with brine, dried over $MgSO_4$, filtered and concentrated. The crude product was used without further purification. To a solution of carbonate intermediate in dichloromethane (0.5 mL) was added 7-(3-((2,5-dioxopyrrolidin-1-yl)oxy)-3-oxopropyl)-5,5-difluoro-1,3-dimethyl-5H-dipyrrolo[1,2-c:2',1'-f][1,3,2]diazaborinin-4-ium-5-uide (5.0 mg, 0.013 mmol) and $Et_3N$ (4.0 mg, 0.039 mmol) at 0° C. After stirred at room temperature for 5 hours, the reaction mixture was treated with 3.0 mL of saturated aqueous $NaHCO_3$ solution. The organic layer was separated and the aqueous layer was extracted with dichloromethane. The combined organic extracts were washed with brine, dried over $MgSO_4$, filtered and concentrated. The crude product was purified by preparative TLC using a 1:1 v/v Hexane:Ethyl acetate as solvent to afford title compound (5.2 mg, 81% yield) as a red solid.

$^1$H NMR 400 MHz (CDCl$_3$) δ 7.29 (m, 1H), 7.19 (m, 2H), 7.09 (s, 1H), 7.00 (m, 1H), 6.94 (d, J=4.0 Hz, 1H), 6.35 (d, J=4.0 Hz, 1H), 6.17 (s, 1H), 6.13 (s, 1H), 5.44 (s, 1H), 3.42 (m, 2H), 3.32 (m, 4H), 3.09 (m, 1H), 2.74 (t, J=8.0 Hz, 2H), 2.60 (s, 3H), 2.19 (s, 3H), 1.22 (d, J=8.0 Hz, 6H), HRMS (m/z): [M+H]$^+$ calculated for $C_{26}H_{31}BF_2N_4O_3$, 497.2533. found, 497.2553.

JW576

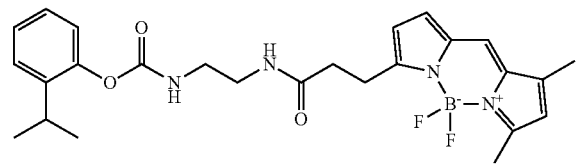

1: tert-butyl (2-isopropylphenyl)ethane-1,2-diyldicarbamate

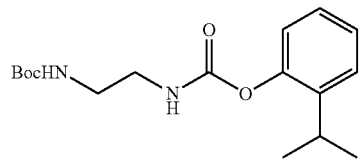 [SMILES: CC(C)c1ccccc1OC(=O)NCCNC(=O)OC(C)(C)C]

To a solution of 2-isopropylphenol (5.0 g, 36.713 mmol) in dichloromethane (183.0 mL) was added 4-nitrophenylchloroformate (8.1 g, 40.385 mmol) and $Et_3N$ (10.3 mL, 73.426 mmol) at 0° C. After stirring at 0° C. 2 hours, the reaction mixture treated with 30.0 mL of saturated aqueous $NaHCO_3$ solution. The organic layer was separated and the aqueous layer was extracted with dichloromethane. The combined organic extracts were washed with brine, dried over $MgSO_4$, filtered and concentrated. The crude product was used without further purification. To a solution of carbonate intermediate (100 mg, 0.331 mmol) in dichloromethane (3.3 mL) was added tert-butyl (2-aminoethyl)carbamate (58 mg, 0.365 mmol) and $Et_3N$ (0.14 mL, 0.995 mmol) at 0° C. After stirring at 0° C. 2 hours, the reaction mixture was treated with 10.0 mL of saturated aqueous $NaHCO_3$ solution. The organic layer was separated and the aqueous layer was extracted with dichloromethane. The combined organic extracts were washed with brine, dried over $MgSO_4$, filtered and concentrated. The crude product was purified by flash column chromatography using a 9:1 v/v hexane:ethyl acetate as solvent to afford title compound (95 mg, 88% yield) as a white solid.

$^1$H NMR 400 MHz (CDCl$_3$) δ 7.29 (m, 1H), 7.19 (m, 2H), 7.05 (m, 1H), 5.54 (s, 1H), 4.89 (s, 1H), 3.37 (m, 4H), 3.11 (m, tert-Butyl (2-((2-oxo-4-(trifluoromethyl)-2H-chromen-7-yl)oxy)ethyl)carbamate

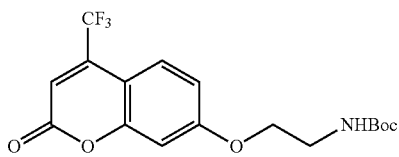 [SMILES: CC(C)(C)OC(=O)NCCOc1ccc2c(C(F)(F)F)cc(=O)oc2c1]

To a solution of 7-hydroxy-4-(trifluoromethyl)-2H-chromen-2-one (213 mg, 0.925 mmol) in DMF (1.5 mL) was added tert-butyl (2-bromoethyl)carbamate (416 mg, 1.851 mmol) and K$_2$CO$_3$ (384 mg, 2.776 mmol) at r.t. After stirred at 85° C. for 12 hours, the reaction mixture treated with 10.0 mL of saturated aqueous NaHCO$_3$ solution. The organic layer was separated and the aqueous layer was extracted with Ethyl acetate. The combined organic extracts were washed with brine, dried over MgSO$_4$, filtered and concentrated. The crude product was purified by flash column chromatography using a 9:1 v/v Hexane:Ethyl acetate as solvent to afford title compound (300 mg, 87% yield) as a white solid. $^1$H NMR 300 MHz (CDCl$_3$) δ 7.64 (d, J=6.0 Hz, 1H), 6.91 (m, 2H), 6.61 (s, 1H), 4.95 (s, 1H), 4.11 (m, 2H), 3.58 (m, 2H), 1.56 (s, 9H), HRMS (m/z): [M+H]$^+$ calculated for C$_{17}$H$_{18}$F$_3$NO$_5$. found, 374.1207.

2-isopropylphenyl (2-((2-oxo-4-(trifluoromethyl)-2H-chromen-7-yl)oxy)ethyl)carbamate

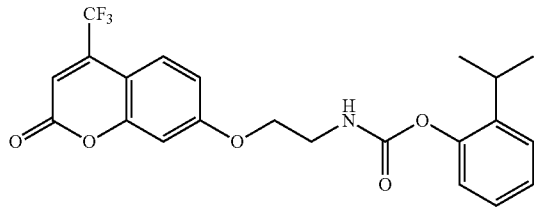 [SMILES: CC(C)c1ccccc1OC(=O)NCCOc1ccc2c(C(F)(F)F)cc(=O)oc2c1]

To a solution of tert-butyl (2-((2-oxo-4-(trifluoromethyl)-2H-chromen-7-yl)oxy)ethyl)carbamate (117 mg, 0.313 mmol) in dichloromethane (1.5 mL) was added TFA (107 mg, 0.940 mmol) at 0° C. After stirred at r.t. for 6 hours, the reaction mixture treated with 10.0 mL of saturated aqueous NaHCO$_3$ solution. The organic layer was separated and the aqueous layer was extracted with dichloromethane. The combined organic extracts were washed with brine, dried over MgSO$_4$, filtered and concentrated. The crude product was used without further purification. To a solution of amine intermediate (85 mg, 0.313 mmol) in dichloromethane (3.0 mL) was added 2-isopropylphenyl (4-nitrophenyl)carbonate (94 mg, 0.313 mmol) and Et$_3$N (0.14 mL, 0.939 mmol) at 0° C. After stirred at r.t for 4 hours, the reaction mixture treated with 10.0 mL of saturated aqueous NaHCO$_3$ solution. The organic layer was separated and the aqueous layer was extracted with dichloromethane. The combined organic extracts were washed with brine, dried over MgSO$_4$, filtered and concentrated. The crude product was purified by flash column chromatography using a 9:1 v/v Hexane:Ethyl acetate as solvent to afford title compound (110 mg, 81% yield) as a white solid.

$^1$H NMR 300 MHz (CDCl$_3$) δ 8.16 (d, J=9.0 Hz, 1H), 7.66 (d, J=9.0 Hz, 1H), 7.21 (m, 1H), 7.07 (m, 1H), 6.92 (m, 3H), 6.66 (s, 1H), 5.51 (s, 1H), 4.21 (m, 2H), 3.77 (m, 2H), 3.10 (m, 1H), 1.20 (d, J=6.0 Hz, 6H), HRMS (m/z): [M+H]$^+$ calculated for C$_{22}$H$_{20}$F$_3$NO$_5$, 436.1366. found, 436.1369.

Excitation/Emission Measurement

Excitation/Emission spectra were taken in ethanol using a Varian Cary 50 spectrofluorometer at 25° C. in a 1 cm path length quartz cell. The excitation slit was set at 5 nm, and the emission slit was set at 5 nm.

JW576 Treatments of Cell

JW576 was dissolved in DMSO and diluted into media or buffer prior to cell or proteome treatment, respectively. For in vitro treatment, final DMSO concentration was 4%. For in situ treatments of cells for ABPP, 2×10$^6$ cells were seeded in 6 cm dishes (100% confluency) 24 hr prior to JW576 pretreatment with or without JW480 (in DMSO at 0.1% final concentration) in serum-free media (3 ml) for the designated time before harvesting cells for ABPP.

Competitive ABPP Experiments

For ABPP experiments, cell lysate and tissue proteomes were treated with 1 µM FP-rhodamine for 30 min at room temperature (501 total reaction volume). Reactions were quenched with one volume of standard 4×SDS/PAGE loading buffer (reducing), separated by SDS/PAGE (10% acrylamide), and visualized in-gel with a Hitachi FMBio IIe flatbed fluorescence scanner (MiraiBio). For experiments involving a preincubation with JW576 in the presence or absence of the non-fluorescent competitor JW480, the reactions were prepared without FP-rhodamine. JW576 were added at the indicated concentration and incubated for the indicated time at 37° C. FP-rhodamine was then added and the reaction was carried out exactly as described above.

2-Acetyl MAGE Hydrolytic Activity Assays

For hydrolytic activity assay, cells were treated in situ with JW576 for 4 hr in serum-free F-12K media before harvesting cells by scraping. Cell lysates (20 µg) in Tris buffer were then incubated with lipid (100 mM, e.g., 2-acetyl MAGE for KIAA1363 activity) at room temperature for 30 min in a volume of 200 ml. Reactions were quenched with 600 ml 2:1 chloroform:methanol and 10 nmol of C12:0 MAGE internal standard was added. The products were extracted into the organic layer, which was extracted and directly injected into LC-MS. Product levels (C16:0 MAGE for KIAA1363 activity) were quantified in relation to internal standard levels and standard curves generated between varying lipid concentration versus constant internal standard levels. Specific activity was determined during the linear phase of enzymatic reactions (i.e., less than 20% substrate utilized)

Recombinant Expression of KIAA1363 in COS7 Cells

Full-length cDNA encoding mouse serine hydrolases was obtained from endogenous source (Daniel et al., 2010). COS7 cells were grown to ~70% confluence in 10-cm dishes in complete medium (DMEM with L-glutamine, nonessential amino acids, sodium pyruvate, and FCS) at 37° C. and 5% CO$_2$. The cells were transiently transfected by using the appropriate cDNA or empty vector control ("mock") and the FUGENE 6 (Roche Applied Science) transfection reagents following the manufacturers' protocols. After 48 hr, the cells were washed twice with phosphate buffered saline (PBS), collected by scraping, resuspended in 0.3 ml PBS, and lysed by sonication. The lysates were used in assay as whole-cell homogenates.

Fluorescence Microscopy Assays

For fluorescence microscopy experiments, 5×10$^5$ cells were plated on glass coverslips in media containing 10% FBS at 37° C. under 5% CO$_2$ and allowed to settle overnight. Cells were washed with PBS twice prior to in situ treatment with JW480 at the indicated concentration for 4 hr in serum-free media. Following pre-treatment with JW480 or DMSO control, cells were washed twice with PBS and subsequently treated with the indicated concentration of JW576 in fresh media. After incubation for the indicated time, cells were washed twice with PBS and fixed at 25° C. for 15 min in 3.7% (w/v) paraformaldehyde in PBS. Fixed cells were then stained with DAPI (Sigma Aldrich), Far-red Wheat-germ agglutinin (Invitrogen) and/or ER-Tracker Red (Invitrogen) according to manufacturers recommendations for 1 hr at 25° C. For image acquisition, processed coverslips were mounted on microscope slides and confocal images were acquired using a fully tunable, filter-based emission collection system (Bio-Rad(Zeiss) Radiance 2100 Rainbow laser scanning confocal microscope) using identical acquisition parameters within experiments. Post-acquisition processing (multi-channel overlay, scale bar addition) was performed using ImageJ software (NIH). Co-localization analyses were performed using Zen imaging software (Zeiss). For these studies, autofluorescent background values were identified on each fluorescence channel and used as a lower limit for quantifiable fluorescence. Fluorescent channels were then compared in a paired fashion by quantifying the percentage of significantly "green" pixels that overlapped with significantly "blue" pixels to compare the colocalization of BODIPY and DAPI, for example. Each comparison was made on a representative field of cells.

Half-Life Measurement

For KIAA1363 half-life measurements, $2\times10^6$ cells were seeded in 6 cm dishes (100% confluency) 24 hr prior to 5 µM JW576 pretreatment in serum-free media (3 ml) for 10 min. Cells were washed with PBS twice and then incubated with 10 µM JW480 in fresh media for the designated time before harvesting cells for ABPP. Integrated band intensities were calculated for the labeled proteins by ImageJ software (NIH) and averaged from three independent cell samples to determine the KIAA1363-JW576 level at each time point.

Preparation of Mouse Tissue Proteomes

Tissues were dounce-homogenized in PBS, pH 7.5, followed by a low-speed spin (1,400 g, 5 min) to remove debris. The supernatant was then subjected to centrifugation (64,000 g, 45 min) to provide the cytosolic fraction in the supernatant and the membrane fraction as a pellet. The pellet was washed and resuspended in PBS buffer by sonication. Total protein concentration in each fraction was determined using a protein assay kit (Bio-Rad). Samples were stored at −80° C. until use.

In Vivo Studies with JW576

JW576 was prepared as a homogenoeus PEG solution by vortexing, sonicating, and gently heating neat compound directly into PEG300 (Fluka) (4 mg ml$^{-1}$ final concentration. Male C57Bl/6J (<6 months old, 20-28 g) and Male KIAA1363-KO mice were treated with JW576 or a PEG vehicle by intraperitoneal injection. After the indicated amount of time, mice were anesthetized with isoflurane and killed by decapitation. Tissues were removed, flash frozen in liquid $N_2$ and stored at −80° C. prior to processing for ABPP gel analysis as indicated above. Animal experiments were conducted in accordance with the guidelines of the institutional Animal Care and Use Committee of The Scripps Research Institute.

CITED DOCUMENTS

Ahn, K., Johnson, D. S., Mileni, M., Beidler, D., Long, J. Z., McKinney, M. K., Weerapana, E., Sadagopan, N., Liimatta, M., Smith, S. E., et al. (2009). Discovery and characterization of a highly selective FAAH inhibitor that reduces inflammatory pain. Chem Biol 16, 411-420.

Albert, D. H., and Anderson, C. E. (1977). Ether-linked glycerolipids in human brain tumors. Lipids 12, 188-192.

Alexander, J. P., and Cravatt, B. F. (2005). Mechanism of carbamate inactivation of FAAH: implications for the design of covalent inhibitors and in vivo functional probes for enzymes. Chem Biol 12, 1179-1187.

Arastu-Kapur, S., Ponder, E. L., Fonovic, U. P., Yeoh, S., Yuan, F., Fonovic, M., Grainger, M., Phillips, C. I., Powers, J. C., and Bogyo, M. (2008). Identification of proteases that regulate erythrocyte rupture by the malaria parasite *Plasmodium falciparum*. Nat Chem Biol 4, 203-213.

Bachovchin, D. A., Ji, T., Li, W., Simon, G. M., Hoover, H., Niessen, S., and Cravatt, B. F. (2010). A superfamily-wide portrait of serine hydrolase inhibition achieved by library-versus-library screening. Proc Natl Acad Sci USA 107, 20941-20946.

Berger, A. B., Vitorino, P. M., and Bogyo, M. (2004). Activity-based protein profiling: applications to biomarker discovery, in vivo imaging and drug discovery. Am J Pharmacogenomics 4, 371-381.

Blank, M. L., Smith, Z. L., Cress, E. A., and Snyder, F. (1990). Characterization of the enzymatic hydrolysis of acetate from alkylacetylglycerols in the de novo pathway of PAF biosynthesis. Biochim Biophys Acta 1042, 153-158.

Blum, G., Mullins, S. R., Kernen, K., Fonovic, M., Jedeszko, C., Rice, M. J., Sloane, B. F., and Bogyo, M. (2005). Dynamic imaging of protease activity with fluorescently quenched activity-based probes. Nat Chem Biol 1, 203-209.

Buchebner, M., Pfeifer, T., Rathke, N., Chandak, P. G., Lass, A., Schreiber, R., Kratzer, A., Zimmermann, R., Sattler, W., Koefeler, H., et al. (2010). Cholesteryl ester hydrolase activity is abolished in HSL−/− macrophages but unchanged in macrophages lacking KIAA1363. J Lipid Res 51, 2896-2908.

Casida, J. E., and Quistad, G. B. (2005). Serine hydrolase targets of organophosphorus toxicants. Chem Biol Interact 157-158, 277-283.

Chiang, K. P., Niessen, S., Saghatelian, A., and Cravatt, B. F. (2006). An enzyme that regulates ether lipid signaling pathways in cancer annotated by multidimensional profiling. Chem Biol 13, 1041-1050.

Cravatt, B. F., Wright, A. T., and Kozarich, J. W. (2008). Activity-Based Protein Profiling: From Enzyme Chemistry to Proteomic Chemistry. Annu Rev Biochem 77, 383-414.

Deu, E., Leyva, M. J., Albrow, V. E., Rice, M. J., Ellman, J. A., and Bogyo, M. Functional studies of *Plasmodium falciparum* dipeptidyl aminopeptidase I using small molecule inhibitors and active site probes. Chem Biol 17, 808-819.

Ellman, G. L., Courtney, K. D., Andres, V., Jr., and Featherstone, R. M. (1961). A new and rapid colorimetric determination of acetylcholinesterase activity. Biochem Pharmacol 7, 88-95.

Ferguson, D. A., Muenster, M. R., Zang, Q., Spencer, J. A., Schageman, J. J., Lian, Y., Garner, H. R., Gaynor, R. B., Huff, J. W., Pertsemlidis, A., et al. (2005). Selective identification of secreted and transmembrane breast cancer markers using *Escherichia coli* ampicillin secretion trap. Cancer Res 65, 8209-8217.

Haverty, P. M., Hon, L. S., Kaminker, J. S., Chant, J., and Zhang, Z. (2009). High-resolution analysis of copy number alterations and associated expression changes in ovarian tumors. BMC Med Genomics 2, 21.

Hoosein, N. M., Boyd, D. D., Hollas, W. J., Mazar, A., Henkin, J., and Chung, L. W. (1991). Involvement of urokinase and its receptor in the invasiveness of human prostatic carcinoma cell lines. Cancer Commun 3, 255-264.

Iacobuzio-Donahue, C. A., Maitra, A., Shen-Ong, G. L., van Heek, T., Ashfaq, R., Meyer, R., Walter, K., Berg, K., Hollingsworth, M. A., Cameron, J. L. et al. (2002). Discovery of novel tumor markers of pancreatic cancer using global gene expression technology. Am J Pathol 160, 1239-1249.

Igarashi, M., Osuga, J., Uozaki, H., Sekiya, M., Nagashima, S., Takahashi, M., Takase, S., Takanashi, M., Li, Y., Ohta, K., et al. (2010). The critical role of neutral cholesterol ester hydrolase 1 in cholesterol removal from human macrophages. Circ Res 107, 1387-1395.

Jessani, N., Liu, Y., Humphrey, M., and Cravatt, B. F. (2002). Enzyme activity profiles of the secreted and membrane proteome that depict cancer invasiveness. Proc Natl Acad Sci USA 99, 10335-10340.

Jessani, N., Niessen, S., Wei, B. Q., Nicolau, M., Humphrey, M., Ji, Y., Han, W., Noh, D. Y., Yates, J. R., 3rd, Jeffrey, S. S., et al. (2005). A streamlined platform for high-content functional proteomics of primary human specimens. Nat Methods 2, 691-697.

Kathuria, S., Gactani, S., Fegley, D., Valino, F., Duranti, A., Tontini, A., Mor, M., Tarzia, G., La Rana, G., Calignano, A., et al. (2003). Modulation of anxiety through blockade of anandamide hydrolysis. Nat Med 9, 76-81.

Krishnasamy, S., Teng, A. L., Dhand, R., Schultz, R. M., and Gross, N. J. (1998). Molecular cloning, characterization, and differential expression pattern of mouse lung surfactant convertase. Am J Physiol 275, L969-975.

Leung, D., Hardouin, C., Boger. D. L., and Cravatt, B. F. (2003). Discovering potent and selective reversible inhibitors of enzymes in complex proteomes. Nat Biotechnol 21, 687-691.

Li, W., Blankman, J. L., and Cravatt, B. F. (2007). A functional proteomic strategy to discover inhibitors for uncharacterized hydrolases. J Am Chem Soc 129, 9594-9595.

Lin. H. J., Ho, F. C., and Lee, C. L. (1978). Abnormal distribution of O-alkyl groups in the neutral glycerolipids from human hepatocellular carcinomas. Cancer Res 38, 946-949.

Liu, Y., Patricelli, M. P., and Cravatt, B. F. (1999). Activity-based protein profiling: the serine hydrolases. Proc Natl Acad Sci USA 96, 14694-14699.

Long, J. Z., Li, W., Booker, L., Burston, J. J., Kinsey, S. G., Schlosburg, J. E., Pavon, F. J., Serrano, A. M., Selley, D. E., Parsons, L. H. et al. (2009a). Selective blockade of 2-arachidonoylglycerol hydrolysis produces cannabinoid behavioral effects. Nat Chem Biol 5, 37-44.

Long, J. Z., Nomura, D. K., and Cravatt, B. F. (2009b). Characterization of monoacylglycerol lipase inhibition reveals differences in central and peripheral endocannabinoid metabolism. Chem Biol 16, 744-753.

Nomura, D. K., Long, J. Z., Niessen, S., Hoover, H. S., Ng, S. W., and Cravatt, B. F. (2010). Monoacylglycerol lipase regulates a fatty acid network that promotes cancer pathogenesis. Cell 140, 49-61.

Okazaki, H., Igarashi, M., Nishi, M., Sekiya, M., Tajima, M., Takase, S., Takanashi, M., Ohta, K., Tamura, Y., Okazaki, S., et al. (2008). Identification of neutral cholesterol ester hydrolase, a key enzyme removing cholesterol from macrophages. J Biol Chem 283, 33357-33364.

Patricelli, M. P., Giang, D. K., Stamp, L. M., and Burbaum, J. J. (2001). Direct visualization of serine hydrolase activities in complex proteome using fluorescent active site-directed probes. Proteomics 1, 1067-1071.

Roos, D. S., and Choppin, P. W. (1984). Tumorigenicity of cell lines with altered lipid composition. Proc Natl Acad Sci USA 81, 7622-7626.

Simon, G. M., and Cravatt, B. F. (2010). Activity-based proteomics of enzyme superfamilies: serine hydrolases as a case study. J Biol Chem 285, 11051-11055.

Snyder, F., and Wood, R. (1969). Alkyl and alk-1-enyl ethers of glycerol in lipids from normal and neoplastic human tissues. Cancer Res 29, 251-257.

Staub, I., and Sieber, S. A. (2009). Beta-lactam probes as selective chemical-proteomic tools for the identification and functional characterization of resistance associated enzymes in MRSA. J Am Chem Soc 131, 6271-6276.

Wood, R., and Snyder, F. (1967). Characterization and identification of glyceryl ether diesters present in tumor cells. J Lipid Res 8, 494-500.

All patents and publications referred to herein are incorporated by reference herein to the same extent as if each individual publication was specifically and individually indicated to be incorporated by reference in its entirety.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A serine hydrolase KIAA1363 inhibitory carbamate compound of formula (I) or a pharmaceutically acceptable salt thereof:

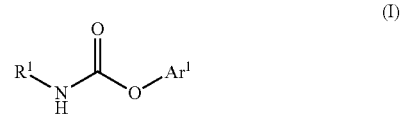

wherein
—NH—C(=O)O— is a carbamate group for reaction with an active serine residue of the serine hydrolase enzyme;
$Ar^1$ is a group of formula (II)

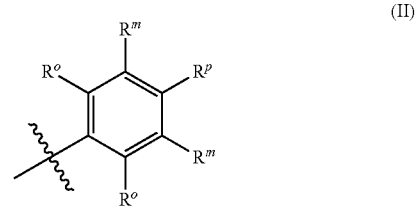

wherein a wavy line indicates a point of bonding of $Ar^1$ to the carbamate group;
each independently selected $R^o$ is H, alkyl, or alkenyl,
each independently selected $R^m$ is H or alkyl,
$R^p$ is H, alkyl, or cycloalkyl;
$R^1$ is
naphthylalkyl.

2. A serine hydrolase KIAA1363 inhibitory carbamate compound of formula (I) or a pharmaceutically acceptable salt thereof:

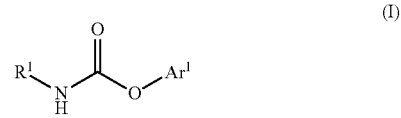

wherein
—NH—C(=O)O— is a carbamate group for reaction with an active serine residue of the serine hydrolase enzyme;

Ar¹ is

[chemical structures]

wherein a wavy line indicates a point of attachment;

R¹ is one of the following:
(a) arylalkyl substituted by (i) halogen or haloalkyl and (ii) optionally a further group selected from the group consisting alkyl, alkenyl, cycloalkyl, halo, haloalkyl, alkoxy, alkylenedioxy, and haloalkoxy; or
(b) naphthylalkyl.

3. A pharmaceutical composition comprising a compound of claim 1 and a pharmaceutically acceptable excipient.

4. A compound selected from the group consisting of

[chemical structures]

, and

[chemical structure with F₃C]

or a pharmaceutically acceptable salt thereof.

5. The compound of claim 4, wherein the compound is

[chemical structure]

or a pharmaceutically acceptable salt thereof.

6. The compound of claim 4, wherein the compound is

[chemical structures with F and F₃C]

or a pharmaceutically acceptable salt thereof.

7. A pharmaceutical composition comprising a compound of claim 5 and a pharmaceutically acceptable excipient.

8. A pharmaceutical composition comprising a compound of claim 6 and a pharmaceutically acceptable excipient.

* * * * *